(12) United States Patent
Codarri Deak et al.

(10) Patent No.: US 12,023,368 B2
(45) Date of Patent: Jul. 2, 2024

(54) IMMUNOCONJUGATES

(71) Applicant: Hoffmann-La Roche Inc., Little Falls, NJ (US)

(72) Inventors: Laura Codarri Deak, Schlieren (CH); Christian Klein, Schlieren (CH); Laura Lauener, Schlieren (CH); Valeria G. Nicolini, Schlieren (CH); Stefan Seeber, Sindelsdorf (DE); Pablo Umana, Schlieren (CH); Inja Waldhauer, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/810,041

(22) Filed: Jun. 30, 2022

(65) Prior Publication Data

US 2023/0134606 A1    May 4, 2023

Related U.S. Application Data

(62) Division of application No. 15/943,237, filed on Apr. 2, 2018, now Pat. No. 11,413,331.

(30) Foreign Application Priority Data

Apr. 3, 2017   (EP) .................... 17164533

(51) Int. Cl.
| | |
|---|---|
| *A61K 38/20* | (2006.01) |
| *A61K 39/395* | (2006.01) |
| *A61K 47/68* | (2017.01) |
| *A61P 35/00* | (2006.01) |
| *C07K 14/55* | (2006.01) |
| *C07K 16/28* | (2006.01) |
| *A61K 38/00* | (2006.01) |
| *A61K 39/00* | (2006.01) |

(52) U.S. Cl.
CPC ...... *A61K 38/2013* (2013.01); *A61K 39/3955* (2013.01); *A61K 47/6813* (2017.08); *A61K 47/6849* (2017.08); *A61K 47/6891* (2017.08); *A61P 35/00* (2018.01); *C07K 14/55* (2013.01); *C07K 16/2818* (2013.01); *A61K 38/00* (2013.01); *A61K 2039/505* (2013.01); *C07K 2317/73* (2013.01); *C07K 2319/74* (2013.01)

(58) Field of Classification Search
CPC ............ A61K 38/2013; A61K 39/3955; A61K 2039/505; C07K 14/55; C07K 16/28; C07K 2319/74; C07K 2317/73
See application file for complete search history.

(56) References Cited

U.S. PATENT DOCUMENTS

| | | | |
|---|---|---|---|
| 5,750,373 A | 12/1998 | Garrard et al. | |
| 6,500,422 B2 | 12/2002 | Biffoni et al. | |
| 7,563,869 B2 | 7/2009 | Honjo et al. | |
| 7,595,048 B2 | 9/2009 | Honjo et al. | |
| 7,985,840 B2 | 7/2011 | Fuh et al. | |
| 8,552,156 B2 | 10/2013 | Takayanagi et al. | |
| 9,067,999 B1 | 6/2015 | Honjo et al. | |
| 9,084,776 B2 | 7/2015 | Korman et al. | |
| 9,163,087 B2 | 10/2015 | Kuchroo et al. | |
| 9,266,938 B2 | 2/2016 | Ast et al. | |
| 9,382,323 B2 | 7/2016 | Brinkmann et al. | |
| 9,447,159 B2 | 9/2016 | Ast et al. | |
| 9,526,797 B2 | 12/2016 | Gerdes et al. | |
| 9,834,607 B2 | 12/2017 | Kuchroo et al. | |
| 9,880,176 B2 | 1/2018 | Jaga et al. | |
| 9,945,869 B2 | 4/2018 | Stubenrauch et al. | |
| 10,184,009 B2 | 1/2019 | Ast et al. | |
| 10,202,464 B2 | 2/2019 | Ast et al. | |
| 10,287,352 B2 | 5/2019 | Codarri-Deak et al. | |
| 10,316,104 B2 | 6/2019 | Ast et al. | |
| 10,344,089 B2 | 7/2019 | Thudium et al. | |
| 10,392,445 B2 | 8/2019 | Amann et al. | |
| 10,562,903 B2 | 2/2020 | Bartels et al. | |
| 10,596,173 B2 | 3/2020 | Lu et al. | |
| 10,603,360 B2 | 3/2020 | Gerdes et al. | |
| 10,718,762 B2 | 7/2020 | Seeber et al. | |
| 10,761,097 B2 | 9/2020 | Stubenrauch et al. | |
| 10,781,262 B2 | 9/2020 | Klien et al. | |
| 10,934,352 B2 | 3/2021 | Kuchroo et al. | |
| 11,111,312 B2 | 9/2021 | Ast et al. | |
| 11,130,810 B2 | 9/2021 | Codarri Deak et al. | |
| 11,130,822 B2 | 9/2021 | Ast et al. | |

(Continued)

FOREIGN PATENT DOCUMENTS

| | | |
|---|---|---|
| CN | 101490085 | 7/2009 |
| CN | 103608040 A | 2/2014 |

(Continued)

OTHER PUBLICATIONS

Agata, Y., et al., "Expression of the PD-1 antigen on the surface of stimulated mouse T and B lymphocytes" Int Immunol 8(5):765-772 (Feb. 6, 1996).

(Continued)

*Primary Examiner* — Xiaozhen Xie

(57) ABSTRACT

The present invention generally relates to immunoconjugates, particularly immunoconjugates comprising a mutant interleukin-2 polypeptide and an antibody that binds to PD-1. In addition, the invention relates to polynucleotide molecules encoding the immunoconjugates, and vectors and host cells comprising such polynucleotide molecules. The invention further relates to methods for producing the mutant immunoconjugates, pharmaceutical compositions comprising the same, and uses thereof.

20 Claims, 38 Drawing Sheets

Specification includes a Sequence Listing.

(56) References Cited

U.S. PATENT DOCUMENTS

| | | |
|---|---|---|
| 11,285,207 B2 | 3/2022 | Codarri-Deak et al. |
| 11,413,331 B2 | 8/2022 | Codarri-Deak et al. |
| 2006/0165685 A1 | 7/2006 | Kreysch et al. |
| 2007/0036783 A1 | 2/2007 | Humeau et al. |
| 2007/0071675 A1 | 3/2007 | Wu et al. |
| 2007/0122378 A1 | 5/2007 | Freeman et al. |
| 2009/0175867 A1 | 7/2009 | Thompson et al. |
| 2009/0217401 A1 | 8/2009 | Korman et al. |
| 2010/0190266 A1 | 7/2010 | Sakita et al. |
| 2010/0247521 A1 | 9/2010 | Jones et al. |
| 2011/0070238 A1 | 3/2011 | Triebel et al. |
| 2012/0189617 A1 | 7/2012 | Takayanagi et al. |
| 2012/0244112 A1 | 9/2012 | Ast et al. |
| 2013/0156774 A1 | 6/2013 | Kuchroo et al. |
| 2014/0242076 A1 | 8/2014 | Kadouche et al. |
| 2014/0242611 A1 | 8/2014 | Bazin et al. |
| 2014/0271684 A1 | 9/2014 | Li et al. |
| 2015/0024410 A1 | 1/2015 | Jaga et al. |
| 2015/0044690 A1 | 2/2015 | Nakada et al. |
| 2015/0090936 A1 | 4/2015 | Hu et al. |
| 2015/0203579 A1 | 7/2015 | Papadopoulos et al. |
| 2015/0204847 A1 | 7/2015 | Thomas et al. |
| 2015/0210769 A1 | 7/2015 | Freeman et al. |
| 2015/0259420 A1 | 9/2015 | Triebel et al. |
| 2015/0274827 A1 | 10/2015 | Pfizenmaier et al. |
| 2015/0315296 A1 | 11/2015 | Schaefer et al. |
| 2016/0175397 A1 | 6/2016 | Umana et al. |
| 2016/0222116 A1 | 8/2016 | Korman et al. |
| 2016/0257749 A1 | 9/2016 | Lifke et al. |
| 2016/0376367 A1 | 12/2016 | Yuan et al. |
| 2017/0114135 A1 | 4/2017 | Codarri Deak et al. |
| 2017/0198037 A1 | 7/2017 | Bonvini et al. |
| 2017/0247454 A1 | 8/2017 | Benz et al. |
| 2018/0072804 A1 | 3/2018 | Lifke et al. |
| 2018/0200338 A1 | 7/2018 | Umana et al. |
| 2018/0326010 A1 | 11/2018 | Codarri Deak et al. |
| 2018/0326011 A1 | 11/2018 | Codarri Deak et al. |
| 2018/0326054 A1 | 11/2018 | Codarri Deak et al. |
| 2018/0328920 A1 | 11/2018 | Seeber et al. |
| 2019/0185566 A1 | 6/2019 | Koller et al. |
| 2019/0248877 A1 | 8/2019 | Amann et al. |
| 2019/0322748 A1 | 10/2019 | Codarri-Deak et al. |
| 2019/0322763 A1 | 10/2019 | Ast et al. |
| 2019/0322765 A1 | 10/2019 | Ast et al. |
| 2019/0374609 A1 | 12/2019 | Umana et al. |
| 2019/0382480 A1 | 12/2019 | Lifke et al. |
| 2019/0382489 A1 | 12/2019 | Benz et al. |
| 2019/0382507 A1 | 12/2019 | Amann et al. |
| 2020/0188526 A1 | 6/2020 | Klein et al. |
| 2020/0197492 A1 | 6/2020 | Geres et al. |
| 2020/0247904 A1 | 8/2020 | Amann et al. |
| 2020/0277372 A1 | 9/2020 | Codarri-Deak et al. |
| 2020/0317774 A1 | 10/2020 | Hofer et al. |
| 2020/0392237 A1 | 12/2020 | Bacac et al. |
| 2021/0009656 A1 | 1/2021 | Bruenker et al. |
| 2021/0070882 A1 | 3/2021 | Bacac et al. |
| 2021/0087291 A1 | 3/2021 | Klein et al. |
| 2021/0324108 A1 | 10/2021 | Amann et al. |
| 2022/0017637 A1 | 1/2022 | Gasser et al. |
| 2022/0049020 A1 | 2/2022 | Regula et al. |
| 2022/0072103 A1 | 3/2022 | Codarri Deak et al. |
| 2022/0242971 A1 | 8/2022 | Ast et al. |
| 2022/0259314 A1 | 8/2022 | Codarri Deak et al. |
| 2022/0387586 A1 | 8/2022 | Codarri Deak et al. |

FOREIGN PATENT DOCUMENTS

| | | |
|---|---|---|
| CN | 103858010 | 6/2014 |
| CN | 104428315 B1 | 9/2017 |
| EA | 005404 B1 | 2/2005 |
| EA | 201690333 A1 | 6/2016 |
| EP | 3455254 A1 | 3/2019 |
| JP | 2005-526018 A1 | 9/2005 |
| JP | 2007-523602 A | 8/2007 |
| JP | 2012-503984 A | 2/2012 |
| JP | 2012-515766 | 7/2012 |
| JP | 2013-521769 | 6/2013 |
| JP | 2014-506793 A | 3/2014 |
| JP | 2014-523401 A | 9/2014 |
| JP | 2017-505125 A | 2/2017 |
| RU | 2406760 C2 | 12/2010 |
| RU | 2412947 C2 | 2/2011 |
| RU | 2494107 C2 | 9/2013 |
| SG | 2014012298 | 6/2014 |
| TW | 201019958 A1 | 6/2010 |
| TW | 201406784 A | 2/2014 |
| TW | 201540727 A | 11/2015 |
| WO | 96/27603 A1 | 9/1996 |
| WO | 00/24782 A2 | 5/2000 |
| WO | 01/77342 A1 | 10/2001 |
| WO | 02/02773 A2 | 1/2002 |
| WO | 02/02773 A3 | 1/2002 |
| WO | 03/042402 A2 | 5/2003 |
| WO | 03/063792 A2 | 8/2003 |
| WO | 2004/004771 A1 | 1/2004 |
| WO | 2004/056875 A1 | 7/2004 |
| WO | 2004/069876 A2 | 8/2004 |
| WO | 2004/072286 A1 | 8/2004 |
| WO | 2004/078928 A2 | 9/2004 |
| WO | 2004/087196 A2 | 10/2004 |
| WO | 2005/020972 A2 | 3/2005 |
| WO | 2005/020972 A3 | 3/2005 |
| WO | 2005/087797 A1 | 9/2005 |
| WO | 2006/121168 A1 | 11/2006 |
| WO | 2006/133396 A2 | 12/2006 |
| WO | 2007/005874 A2 | 1/2007 |
| WO | 2007/062466 A1 | 6/2007 |
| WO | 2008/071447 A2 | 6/2008 |
| WO | 2008/083174 A2 | 7/2008 |
| WO | 2008/138920 A1 | 11/2008 |
| WO | 2008/156712 A1 | 12/2008 |
| WO | 2009/014708 A2 | 1/2009 |
| WO | 2009/024531 A1 | 2/2009 |
| WO | 2009/052623 A1 | 4/2009 |
| WO | 2009/101611 A1 | 8/2009 |
| WO | 2009/114335 A2 | 9/2009 |
| WO | 2010/10051 A1 | 1/2010 |
| WO | 2010/019570 A2 | 2/2010 |
| WO | 2010/027423 A2 | 3/2010 |
| WO | 2010/027828 A2 | 3/2010 |
| WO | 2010/029434 A1 | 3/2010 |
| WO | 2010/029435 A1 | 3/2010 |
| WO | 2010/036959 A2 | 4/2010 |
| WO | 2010/063011 A2 | 6/2010 |
| WO | 2010/084999 A1 | 7/2010 |
| WO | 2010/089411 A2 | 8/2010 |
| WO | 2010/112193 A1 | 10/2010 |
| WO | 2010/145792 A1 | 12/2010 |
| WO | 2011/066342 A2 | 6/2011 |
| WO | 2011/109789 A2 | 9/2011 |
| WO | 2011/110604 A1 | 9/2011 |
| WO | 2011/110621 A1 | 9/2011 |
| WO | 2011/155607 A1 | 12/2011 |
| WO | 2011/159877 A2 | 12/2011 |
| WO | 2012/020006 A2 | 2/2012 |
| WO | 2012/107417 A1 | 8/2012 |
| WO | 2012/130831 A1 | 10/2012 |
| WO | 2012/145493 A1 | 10/2012 |
| WO | 2013/004970 A1 | 1/2013 |
| WO | 2013/006490 A2 | 1/2013 |
| WO | 2013/014668 A1 | 1/2013 |
| WO | 2013/113663 A1 | 8/2013 |
| WO | 2013/164694 A1 | 11/2013 |
| WO | 2014/008218 A1 | 1/2014 |
| WO | 2014/009465 A1 | 1/2014 |
| WO | 2014/023679 A1 | 2/2014 |
| WO | 2014/055784 A1 | 4/2014 |
| WO | 2014/140180 A1 | 9/2014 |
| WO | 2014/179664 A2 | 11/2014 |
| WO | 2015/018528 A1 | 2/2015 |
| WO | 2015/048312 A1 | 4/2015 |
| WO | 2015/085847 A1 | 6/2015 |
| WO | 2015/095423 A2 | 6/2015 |
| WO | 2015/095423 A3 | 6/2015 |

(56) References Cited

FOREIGN PATENT DOCUMENTS

| | | |
|---|---|---|
| WO | 2015/107026 A1 | 7/2015 |
| WO | 2015/112800 A1 | 7/2015 |
| WO | 2015/112900 A1 | 7/2015 |
| WO | 2015/116539 A1 | 8/2015 |
| WO | 2015/138920 A1 | 9/2015 |
| WO | 2015/150447 A1 | 10/2015 |
| WO | 2015/164665 A1 | 10/2015 |
| WO | 2015/200119 A1 | 12/2015 |
| WO | 2016/028672 A1 | 2/2016 |
| WO | 2016/071448 A1 | 5/2016 |
| WO | 2016/075278 A1 | 5/2016 |
| WO | 2016/079050 A1 | 5/2016 |
| WO | 2016/092419 A1 | 6/2016 |
| WO | 2016/106159 A1 | 6/2016 |
| WO | 2016/126858 A2 | 8/2016 |
| WO | 2016/142314 A1 | 9/2016 |
| WO | 2016/200782 A1 | 12/2016 |
| WO | 2016/210129 A1 | 12/2016 |
| WO | 2017/015560 A2 | 1/2017 |
| WO | 2017/037203 A1 | 3/2017 |
| WO | 2017/055399 A1 | 4/2017 |
| WO | 2017/055404 A1 | 4/2017 |
| WO | 2017/055443 A1 | 4/2017 |
| WO | 2017/060144 A1 | 4/2017 |
| WO | 2017/096026 A1 | 6/2017 |
| WO | 2017/172517 A1 | 10/2017 |
| WO | 2017/194442 A1 | 11/2017 |
| WO | 2017/194641 A1 | 11/2017 |
| WO | 2018/184964 A1 | 10/2018 |
| WO | 2018/184965 A1 | 10/2018 |
| WO | 2018/185043 A1 | 10/2018 |
| WO | 2018/185046 A1 | 10/2018 |
| WO | 2018/185232 A1 | 10/2018 |
| WO | 2018185135 A1 | 10/2018 |
| WO | 2021/018859 A2 | 2/2021 |
| WO | 2021/209402 A2 | 10/2021 |
| WO | 2021/260064 A1 | 12/2021 |
| WO | 2022/148732 | 7/2022 |
| WO | 2022/148853 A1 | 7/2022 |
| WO | 2022/189377 A1 | 9/2022 |
| WO | 2022/189380 A1 | 9/2022 |

OTHER PUBLICATIONS

Aggarwal, B., "Signalling pathways of the TNF superfamily: a double-edged sword" Nat Rev Immunol 3(9):745-756 (Sep. 1, 2003).
Almagro and Fransson, "Humanization of antibodies" Front Biosci 13:1619-1633 (Jan. 1, 2008).
Almagro, J., et al., "Humanization of antibodies" Front Biosci 13:1619-1633 (Jan. 1, 2008).
Anderson, A.C., et al., "Promotion of Tissue Inflammation by the Immune Receptor Tim-3 Expressed on Innate Immune Cells" Science 318(5853):1141-1143 (Nov. 16, 2007).
Araki, K., et al., "Programmed Cell Death 1-Directed Immunotherapy for Enhancing T-Cell Function" Cold Spring Harb Symp Quant Biol 78:239-247 (2013).
Ascierto, P. et al., "Clinical Experiences With Anti-CD137 and Anti-PD1 Therapeutic Antibodies" Semin Oncol 27(5):508-516 (Oct. 1, 2010).
Ascierto, P., et al., "2015: The Year of Anti-PD-1/PD-L1s Against Melanoma and Beyond" Ebiomedicine 2(2):92-93 (Feb. 1, 2015).
Banner, D., et al., "Crystal Structure of the Soluble Human 55 kd TNF Receptor-Human TNFβ Complex: Implications for TNF Receptor Activation" Cell 73(3):431-445 (May 7, 1993).
Barber, D. et al., "Restoring function in exhausted CD8 T cells during chronic viral infection" Nature 439(7077):682-687 (Feb. 9, 2006).
Barthelemy, P., et al., "Comprehensive Analysis of the Factors Contributing to the Stability and Solubility of Autonomous Human VH Domains" J Biol Chem 283(6):3639-3654 (Feb. 8, 2008).

Baumann, R., et al., "Functional expression of CD134 by neutrophils" Eur J Immunol 34(8):2268-2275 (Aug. 1, 2004).
Beechem, J., Methods in Enzymology "Chapter 2: Global Analysis of Biochemical and Biophysical Data" Brand, L, and Johnson, M., eds, San Diego, CA-USA:Academic Press, vol. 210:37-54 (1992).
Beiboer, S., et al., "Guided Selection of a Pan Carcinoma Specific Antibody Reveals Similar Binding Characteristic yet Structural Divergence Between the Original Murine Antibody and its Human Equivalent" J Mol Biol 296(3):833-849 (Feb. 25, 2000).
Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses" J Immunol 170(2):711-718 (Jan. 15, 2003).
Bernett, M., et al., "Multiple Bispecific Checkpoint Combinations Promote T cell activation" Poster (Investor Relations presentation) Xencor Inc., Monrovia, California—US, pp. 1 (2016) https://investors.xencor.com/static-files/f388d30a-3d0d-4a69-9a43-876a3b38f79f.
Blackburn, S., et al., "Coregulation of CD8+ T cell exhausted by multiple inhibitory receptors during chronic viral infection" Nat Immunol 10(1):29-37 (Jan. 1, 2009).
Blank, C., et al., "Contribution of the PD-L1/PD-1 pathway to T-cell exhaustion: an update on implications for chronic infections and tumor evasion" Cancer Immunol Immun 56(5):739-745 (May 1, 2007).
Bodmer, J. et al., "The molecular architecture of the TNF superfamily" Trends Biochem Sci 27(1):19-26 (Jan. 1, 2002).
Brahmer, J., et al., "Phase I Study of Single-Agent Anti-Programmed Death-1 (MDX-1106) in Refractory Solid Tumors: Safety, Clinical Activity, Pharmacodynamics, and Immunologic Correlates" J Clin Oncol 28(19):3167-3175 (Jul. 1, 2010).
Brand, F. X., et al., "Prospect for Anti-HER2 Receptor Therapy in Breast Cancer" Anticancer Res 26(1B):463-470 (Jan. 31, 2006).
Broll, K., et al., "CD137 Expression in Tumor Vessel Walls High Correlation With Malignant Tumors" Am J Clin Pathol 115(4):543-549 (Apr. 1, 2001).
Buechele, C., et al., "4-1BB ligand modulates direct and Rituximab-induced NK-cell reactivity in chronic lymphocytic leukemia" Eur J Immunol 42(3):737-748 (Mar. 1, 2012).
Chames, P., et al., "Therapeutic antibodies: successes, limitations and hopes for the future" Br J Pharmacol 157(2):220-233 (May 1, 2009).
Chen, S., et al., "Combination of 4-1BB Agonist and PD-1 Antagonist Promotes Antitumor Effector/Memory CD8 T Cells in a Poorly Immunogenic Tumor Model" Cancer Immunol Res 3(2):149-160 (Feb. 1, 2015).
Chen, X. et al., "Fusion Protein Linkers: Property, Design and Functionality" Adv Drug Deliv Rev 65(10):1357-1369 (Oct. 15, 2013).
Chen, X., et al., "A novel human IL-2 mutein with minimal systemic toxicity exerts greater antitumor efficacy than wild-type IL-2" Cell Deaths Dis 9(10 Suppl 989):1-12 (Oct. 1, 2018).
Choi, B., et al., "4-1BB Functions As a Survival Factor in Dendritic Cells" J Immunol 182(7):4107-4115 (Apr. 1, 2009).
Choi, Y., et al., "Predicting antibody complementarity determining region structures without classification" Mol Biosyst 7(12):3327-3334 (Dec. 1, 2011).
Colman P.M., "Effects of amino acid sequence changes on antibody-antigen interactions" Res Immunol 145:33-36 (1994).
Croft, M. et al., "The significance of OX40 and OX40L to T-cell biology and immune disease" Immunol Rev 229(1):173-191 (May 1, 2009).
Cuadros, C., et al., "Vaccination with dendritic cells pulsed with apoptotic tumors in combination with anti-OX40 and anti-4-1BB monoclonal antibodies induces T cell-mediated protective immunity in Her-2/neu transgenic mice." Int J Cancer 116(6):934-943 (Oct. 10, 2005).
Curran, M., et al., "Combination CTLA-4 blockade and 4-1BB activation enhances tumor rejection by increasing T-cell infiltration, proliferation, and cytokine production" PLOS ONE 6(4):e19499, 1-11 (Apr. 29, 2011).

(56) References Cited

OTHER PUBLICATIONS

Dashivets, T., et al., "Oxidation in the complementarity-determining regions differentially influences the properties of therapeutic antibodies" MABS 8(8):1525-1535 (Nov. 1, 2016).
De Genst, E., et al., "Antibody repertoire development in camelids" Dev Comp Immunol 30(1-2):187-198 ( 2006).
Dempke, W.C.M., et al., "Second- and third-generation drugs for immuno-oncology treatment—The more the better?" Eur J Cancer 74:55-72 (Mar. 1, 2017).
Dermer, G., et al., "Another anniversary for the war on cancer" Nat Biotechnol 12:320 (Mar. 1, 1994).
Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).
Dong, X., et al., "Time-resolved FRET reveals the structural mechanism of SERCA-PLB regulation" Biochem Biophys Res Commun 449(2):196-201 (Jun. 27, 2014).
Dubrot, J., et al., "Treatmet with anti-CD137 mAbs causes intense accumulations of liver T cells without selective antitumor immunotherapeutic effects in this organ" Cancer Immunol Immun 59(8):1223-1233 (Aug. 1, 2010).
Frankel, A.E., et al., "Characterizing of diphtheria fusion proteins targeted to the human interleukin-3 receptor" Protein Eng 13(8):575-581 (Aug. 1, 2000).
Freshney, R.I., et al. Culture of Animal Cells: A Manual of Basic Technique New York: Alan R. Liss, Inc.,:1-7 (1983).
Futagawa, T., et al., "Expression and function of 4-1 BB and 4-1BB ligand on murine dendritic cells" Int Immunol 14(3):275-286 (Mar. 1, 2002).
Gakamsky, D., et al., "Use of fluorescence lifetime technology to provide efficient protection from false hits in screening applications" Anal Biochem 409(1):89-97 (Feb. 1, 2011).
Gehring, A., et al., "Profile of Tumor Antigen-Specific CD8 T Cells in Patients With Hepatitis B Virus-Related Hepatocellular Carcinoma" Gastroenterology 137(2):682-690 (Aug. 1, 2009).
George, J. et al., "Differential Effects of Anti-β2-Glycoprotein I Antibodies on Endothelial Cells and on the Manifestations of Experimental Antiphospholipid Syndrome" Circulation 97(9):900-906 (Mar. 10, 1998).
Golden-Mason, L., et al., "Negative Immune Regulator Tim-3 Is Overexpressed on T Cells in Hepatitis C Virus Infection and Its Blockade Rescues Dysfunctional CD4 and CD8 T Cells" J Virol 83(18):9122-9130 (Sep. 1, 2009).
Golden-Mason, L., et al., "Upregulation of PD-1 Expression on Circulating and Intrahepatic Hepatitis C Virus-Specific CD8 T Cells Associated with Reversible Immune Dysfunction" J Virol 81(17):9249-9258 (Sep. 1, 2007).
Gribbon, P., et al., "Fluorescence readouts in HTS: no gain without pain?" Drug Discov Today 8(22):1035-1043 (Nov. 15, 2003).
Griffiths, A., et al., "Human anti-self antibodies with high specificity from phase display libraries" EMBO J 12(2):725-734 (Feb. 1, 1993).
Guo, Z., et al., "Combined TIM-3 blockade and CD137 activation affords the long-term protection in a murine model of ovarian cancer." J Transl Med 11(215):1-11 (Sep. 17, 2013).
Gura, T., "Systems for Identifying New Drugs Are Often Faulty" Science 278(5340):1041-1042 (Nov. 7, 1997).
Hafler, D., et al., "TIMs: central regulators of immune responses" J Exp Med 205(12):2699-2701 (Nov. 24, 2008).
Heinisch, I., et al., "CD137 activation abrogrates granulocytemacrophage colony-stimulating factor-mediated anti-apoptosis in neutrophils" Eur J Immunol 30(12):3441-3446 (Dec. 1, 2000).
Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).
Hornig, N., et al., "Evaluating combinations of costimulatory antibody-ligand fusion proteins for targeted cancer immunotherapy" Cancer Immunol Immunother 62(8):1369-1380 (May 17, 2013).

Hu, C.Y., et al., "Interleukin-2 reverses CD8+ T cell exhaustion in clinical malignant pleural effusion of lung cancer" Clin Exp Immunol 186(1):106-114 (Oct. 1, 2016).
Huard, B., et al., "Characterization of the major histocompatibility complex class II binding site on LAG-3 protein" PNAS USA 94(11):5744-5749 (May 27, 1997).
International Preliminary Report on Patentability—PCT/EP2015/075820:pp. 1-8 (dated May 18, 2017).
International Preliminary Report on Patentability—PCT/EP2016/073248 (Report dated Apr. 3, 2018, Chapter I),:pp. 1-13 (dated Apr. 12, 2018).
International Preliminary Report on Patentability—PCT/EP2016/073186 (Report dated Apr. 3, 2018, Chapter I),:pp. 1-6 (dated Apr. 12, 2018).
International Preliminary Report on Patentability—PCT/EP2017/061241 (Report dated Nov. 13, 2018, Chapter I),:pp. 1-8 (dated Nov. 13, 2018).
International Preliminary Report on Patentability—PCT/EP2018/058382 (Report dated Oct. 8, 2019, Chapter I),:pp. 1-12 (dated Oct. 8, 2019).
International Preliminary Report on Patentability—PCT/EP2018/058385 (Report dated Oct. 8, 2019, Chapter I),:pp. 1-11 (dated Oct. 8, 2019).
International Preliminary Report on Patentability—PCT/EP2018/058034 (Report dated Oct. 8, 2019, Chapter I),:pp. 1-10 (dated Oct. 17, 2019).
International Preliminary Report on Patentability—PCT/EP2018/058037 (Report dated Oct. 8, 2019, Chapter I),:pp. 1-10 (dated Oct. 17, 2019).
International Search Report—PCT/EP2016/073186 (w/Written Opinion),:pp. 1-10 (dated Dec. 9, 2016).
International Search Report—PCT/EP2015/075820:pp. 1-8 (dated Feb. 4, 2016).
International Search Report—PCT/EP2016/073248:pp. 1-11 (dated Feb. 15, 2017).
International Search Report—PCT/EP2017/061241(w/Written Opinion),:pp. 1-18 (dated Aug. 3, 2017).
International Search Report—PCT/EP2018/058034 (w/Written Opinion),:pp. 1-18 (dated Jun. 6, 2018).
International Search Report—PCT/EP2018/058037:pp. 1-10 (dated Jun. 6, 2018).
International Search Report—PCT/EP2018/058382:pp. 1-10 (dated Jul. 17, 2018).
International Search Report—PCT/EP2018/058385 (w/Written Opinion),:pp. 1-24 (dated Jun. 6, 2018).
Isenberg, I., et al., "The Analysis of Fluorescence Decay by a Method of Moments" Biophys J 9(11):1337-1350 (Nov. 1, 1969).
Jain, R., "Barriers to drug delivery in solid tumors" Sci Am:58-65 (Jul. 1994).
Jameson, D.M. et al., "Investigations of protein-protein interactions using time-resolved fluorescence and phasors" Methods 59(3):278-286 (Mar. 1, 2013).
Jin, H., et al., "Cooperation of Tim-3 and PD-1 in CD8 T-cell exhaustion during chronic viral infection" PNAS 107(33):14733-14738 (Aug. 17, 2010).
Jones, R., et al., "Tim-3 expression defines a novel population of dysfunctional T cells with highly elevated frequencies in progressive HIV-1 infection" J Exp Med 205(12):2763-2779 (Nov. 24, 2008).
Ju, S., et al., "Eradication of established renal cell carcinoma by a combination of 5-fluorouracil and anti-4-1BB monoclonal antibody in mice." Int J Cancer 122(12):2784-2790 (Jun. 15, 2008).
Kienzle, G., et al., "CD137 (ILA/4-1BB), expressed by primary human monocytes, induces monocyte activation and apoptosis of B lymphocytes" Int Immunol 12(1):73-82 (Jan. 1, 2000).
Kikushige, Y., et al., "TIM-3 as a Novel Therapeutic Target for Eradicating Acute Myelogenous Leukemia Stem Cells" Int J Hematol 98(6):627-633 (Dec. 1, 2013).
Kim, D., et al., "4-1BB Engagement Costimulates NKT Cell Activation and Exacerbates NKT Cell Ligand-Induced Airway Hyperresponsiveness and Inflammation" J Immunol 180(4):2062-2068 (Feb. 1, 2008).

(56) References Cited

OTHER PUBLICATIONS

Kim, Y. H., et al., "Mechanisms involved in synergistic anticancer effects of anti-4-1BB and cyclophosphamide therapy." Mol Cancer Ther 8(2):469-478 (Feb. 1, 2009).

Klebanoff, C., et al., "IL-15 enhances the in vivo antitumor activity of tumor-reactive CD8+ T Cells" PNAS USA 101(7):1969-1974 (Feb. 17, 2004).

Klimka, A. et al., "Human anti-CD30 recombinant antibodies by guided phage antibody selection using cell panning" Brit J Cancer 83(2):252-260 (Jun. 15, 2000).

Klooster, R., et al., "Generation of immuno-modulatory receptor binding bispecific antibodies to modulate tumor immunity (B088)" Poster ICIC, New York, NY-US, pp. 1 ( Sep. 26, 2016) https://merus.nl/app/uploads/2019/02/Poster-ICIC-New-York-26Sep16.pdf.

Knutson, J.R., et al., "Simultaneous analysis of multiple fluorescence decay curves: A global approach" Chem Phys Lett 102(6):501-507 (Dec. 9, 1983).

Koguchi, K., et al., "Dysregulated T cell expression of TIM3 in multiple sclerosis" J Exp Med 203(6):1413-1418 (Jun. 12, 2006).

Kraman, M. et al., "A LAG-3/PD-L1 bispecific antibody inhibits tumour growth in two syngeneic colon carcinoma models" Cancer Res 77(13):1 (Jul. 1, 2017).

Kwon, B., et al., "cDNA sequences of two inducible T-cell genes" PNAS USA 86(6):1963-1967 (Mar. 1, 1989).

Lebakken, C.S., et al., "A fluorescence lifetime based binding assay to characterize kinase inhibitors" J Biomol Screen 12(6):828-841 (Sep. 1, 2007).

Lee, H., et al., "Combinatorial therapy for liver metastatic colon cancer: dendritic cell vaccine and low-dose agonistic anti-4-1BB antibody costimulatory signal" J Surg Res 169(1):e43-50 (Jul. 1, 2011).

Levitsky, V., et al., "The clonal composition of a peptide-specific oligoclonal CTL repertoire selected in response to persistent EBV infection is stable over time." J Immunol 161(2):594-601 (Jun. 30, 1998).

Li and Ravetch, "Inhibitory Fcγ Receptor Engagement Drives Adjuvant and Anti-Tumor Activities of Agonistic CD40 Antibodies" Science 333(6045):1030-1034 (Aug. 19, 2011).

Lin, W., et al., "Fc-dependent expression of CD137 on human NK cells: insights into agonistic effects of anti-CD137 monoclonal antibodies" Blood 112(3):699-707 (Aug. 1, 2008).

Lippincott-Schwartz, "Antibodies in Cell Biological Tools" Current Protocols in Cell Biology:16.0.1-16.0.2 ( 2002).

Maeda, Y., et al., "Engineering of functional chimeric protein G-Vargula luciferase" Anal Biochem 249(2):147-152 (Jul. 1, 1997).

Majeti, R., et al., "Dysregulated gene expression networks in human acute myelogenous leukemia stem cells" PNAS 106(9):3396-3401 (Mar. 3, 2009).

Malia, T., et al., "Epitope mapping and structural basis for the recognition of phosphorylated tau by the anti-tau antibody AT8" Proteins 84(4):427-434 (Apr. 1, 2016).

Mallender, W.D., et al., "Inter-Active-Site Distance and Solution Dynamics of a Bivalent-Bispecific Single-Chain Antibody Molecule" Biochemistry 33(33):10100-10108 (Aug. 1, 1994).

Maltman, B., et al., "9-Aminoacridine peptide derivatives as versatile reporter systems for use in fluorescence lifetime assays" Chem Commun [CAMB] 46(37):6929-6931 (Oct. 7, 2010).

Mariuzza, R. et al., "The structural basis of antigen-antibody recognition" Annu Rev Biophys Chem 16:139-159 (Jun. 1, 1987).

Markwick, L., et al., "Blockade of PD1 and TIM3 Restores Innate and Adaptive Immunity in Patients With Acute Alcoholic Hepatitis" Gastroenterology 148(3):590-602 (Mar. 1, 2015).

McMahan, R., et al., "Dual TIM-3/PD-1 Expression on Non-Effector CD4+ T Cells and HCV-Specific CD8+ T Cells is Associated with Development of Persistence in Acute HCV Infection" Hepatology (Abstract #1368), 50(Suppl 4) ( 2009).

Melero, I. et al., "Monoclonal Antibodies Against the 4-1BB T-cell Activation Molecule Eradicate Established Tumors" Nat Med 3(6):682-685 (Jun. 1, 1997).

Melero, I. et al., "NK1.1 Cells Express 4-1BB (CDw137) Costimulatory Molecule and Are Required for Tumor Immunity Elicited by Anti-4-1BB Monoclonal Antibodies" Cell Immunol 190(2 Suppl CI981396):167-172 (Dec. 15, 1998).

Merchant, A., et al., "An efficient route to human bispecific IgG" Nat Biotechnol 16(7):677-681 (Jul. 1, 1998).

Moger, J., et al., "The Application of Fluorescence Lifetime Readouts in High-Throughput Screening" J Biomol Screen 11(7):765-772 (Oct. 1, 2006).

Monney, L., et al., "Th1-specific cell surface protein Tim-3 regulates macrophage activation and severity of an autoimmune disease" Nature 415(6871):536-541 (Jan. 31, 2002).

Morales-Kastresana, A., et al., "Combined immunostimulatory monocolonal antibodies extend survival in an aggressive transgenic heptocellular carcinoma mouse model" Clin Cancer Res 19(22):6151-6162 (Nov. 1, 2013).

Morales-Kastresana, A., et al., "Essential complicity of perforin-granzyme and FAS-L mechanisms to achieve tumor rejection following treatment with anti-CD137 mAb" J Immunother Cancer 1(3):1-6 (May 29, 2013).

Mueller, D. et al., "A Novel Antibody—4-1BBL Fusion Protein for Targeted Costimulation in Cancer Immunotherapy" J Immunother 31(8):714-722 (Oct. 1, 2008).

Muretta, J., et al., "High-performance time-resolved fluorescence by direct waveform recording." Rev Sci Instrum 81(10 Suppl 103101):1-8 (Oct. 1, 2010).

Murillo, O., et al., "In vivo depletion of DC impairs the anti-tumor effect of agonistic anti-CD137 mAb" Eur J Immunol 39(9):2424-2436 (Sep. 1, 2009).

Nakamoto, N., et al., "Synergistic Reversal of Intrahepatic HCV-Specific CD8 T Cell Exhaustion by Combined PD-1/CTLA-4 Blockade" PLOS Pathog 5(2):e1000313, 1-13 (Feb. 1, 2009).

Narazaki, H., et al., "CD137 agonist antibody prevents cancer recurrence: contribution of CD137 on both hematopoietic and nonhematopoietic cells" Blood 115(10):1941-1948 (Mar. 11, 2010).

Ngiow, S., et al., "Review: Prospects for TIM3-Targeted Antitumor Immunotherapy" Cancer Res 71(21):6567-6571 (Nov. 1, 2011).

Nishimoto, H., et al., "Costimulation of mast cells by 4-1BB, a member of the tumor necrosis factor receptor superfamily, with the high-affinity IgE receptor" Blood 106(13):4241-4248 (Dec. 15, 2005).

Ohaegbulam, K., et al., "Human cancer immunotherapy with antibodies to the PD-1 and PD-L1 pathway" Trends Mol Med 21(1):24-33 (Jan. 1, 2015).

Okazaki, T., et al., "New regulatory co-receptors: inducible co-stimulator and PD-1" Curr Opin Immunol 14(6):779-782 (Dec. 1, 2002).

Olofsson, P., et al., "CD137 Is Expressed in Human Atherosclerosis and Promotes Development of Plaque Inflammation in Hypercholesterolemic Mice" Circulation 117(10):1292-1301 (Mar. 11, 2008).

Padlan, E. et al., "Anatomy of the Antibody Molecule" Mol Immunol 31(3):169-217 (Feb. 1, 1994).

Palazon, A., et al., "Agonist Anti-CD137 mAb Act on Tumor Endothelial Cells to Enhance Recruitment of Activated T Lymphocytes" Cancer Res 71(3):801-811 (Feb. 1, 2011).

Pan, Q., et al., "Blocking neuropilin-1 function has an additive effect with anti-VEGF to inhibit tumor growth" Cancer Cell 11(1):53-67 (Jan. 1, 2007).

Paterson, M.J., et al., "A fluorescence lifetime-based assay for serine and threonine kinases that is suitable for high-throughput screening" Anal Biochem 402(1):54-64 (Jul. 1, 2010).

Philips, G.K., et al., "Therapeutic uses of anti-PD-1 and anti-PD-L1 antibodies" Int Immunol 27(1):39-46 (Jan. 1, 2015).

Roitt, I.,, "Different antigen antibody binding is ensured by hypervariable sequences of antigen-recognizing centers" Immunologiya:110-111 ( 2000).

Rudikoff, S., et al., "Single amino acid substitution altering antigen-binding specificity" PNAS USA 79(6):1979-1983 (Mar. 1, 1982).

Sakuishi, K., et al., "Targeting Tim-3 and PD-1 pathways to reverse T cell exhaustion and restore anti-tumor immunity" J Exp Med 207(10):2187-2194 (Sep. 27, 2010).

(56) References Cited

OTHER PUBLICATIONS

Sakuishi, K., et al., "TIM3+FOXP3+ regulatory T cells are tissue-specific promoters of T-cell dysfunction in cancer" Oncoimmunology 2(4):e23849, 1-9 (Apr. 1, 2013).
Schwarz, H., et al., "ILA, the Human 4-1BB Homologue, Is Inducible in Lymphoid and Other Cell Lineages" Blood 85(4):1043-1052 (Feb. 15, 1995).
Shao, Z., et al., "Mini-Review: CD137 ligand, a member of the tumor necrosis factor family, regulates immune responses via reverse signal transduction" J Leukocyte Biol 89(1):21-29 (Jan. 1, 2011).
Shen, L., et al., "Construction and Expression of Anti-B7-1 /B7-2-BsAb for Feature Analysis of its binding with antigen" Chinese J Immunol (w/Eng. Abstract), 31:927-931 (Jul. 14, 2015).
Sheridan, C., et al., "Cautious optimism surrounds early clinical data for PD-1 blocker" Nat Biotechnol 30(8):729-730 (Aug. 1, 2012).
Shi, W., et al., "Augmented antitumor effects of radiation therapy by 4-1BB antibody (BMS-469492) treatment." Anticancer Res 26(5A):3445-3453 (Sep. 2006).
Shindo, Y., et al., "Combination Immunotherapy with 4-1BB activation and PD-1 blockade enhances antitumor efficacy in a mouse model of subcutaneous tumor" Anticancer Res 35(1):129-136 (Jan. 1, 2015).
Sierro, S., et al., "The CD4-like molecule LAG-3, biology and therapeutic applications" Expert Opin Ther Tar 15(1):91-101 (Jan. 1, 2011).
Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).
Singer, M. et al., "Structure of Proteins" Genes & Genomes (Geny i genomy Moscow: Mir, 1991), 1:67-69 ( 1991).
Skosyrev, V.S., et al., "The Dependence of Stability of the Green Fluorescent Protein-Obelin Hybrids on the Nature of Their Constituent Modules and the Structure of the Amino Acid Linker" Bioorg Khim (Russ. J Bioorg Chem) 27(5):323-329 (Sep. 30, 2001).
Snell, L., et al., "T-cell intrinsic effects of GITR and 4-1BB during viral infection and cancer immunotherapy" Immunol Rev 244(1):197-217 (Nov. 1, 2011).
Song, J. et al., "Activation of NF-kB1 by OX40 Contributes to Antigen-Driven T Cell Expansion and Survival" J Immunol 180(11):7240-7248 (Jun. 1, 2008).
Stagg, J., et al., "Anti-ErbB-2 mAb therapy requires type I and II interferons and synergizes with anti-PD-1 or anti-CD137 mAb therapy" PNAS USA 108(17):7142-7147 (Apr. 26, 2011).
Strome, S., et al., "A Mechanistic Perspective of Monoclonal Antibodies in Cancer Therapy Beyond Target-Related Effects" Oncologist 12(9):1084-1095 (Sep. 1, 2007).
Takamura, S., et al., "Premature Terminal Exhaustion of Friend Virus-Specific Effector CD8 + T Cells by Rapid Induction of Multiple Inhibitory Receptors" J Immunol 184(9):4696-4707 (May 1, 2010).
Tan, S., et al., "An unexpected N-terminal loop in PD-1 dominates binding by nivolumab" Nat Commun 8(14369):1-10 (Feb. 6, 2017).
Teng, M., et al., "CDld-Based Combination Therapy Eradicates Established Tumors in Mice" J Immunol 183(3):1911-1920 (Aug. 1, 2009).
Thorne, N., et al., "Apparent activity in high-throughput screening: origins of compound-dependent assay interference" Curr Opin Chem Biol 14(3):315-324 (Jun. 1, 2010).
Tokuriki, N. et al., "Stability effects of mutations and protein evolvability" Curr Opin Struct Biol 19(5):596-604 (Oct. 1, 2009).
Topalian, S., et al., "Survival, Durable Tumor Remission, and Long-Term Safety in Nivolumab" J Clin Oncol 32(10):1020-1030 (Apr. 1, 2014).
Tribel, F., et al., "A soluble lymphocyte activation gene-3 (sLAG-3) protein as a prognostic factor in human breast cancer expressing estrogen or progesterone receptors" Cancer Lett 235(1):147-153 (Apr. 8, 2006).
Vajdos, F.F., et al., "Comprehensive functional maps of the antigen-binding site of an anti-ErbB2 antibody obtained with shotgun scanning mutagenesis" J Mol Biol 320(2):415-428 (Jul. 5, 2002).
Vig, B., et al., "Amino acids as promoieties in prodrug design and development" Adv Drug Deliv Rev 65(10):1370-1385 (Oct. 15, 2013).
Von Kempis, J., et al., "Differentiation-dependent and stimulus-specific expression of ILA, the human 4-1BB-homologue, in cells of mesenchymal origin" Steoarthr Cartilage 5(6):394-406 (Nov. 1, 1997).
Wang, S-C, et al., "PD-1 and Tim-3 pathways are associated with regulatory CD8+ T-cell function in decidua and maintenance of normal pregnancy" Cell Death Dis 6(5):e1738, 1-10 (May 1, 2015).
Ward, E., et al., "Binding activities of a repertoire of single immunoglobulin variable domains secreted from *Escherichia coli*" Nature 341(6242):544-546 (Oct. 12, 1989).
Watts, T., "TNF/TNFR family members in costimulation of T cell responses" Annu Rev Immunol 23:23-68 (Sep. 2005).
Wei, H. et al., "Dual targeting of CD137 co-stimulatory and PD-1 co-inhibitory molecules for ovarian cancer immunotherapy" Oncoimmunology 3(4):e28248, 1-3 (Mar. 28, 2014).
Wei, H., et al., "Combinatorial PD-1 blockade and CD137 activation has therapeutic efficacy in murine cancer models and synergizes and cisplatin" PLOS ONE 8(12):e84927, 1-11 (Dec. 19, 2013).
Weinberg, A., et al., "Engagement of the OX-40 Receptor In Vivo Enhances Antitumor Immunity" J Immunol 164(4):2160-2169 (Feb. 15, 2000).
West, E.E., et al., "PD-L1 blockade synergizes with IL-2 therapy in reinvigorating exhausted T cells" J Clin Invest 123(6):2604-2615 (Jun. 3, 2013).
Wilcox, R., et al., "Cutting Edge: Expression of Functional CD137 Receptor by Dendritic Cells" J Immunol 168(9):4262-4267 (May 1, 2002).
Wilcox, R., et al., "Ligation of CD137 receptor prevents and reverses established anergy of CD8+ cytolytic T lymphocytes in vivo" Blood 103(1):177-184 (Jan. 1, 2004).
Woo, S., et al., "Immune inhibitory molecules LAG-3 and PD-1 synergistically regulate T cell function to promote tumoral immune escape" Cancer Res 72(4):917-927 (Feb. 15, 2012).
Wozney, J., Methods in Enzymology: Guide to Protein Purification "55: Using Purified Protein to Clone its Gene" Deutscher, Murray, ed., San Diego, CA-US:Academic Press, Inc.—Harcourt Brace Jovanivich, Publishers, vol. 182:738-751 ( 1990).
Xu, Z., et al., "Membrane-type TIM3 Promotes Anti-tumor Immunity in Tumor Bearing Mice" Chinese J Med Mol Biol (with English Abstract.), 4(3):200-203 (Jan. 31, 2007).
Zhang, N. et al., "Targeted and untargeted CD137L fusion proteins for the immunotherapy of experimental solid tumors." Clin Cancer Res 13(9):2758-2767 (May 1, 2007).
Zhang, X., et al., "CD137 Promotes Proliferation and Survival of Human B Cells" J Immunol 184(2):787-795 (Jan. 15, 2010).
Zhou, Q., et al., "Coexpression of Tim-3 and PD-1 identifies a CD8+ T-cell exhaustion phenotype in mice with disseminated acute myelogenous leukemia" Blood 117(17):4501-4510 (Apr. 28, 2011).
Zitvogel, L. et al., "Targeting PD-1/PD-L1 interactions for cancer immunotherapy" Oncoimmunology 1(8):1223-1225 (Nov. 1, 2012).
Zitvogel, L., et al., "Cancer despite immunosurveillance: immunoselection and immunosubversion" Nat Rev Immunol 6(10):715-727 (Oct. 1, 2006).
Carson W., et al., "Braking Bad: Blockage of Inhibitory Pathways Improves Interleukin-15 Therapy" Clinical Cancer Research (doi:10.1158/1078-0432.CCR-10-2658), 16 (2010).
Conlon K.C., et al., "Redistribution, 2-29 Hyperproliferation, Activation of Natural Killer Cells and CDS T Cells, and Cytokine Production During First-in-Human Clinical Trial of Recombinant Human Interleukin-15 in Patients With Cancer" Journal of Clinical Oncology (XP055550401, US ISSN: 0732-183X, DOI: 10.1200/JC0.2014.57.3329), 33(1):74-82 (Jan. 1, 2015).
Hu C., et al., "Interleukin-2 reverses CD8+ T cell exhaustion in clinical malignant pleural effusion of lung cancer" Clinical and Experimental Immunology (doi:10.1111/cei.12845), 186:106-114 ( 2016).

(56) References Cited

OTHER PUBLICATIONS

Kaspar M., et al., "The antibody-mediated targeted delivery of interleukin-15 and GM-CSF to the tumor neovasculature inhibits tumor growth and metastasis" Cancer Research, American Association for Cancer Research (XP002468217, ISSN: 0008-5472, DOI: 10.1158/0008- 5472.CAN-07-0283), 67(10):4940-4948 (May 1, 2007).

Pilipow K., et al., "IL15 and T-cell Sternness in T-cell-Based Cancer Immunotherapy" Cancer Research (XP093048928, US ISSN: 0008-5472, DOI: 10.1158/0008-5472.CAN-15-1498 Retrieved from the Internet: URL:https://www.ncbi.nlm.nih.gov/pmc/articles/PMC4681597/pdf/nihms-718011.pdf), 75(24):5187-5193 (Dec. 15, 2015).

Steel J., et al., "Interleukin-15 biology and its therapeutic implications in cancer" Trends Pharmacol Sci. (doi:10.1016/j.tips.2011.09.004), 33(1):35-41 (2012).

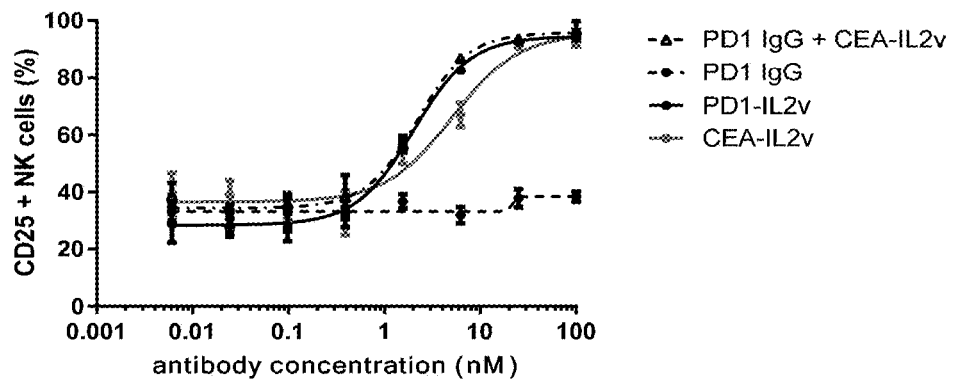
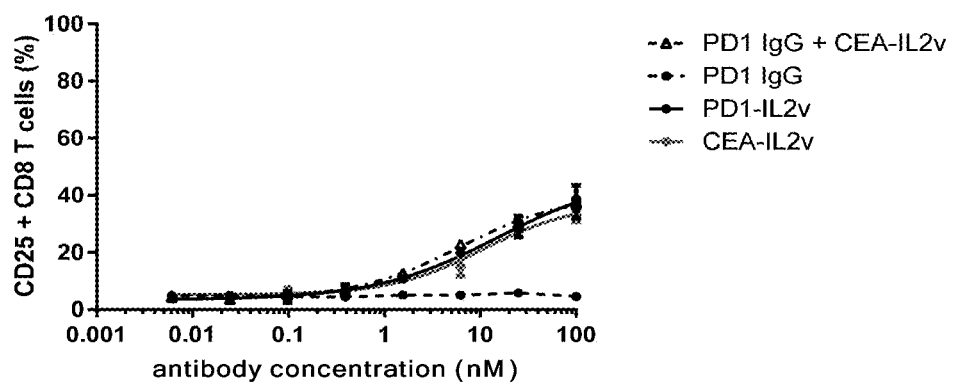
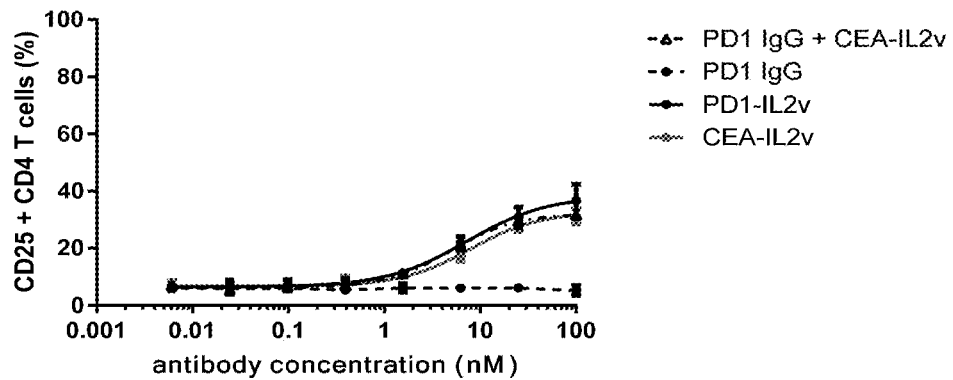

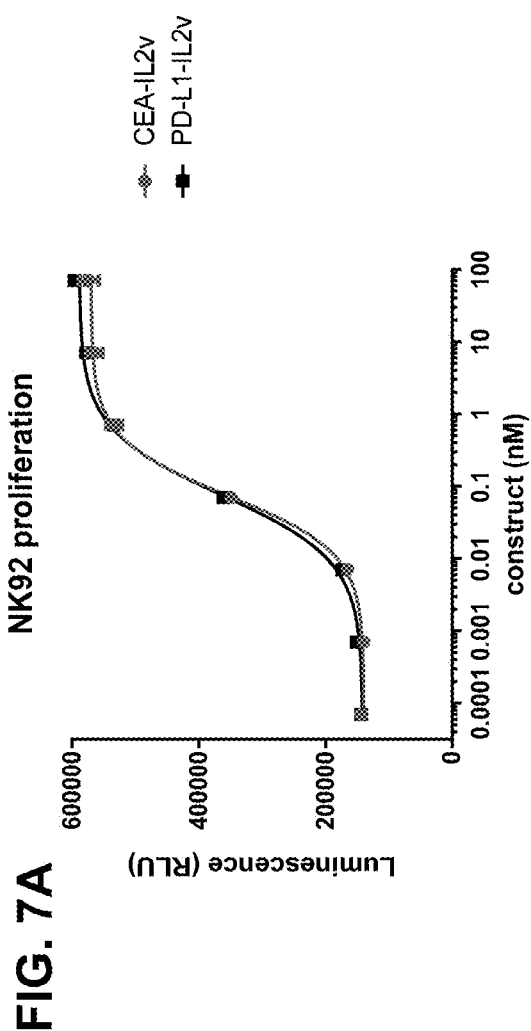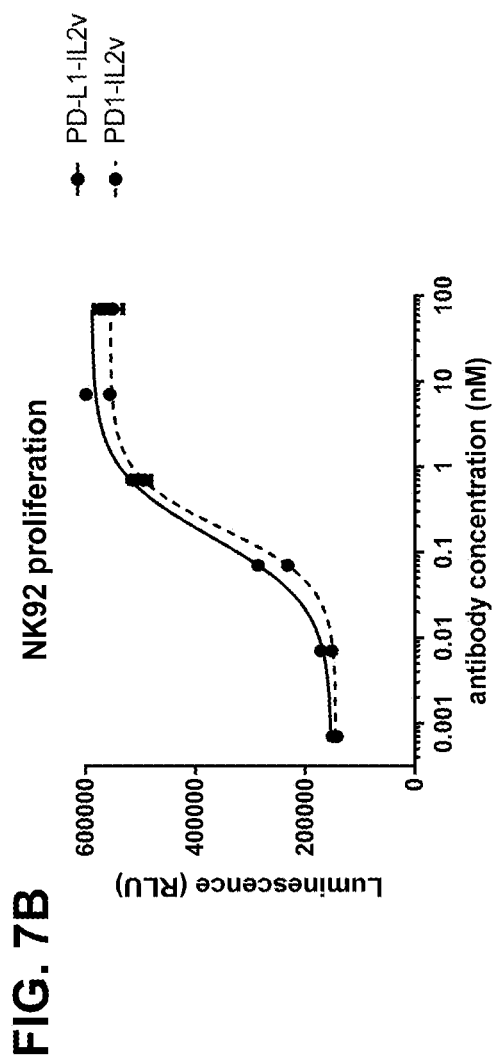

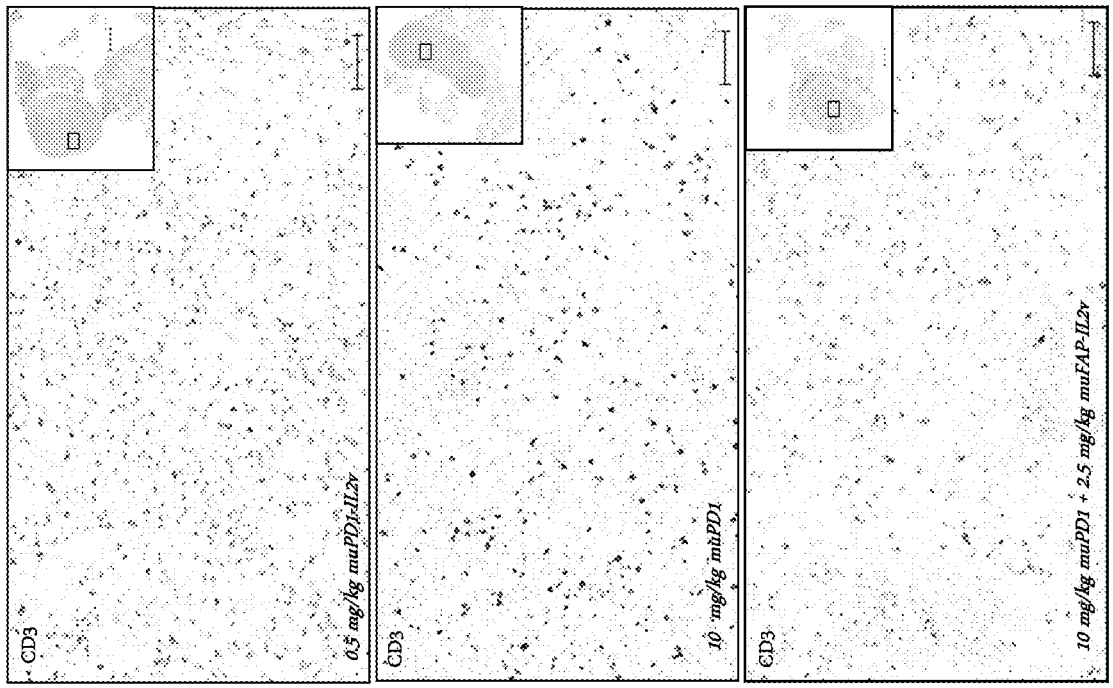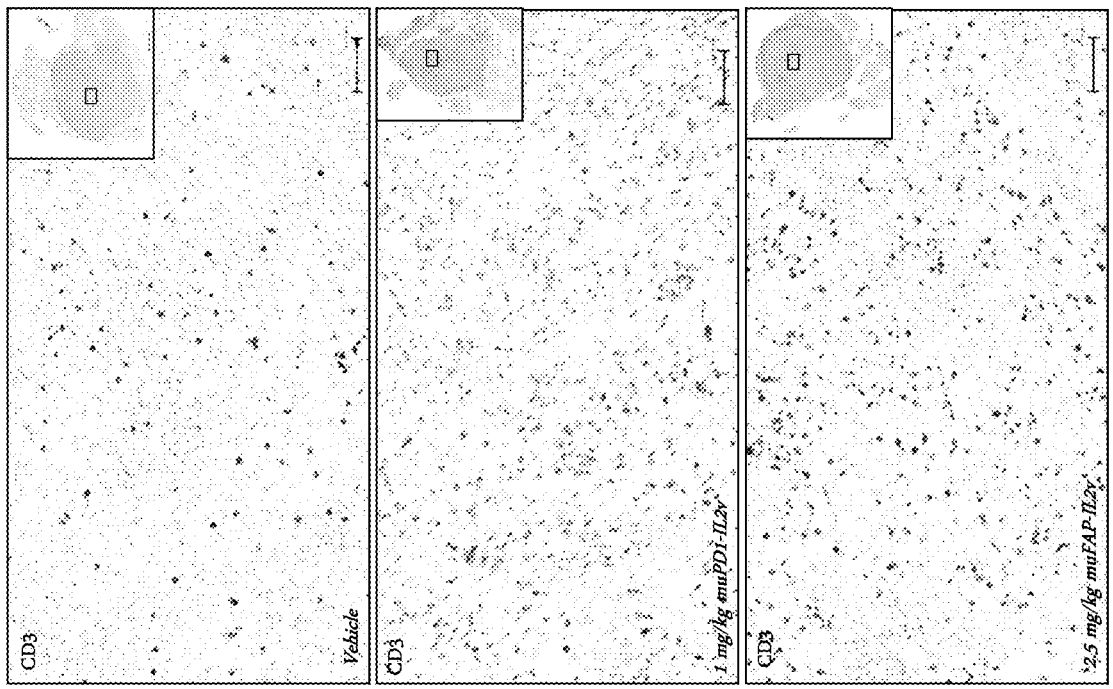
FIG. 18A

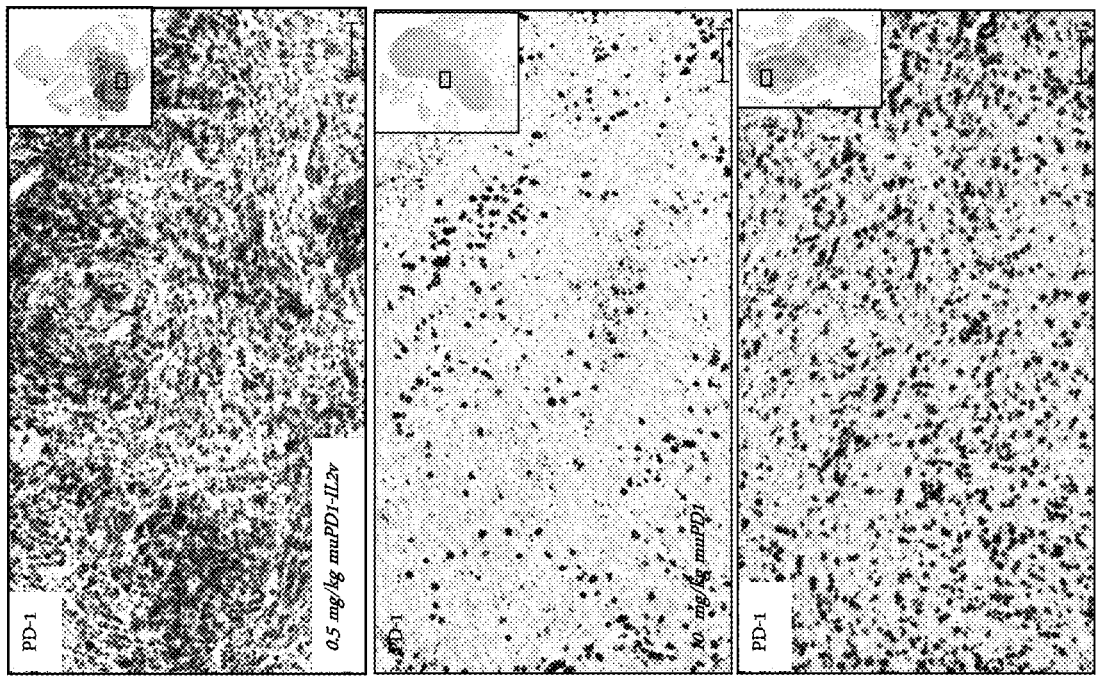
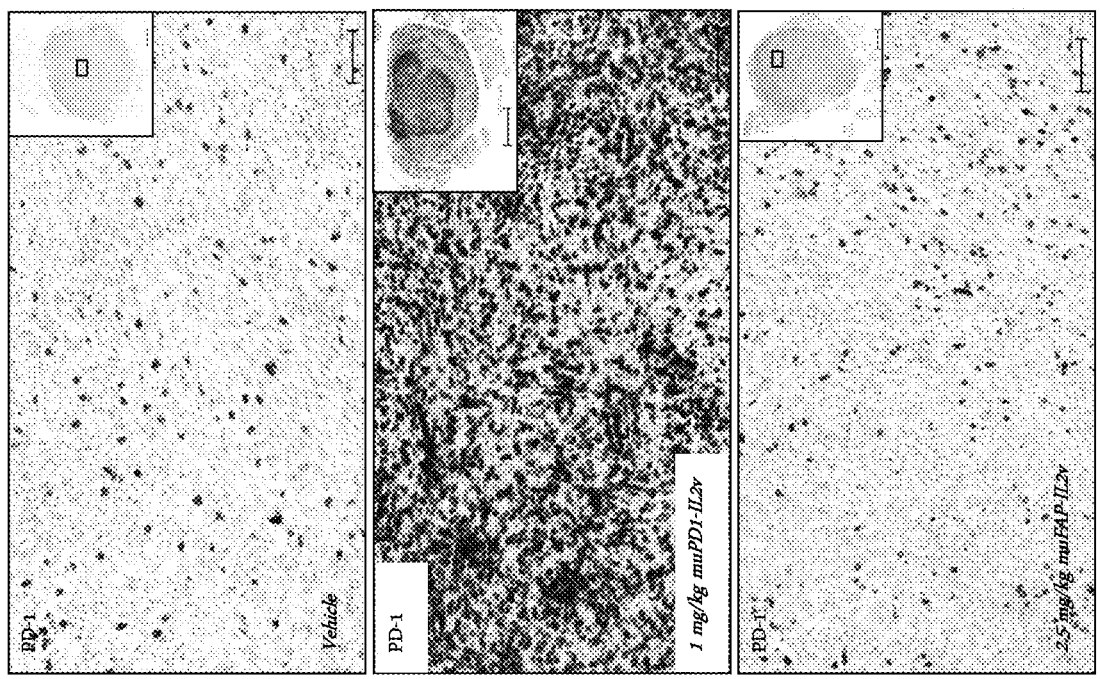
FIG. 19

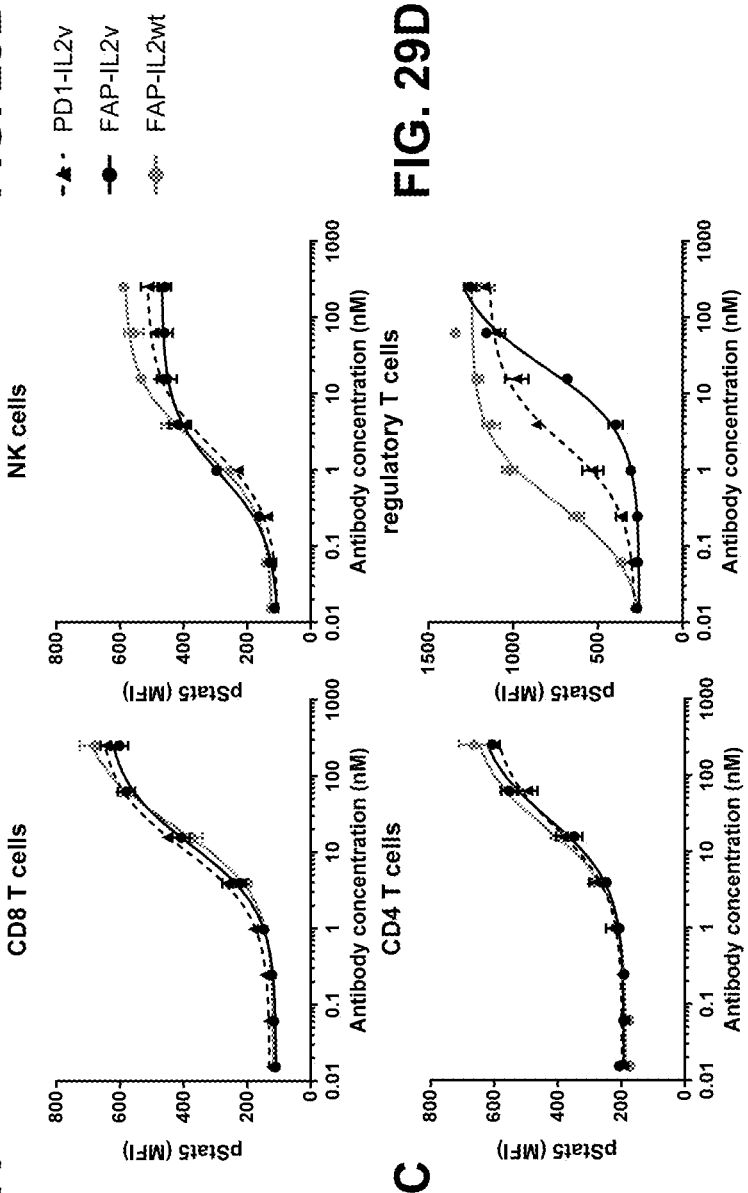

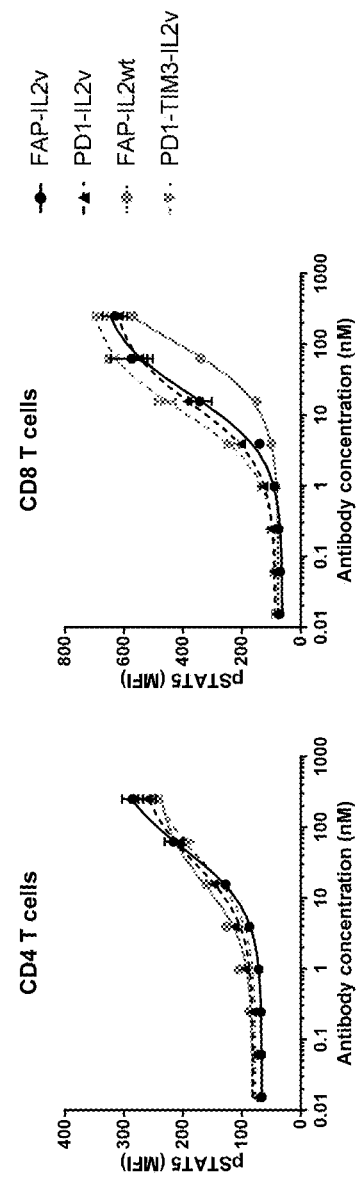
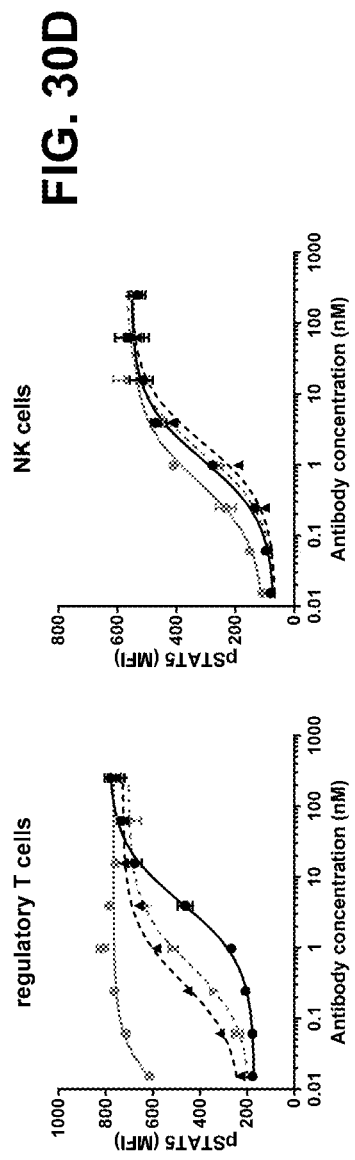
FIG. 30A  FIG. 30B  FIG. 30C  FIG. 30D

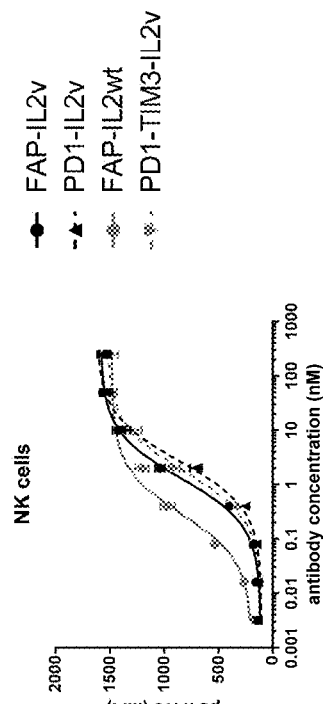
FIG. 32A
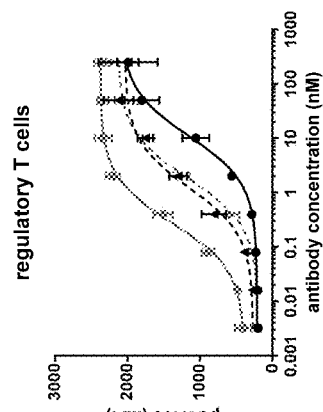
FIG. 32B
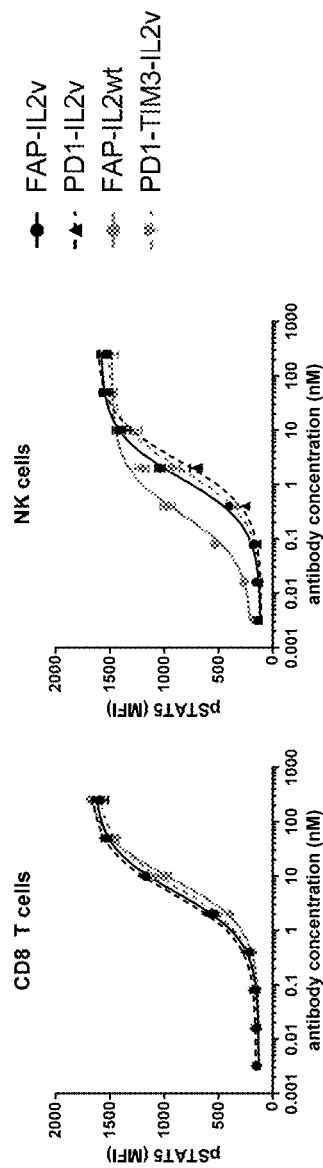
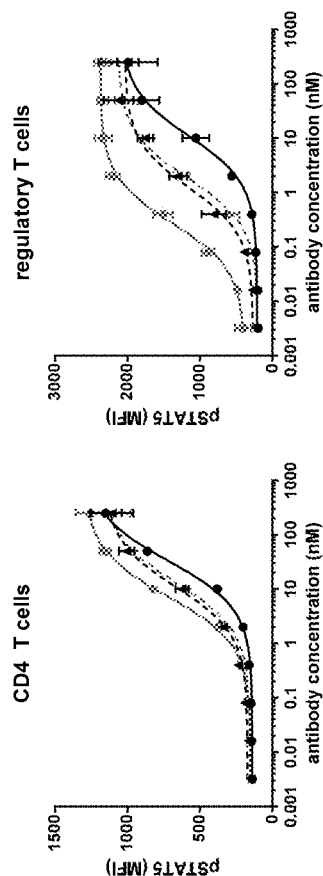
FIG. 32C
FIG. 32D

```
                            SEQUENCE LISTING

<160> NUMBER OF SEQ ID NOS: 51

<210> SEQ ID NO 1
    <211> LENGTH: 4
    <212> TYPE: PRT
    <213> ORGANISM: Artificial Sequence
    <220> FEATURE:
    <223> OTHER INFORMATION: Synthetic construct

<400> SEQUENCE: 1

Ser Ser Tyr Thr
    1

<210> SEQ ID NO 2
    <211> LENGTH: 8
    <212> TYPE: PRT
    <213> ORGANISM: Artificial Sequence
    <220> FEATURE:
    <223> OTHER INFORMATION: Synthetic construct

<400> SEQUENCE: 2

Ser Gly Gly Gly Arg Asp Ile Tyr
    1               5

<210> SEQ ID NO 3
    <211> LENGTH: 5
    <212> TYPE: PRT
    <213> ORGANISM: Artificial Sequence
    <220> FEATURE:
    <223> OTHER INFORMATION: Synthetic Construct

<400> SEQUENCE: 3

Gly Arg Val Tyr Phe
    1               5

<210> SEQ ID NO 4
    <211> LENGTH: 6
    <212> TYPE: PRT
    <213> ORGANISM: Artificial Sequence
    <220> FEATURE:
    <223> OTHER INFORMATION: Synthetic Construct

<400> SEQUENCE: 4

Thr Ser Asp Asn Ser Phe
    1               5

<210> SEQ ID NO 5
    <211> LENGTH: 7
    <212> TYPE: PRT
    <213> ORGANISM: Artificial Sequence
    <220> FEATURE:
    <223> OTHER INFORMATION: Synthetic Construct
```

```
<400> SEQUENCE: 5

Arg Ser Ser Thr Leu Glu Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Asn Tyr Asp Val Pro Trp
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic Construct

<400> SEQUENCE: 7

Arg Asp Asn
1

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Gly Phe Ser Phe Ser Ser Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic Construct

<400> SEQUENCE: 9

Gly Gly Arg
1

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Thr Gly Arg Val Tyr Phe Ala Leu Asp
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11
```

```
Ser Glu Ser Val Asp Thr Ser Asp Asn Ser Phe
1               5                   10
```

<210> SEQ ID NO 12
<211> LENGTH: 3
<212> TYPE: PRT
<213> ORGANISM: Artificial Sequence
<220> FEATURE:
<223> OTHER INFORMATION: Synthetic Construct

<400> SEQUENCE: 12

```
Arg Ser Ser
1
```

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

```
Asn Tyr Asp Val Pro Trp
1               5
```

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser
        115                 120
```

<210> SEQ ID NO 15
<211> LENGTH: 111
<212> TYPE: PRT
<213> ORGANISM: Artificial Sequence
<220> FEATURE:
<223> OTHER INFORMATION: Synthetic Construct

<400> SEQUENCE: 15

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gly Ser Val Asp Thr Ser
            20                  25                  30
```

Asp Asn Ser Phe Ile His Trp Tyr Gln Gln Lys Pro Gly Gln Ser Pro
            35                  40                  45

Lys Leu Leu Ile Tyr Arg Ser Ser Thr Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
             85                  90                  95

Asp Val Pro Trp Thr Phe Gly Gln Gly Thr Lys Val Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Synthetic Construct

<400> SEQUENCE: 16

Asp Val Val Met Thr Gln Ser Pro Leu Ser Leu Pro Val Thr Leu Gly
 1               5                  10                  15

Gln Pro Ala Ser Ile Ser Cys Arg Ala Ser Glu Ser Val Asp Thr Ser
             20                  25                  30

Asp Asn Ser Phe Ile His Trp Tyr Gln Gln Arg Pro Gly Gln Ser Pro
            35                  40                  45

Arg Leu Leu Ile Tyr Arg Ser Ser Thr Leu Glu Ser Gly Val Pro Asp
     50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Asn Tyr
             85                  90                  95

Asp Val Pro Trp Thr Phe Gly Gln Gly Thr Lys Val Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Synthetic Construct

<400> SEQUENCE: 17

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Thr Ser
             20                  25                  30

Asp Asn Ser Phe Ile His Trp Tyr Gln Gln Lys Pro Gly Gln Ser Pro
            35                  40                  45

Arg Leu Leu Ile Tyr Arg Ser Ser Thr Leu Glu Ser Gly Ile Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Asn Tyr
             85                  90                  95

Asp Val Pro Trp Thr Phe Gly Gln Gly Thr Lys Val Glu Ile Lys
            100                 105                 110

```
<210> SEQ ID NO 18
<211> LENGTH: 111
<212> TYPE: PRT
<213> ORGANISM: Artificial Sequence
<220> FEATURE:
<223> OTHER INFORMATION: Synthetic Construct

<400> SEQUENCE: 18
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Arg Leu Leu Ile Tyr Arg Ser Ser Thr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Asn Tyr
                85                  90                  95

Asp Val Pro Trp Thr Phe Gly Gln Gly Thr Lys Val Glu Ile Lys
            100                 105                 110

```
<210> SEQ ID NO 19
<211> LENGTH: 133
<212> TYPE: PRT
<213> ORGANISM: Homo sapiens

<400> SEQUENCE: 19
```

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

```
<210> SEQ ID NO 20
<211> LENGTH: 133
<212> TYPE: PRT
<213> ORGANISM: Artificial Sequence
<220> FEATURE:
<223> OTHER INFORMATION: Synthetic Construct

<400> SEQUENCE: 20
```

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys

```
            20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 597
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

```
Leu Gln Ser Ser Gly Leu Tyr Ser Leu Ser Val Val Thr Val Pro
                180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Cys Arg Asp Glu Leu Thr Lys Asn Gln Val Ser Leu
        355                 360                 365
Trp Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Gly Gly Gly Gly Ser Gly Gly Gly Ser Gly Gly Gly Gly Ser
450                 455                 460
Ala Pro Ala Ser Ser Ser Thr Lys Lys Thr Gln Leu Gln Leu Glu His
465                 470                 475                 480
Leu Leu Leu Asp Leu Gln Met Ile Leu Asn Gly Ile Asn Asn Tyr Lys
                485                 490                 495
Asn Pro Lys Leu Thr Arg Met Leu Thr Ala Lys Phe Ala Met Pro Lys
            500                 505                 510
Lys Ala Thr Glu Leu Lys His Leu Gln Cys Leu Glu Glu Glu Leu Lys
        515                 520                 525
Pro Leu Glu Glu Val Leu Asn Gly Ala Gln Ser Lys Asn Phe His Leu
        530                 535                 540
Arg Pro Arg Asp Leu Ile Ser Asn Ile Asn Val Ile Val Leu Glu Leu
545                 550                 555                 560
Lys Gly Ser Glu Thr Thr Phe Met Cys Glu Tyr Ala Asp Glu Thr Ala
                565                 570                 575
Thr Ile Val Glu Phe Leu Asn Arg Trp Ile Thr Phe Ala Gln Ser Ile
            580                 585                 590
Ile Ser Thr Leu Thr
```

<210> SEQ ID NO 23
<211> LENGTH: 448
<212> TYPE: PRT
<213> ORGANISM: Artificial Sequence
<220> FEATURE:
<223> OTHER INFORMATION: Synthetic Construct

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
```

```
            355                 360                 365
Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

<210> SEQ ID NO 24
<211> LENGTH: 448
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                        275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

<210> SEQ ID NO 25
<211> LENGTH: 218
<212> TYPE: PRT
<213> ORGANISM: Artificial Sequence
<220> FEATURE:
<223> OTHER INFORMATION: Synthetic Construct

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
```

```
                195                 200                 205
Val Thr Lys Ser Phe Asn Arg Gly Glu Cys
    210                 215

<210> SEQ ID NO 26
<211> LENGTH: 20
<212> TYPE: PRT
<213> ORGANISM: Homo sapiens

<400> SEQUENCE: 26

Met Tyr Arg Met Gln Leu Leu Ser Cys Ile Ala Leu Ser Leu Ala Leu
1               5                   10                  15

Val Thr Asn Ser
            20

<210> SEQ ID NO 27
<211> LENGTH: 268
<212> TYPE: PRT
<213> ORGANISM: Homo sapiens

<400> SEQUENCE: 27

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265
```

-continued

<210> SEQ ID NO 28
<211> LENGTH: 288
<212> TYPE: PRT
<213> ORGANISM: Homo sapiens

<400> SEQUENCE: 28

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 29
<211> LENGTH: 133
<212> TYPE: PRT
<213> ORGANISM: Artificial Sequence
<220> FEATURE:
<223> OTHER INFORMATION: Synthetic Construct

<400> SEQUENCE: 29

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

-continued

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 30
<211> LENGTH: 225
<212> TYPE: PRT
<213> ORGANISM: Homo sapiens

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 31
<211> LENGTH: 107
<212> TYPE: PRT
<213> ORGANISM: Homo sapiens

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 105
<212> TYPE: PRT
<213> ORGANISM: Homo sapiens

<400> SEQUENCE: 32

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65              70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 33
<211> LENGTH: 328
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 34
<211> LENGTH: 607
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140
```

```
Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Val Thr Val Pro Ser
        180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
        370                 375                 380

Ala Glu Asn Tyr Asp Asn Thr Gln Pro Ile Met Asp Thr Asp Gly Ser
385                 390                 395                 400

Tyr Phe Val Tyr Ser Asp Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Gly Gly Gly Gly Ser
        435                 440                 445

Gly Gly Gly Gly Ser Gly Gly Gly Ser Ala Pro Ala Ser Ser Ser
    450                 455                 460

Thr Ser Ser Ser Thr Ala Glu Ala Gln Gln Gln Gln Gln Gln Gln Gln
465                 470                 475                 480

Gln Gln Gln Gln His Leu Glu Gln Leu Leu Met Asp Leu Gln Glu Leu
                485                 490                 495

Leu Ser Arg Met Glu Asn Tyr Arg Asn Leu Lys Leu Pro Arg Met Leu
            500                 505                 510

Thr Ala Lys Phe Ala Leu Pro Lys Gln Ala Thr Glu Leu Lys Asp Leu
            515                 520                 525

Gln Cys Leu Glu Asp Glu Leu Gly Pro Leu Arg His Val Leu Asp Gly
            530                 535                 540

Thr Gln Ser Lys Ser Phe Gln Leu Glu Asp Ala Glu Asn Phe Ile Ser
545                 550                 555                 560
```

```
Asn Ile Arg Val Thr Val Lys Leu Lys Gly Ser Asp Asn Thr Phe
                565                 570                 575

Glu Cys Gln Phe Asp Asp Glu Ser Ala Thr Val Val Asp Phe Leu Arg
            580                 585                 590

Arg Trp Ile Ala Phe Ala Gln Ser Ile Ile Ser Thr Ser Pro Gln
        595                 600                 605
```

<210> SEQ ID NO 35
<211> LENGTH: 442
<212> TYPE: PRT
<213> ORGANISM: Artificial Sequence
<220> FEATURE:
<223> OTHER INFORMATION: Synthetic Construct

<400> SEQUENCE: 35

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320
```

```
Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Lys Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Lys Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro
        435                 440
```

<210> SEQ ID NO 36
<211> LENGTH: 218
<212> TYPE: PRT
<213> ORGANISM: Artificial Sequence
<220> FEATURE:
<223> OTHER INFORMATION: Synthetic Construct

<400> SEQUENCE: 36

```
Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Gly Thr Lys Leu Glu Leu Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 37
<211> LENGTH: 595

```
<212> TYPE: PRT
<213> ORGANISM: Artificial Sequence
<220> FEATURE:
<223> OTHER INFORMATION: Synthetic Construct

<400> SEQUENCE: 37
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Ser |
| | | | 20 | | | | | 25 | | | | | 30 | | |
| Trp | Ile | His | Trp | Val | Arg | Gln | Ala | Pro | Gly | Lys | Gly | Leu | Glu | Trp | Val |
| | | 35 | | | | | 40 | | | | | 45 | | | |
| Ala | Trp | Ile | Ser | Pro | Tyr | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | His | Trp | Pro | Gly | Gly | Phe | Asp | Tyr | Trp | Gly | Gln | Gly | Thr |
| | | | 100 | | | | | 105 | | | | | 110 | | |
| Leu | Val | Thr | Val | Ser | Ala | Ala | Ser | Thr | Lys | Gly | Pro | Ser | Val | Phe | Pro |
| | | | 115 | | | | | 120 | | | | | 125 | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Ala | Ala | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | | 275 | | | | | 280 | | | | | 285 | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Gly | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Cys | Arg | Asp | Glu | Leu | Thr | Lys | Asn | Gln | Val | Ser | Leu | Trp | Cys |
| | | | 355 | | | | | 360 | | | | | 365 | | |
| Leu | Val | Lys | Gly | Phe | Tyr | Pro | Ser | Asp | Ile | Ala | Val | Glu | Trp | Glu | Ser |
| | | | 370 | | | | | 375 | | | | | 380 | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Gly
            435                 440                 445

Gly Gly Gly Ser Gly Gly Gly Ser Gly Gly Gly Ser Ala Pro
    450                 455                 460

Ala Ser Ser Thr Lys Lys Thr Gln Leu Gln Leu Glu His Leu Leu
465             470                 475                 480

Leu Asp Leu Gln Met Ile Leu Asn Gly Ile Asn Asn Tyr Lys Asn Pro
                485                 490                 495

Lys Leu Thr Arg Met Leu Thr Ala Lys Phe Ala Met Pro Lys Lys Ala
            500                 505                 510

Thr Glu Leu Lys His Leu Gln Cys Leu Glu Glu Glu Leu Lys Pro Leu
            515                 520                 525

Glu Glu Val Leu Asn Gly Ala Gln Ser Lys Asn Phe His Leu Arg Pro
        530                 535                 540

Arg Asp Leu Ile Ser Asn Ile Asn Val Ile Val Leu Glu Leu Lys Gly
545             550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Ala Gln Ser Ile Ile Ser
            580                 585                 590

Thr Leu Thr
        595

<210> SEQ ID NO 38
<211> LENGTH: 446
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro
        435                 440                 445

<210> SEQ ID NO 39
<211> LENGTH: 214
<212> TYPE: PRT
<213> ORGANISM: Artificial Sequence
<220> FEATURE:
<223> OTHER INFORMATION: Synthetic Construct

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 605
<212> TYPE: PRT
<213> ORGANISM: Artificial Sequence
<220> FEATURE:
<223> OTHER INFORMATION: Synthetic Construct

<400> SEQUENCE: 40

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
             20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205
```

```
Thr Lys Val Asp Lys Lys Ile Val Pro Arg Asp Cys Gly Cys Lys Pro
    210                 215                 220
Cys Ile Cys Thr Val Pro Glu Val Ser Ser Val Phe Ile Phe Pro Pro
225                 230                 235                 240
Lys Pro Lys Asp Val Leu Thr Ile Thr Leu Thr Pro Lys Val Thr Cys
                245                 250                 255
Val Val Val Ala Ile Ser Lys Asp Asp Pro Glu Val Gln Phe Ser Trp
            260                 265                 270
Phe Val Asp Asp Val Glu Val His Thr Ala Gln Thr Gln Pro Arg Glu
        275                 280                 285
Glu Gln Phe Asn Ser Thr Phe Arg Ser Val Ser Glu Leu Pro Ile Met
290                 295                 300
His Gln Asp Trp Leu Asn Gly Lys Glu Phe Lys Cys Arg Val Asn Ser
305                 310                 315                 320
Ala Ala Phe Gly Ala Pro Ile Glu Lys Thr Ile Ser Lys Thr Lys Gly
                325                 330                 335
Arg Pro Lys Ala Pro Gln Val Tyr Thr Ile Pro Pro Lys Glu Gln
            340                 345                 350
Met Ala Lys Asp Lys Val Ser Leu Thr Cys Met Ile Thr Asp Phe Phe
        355                 360                 365
Pro Glu Asp Ile Thr Val Glu Trp Gln Trp Asn Gly Gln Pro Ala Glu
370                 375                 380
Asn Tyr Asp Asn Thr Gln Pro Ile Met Asp Thr Asp Gly Ser Tyr Phe
385                 390                 395                 400
Val Tyr Ser Asp Leu Asn Val Gln Lys Ser Asn Trp Glu Ala Gly Asn
                405                 410                 415
Thr Phe Thr Cys Ser Val Leu His Glu Gly Leu His Asn His His Thr
            420                 425                 430
Glu Lys Ser Leu Ser His Ser Pro Gly Gly Gly Gly Ser Gly Gly
        435                 440                 445
Gly Gly Ser Gly Gly Gly Ser Ala Pro Ala Ser Ser Thr Ser
    450                 455                 460
Ser Ser Thr Ala Glu Ala Gln Gln Gln Gln Gln Gln Gln Gln Gln
465                 470                 475                 480
Gln Gln His Leu Glu Gln Leu Leu Met Asp Leu Gln Glu Leu Leu Ser
            485                 490                 495
Arg Met Glu Asn Tyr Arg Asn Leu Lys Leu Pro Arg Met Leu Thr Ala
        500                 505                 510
Lys Phe Ala Leu Pro Lys Gln Ala Thr Glu Leu Lys Asp Leu Gln Cys
        515                 520                 525
Leu Glu Asp Glu Leu Gly Pro Leu Arg His Val Leu Asp Gly Thr Gln
530                 535                 540
Ser Lys Ser Phe Gln Leu Glu Asp Ala Glu Asn Phe Ile Ser Asn Ile
545                 550                 555                 560
Arg Val Thr Val Val Lys Leu Lys Gly Ser Asp Asn Thr Phe Glu Cys
                565                 570                 575
Gln Phe Asp Asp Glu Ser Ala Thr Val Val Asp Phe Leu Arg Arg Trp
            580                 585                 590
Ile Ala Phe Ala Gln Ser Ile Ile Ser Thr Ser Pro Gln
        595                 600                 605

<210> SEQ ID NO 41
<211> LENGTH: 440
<212> TYPE: PRT
```

<213> ORGANISM: Artificial Sequence
<220> FEATURE:
<223> OTHER INFORMATION: Synthetic Construct

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Ala Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Gly Ala Pro Ile Glu Lys Thr Ile Ser Lys Thr Lys Gly
                325                 330                 335

Arg Pro Lys Ala Pro Gln Val Tyr Thr Ile Pro Pro Pro Lys Lys Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Lys Thr Asp Gly Ser Tyr Phe
```

```
                385                 390                 395                 400
Val Tyr Ser Lys Leu Asn Val Gln Lys Ser Asn Trp Glu Ala Gly Asn
                    405                 410                 415

Thr Phe Thr Cys Ser Val Leu His Glu Gly Leu His Asn His His Thr
                420                 425                 430

Glu Lys Ser Leu Ser His Ser Pro
                435                 440

<210> SEQ ID NO 42
<211> LENGTH: 214
<212> TYPE: PRT
<213> ORGANISM: Artificial Sequence
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 43
<211> LENGTH: 150
<212> TYPE: PRT
<213> ORGANISM: Homo sapiens

<400> SEQUENCE: 43

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45
```

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 44
<211> LENGTH: 608
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Gln Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

```
Val Thr Cys Val Val Ala Ile Ser Lys Asp Asp Pro Glu Val Gln
            260                 265                 270

Phe Ser Trp Phe Val Asp Asp Val Glu Val His Thr Ala Gln Thr Lys
        275                 280                 285

Pro Arg Glu Glu Gln Ile Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Gly Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asn Phe Phe Pro Glu Asp Ile Thr Val Glu Trp Gln Trp Asn Gly Gln
    370                 375                 380

Pro Ala Glu Asn Tyr Asp Asn Thr Gln Pro Ile Met Asp Thr Asp Gly
385                 390                 395                 400

Ser Tyr Phe Val Tyr Ser Asp Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Gly Gly Gly Gly
        435                 440                 445

Ser Gly Gly Gly Gly Ser Gly Gly Gly Ser Pro Ala Ser Ser
    450                 455                 460

Ser Thr Ser Ser Ser Thr Ala Glu Ala Gln Gln Gln Gln Gln Gln Gln
465                 470                 475                 480

Gln Gln Gln Gln Gln His Leu Glu Gln Leu Leu Met Asp Leu Gln Glu
                485                 490                 495

Leu Leu Ser Arg Met Glu Asn Tyr Arg Asn Leu Lys Leu Pro Arg Met
            500                 505                 510

Leu Thr Ala Lys Phe Ala Leu Pro Lys Gln Ala Thr Glu Leu Lys Asp
        515                 520                 525

Leu Gln Cys Leu Glu Asp Glu Leu Gly Pro Leu Arg His Val Leu Asp
    530                 535                 540

Gly Thr Gln Ser Lys Ser Phe Gln Leu Glu Asp Ala Glu Asn Phe Ile
545                 550                 555                 560

Ser Asn Ile Arg Val Thr Val Val Lys Leu Lys Gly Ser Asp Asn Thr
                565                 570                 575

Phe Glu Cys Gln Phe Asp Asp Glu Ser Ala Thr Val Val Asp Phe Leu
            580                 585                 590

Arg Arg Trp Ile Ala Phe Ala Gln Ser Ile Ile Ser Thr Ser Pro Gln
        595                 600                 605

<210> SEQ ID NO 45
<211> LENGTH: 445
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
        35                  40                  45
Gly Trp Ile Asn Thr Lys Thr Gly Glu Ala Thr Tyr Val Glu Glu Phe
50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
            100                 105                 110
Gln Gly Thr Thr Val Thr Val Ser Ser Ala Lys Thr Thr Pro Pro Ser
        115                 120                 125
Val Tyr Pro Leu Ala Pro Gly Ser Ala Ala Gln Thr Asn Ser Met Val
    130                 135                 140
Thr Leu Gly Cys Leu Val Lys Gly Tyr Phe Pro Glu Pro Val Thr Val
145                 150                 155                 160
Thr Trp Asn Ser Gly Ser Leu Ser Ser Gly Val His Thr Phe Pro Ala
                165                 170                 175
Val Leu Gln Ser Asp Leu Tyr Thr Leu Ser Ser Ser Val Thr Val Pro
            180                 185                 190
Ser Ser Thr Trp Pro Ser Gln Thr Val Thr Cys Asn Val Ala His Pro
        195                 200                 205
Ala Ser Ser Thr Lys Val Asp Lys Lys Ile Val Pro Arg Asp Cys Gly
    210                 215                 220
Cys Lys Pro Cys Ile Cys Thr Val Pro Glu Val Ser Ser Val Phe Ile
225                 230                 235                 240
Phe Pro Pro Lys Pro Lys Asp Val Leu Thr Ile Thr Leu Thr Pro Lys
                245                 250                 255
Val Thr Cys Val Val Val Ala Ile Ser Lys Asp Asp Pro Glu Val Gln
            260                 265                 270
Phe Ser Trp Phe Val Asp Asp Val Glu Val His Thr Ala Gln Thr Lys
        275                 280                 285
Pro Arg Glu Glu Gln Ile Asn Ser Thr Phe Arg Ser Val Ser Glu Leu
    290                 295                 300
Pro Ile Met His Gln Asp Trp Leu Asn Gly Lys Glu Phe Lys Cys Arg
305                 310                 315                 320
Val Asn Ser Ala Ala Phe Gly Ala Pro Ile Glu Lys Thr Ile Ser Lys
                325                 330                 335
Thr Lys Gly Arg Pro Lys Ala Pro Gln Val Tyr Thr Ile Pro Pro Pro
            340                 345                 350
Lys Lys Gln Met Ala Lys Asp Lys Val Ser Leu Thr Cys Met Ile Thr
        355                 360                 365
Asn Phe Phe Pro Glu Asp Ile Thr Val Glu Trp Gln Trp Asn Gly Gln
    370                 375                 380
Pro Ala Glu Asn Tyr Lys Asn Thr Gln Pro Ile Met Lys Thr Asp Gly
385                 390                 395                 400
Ser Tyr Phe Val Tyr Ser Lys Leu Asn Val Gln Lys Ser Asn Trp Glu
                405                 410                 415
Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 46
<211> LENGTH: 215
<212> TYPE: PRT
<213> ORGANISM: Artificial Sequence
<220> FEATURE:
<223> OTHER INFORMATION: Synthetic Construct

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
210                 215

<210> SEQ ID NO 47
<211> LENGTH: 604
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                    85                  90                  95

Ala Lys Gly Trp Phe Gly Gly Phe Asn Tyr Trp Gly Gln Gly Thr Leu
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Ala Ile Ser Lys Asp Asp Pro Glu Val Gln Phe Ser Trp Phe
            260                 265                 270

Val Asp Asp Val Glu Val His Thr Ala Gln Thr Lys Pro Arg Glu Glu
        275                 280                 285

Gln Ile Asn Ser Thr Phe Arg Ser Val Ser Glu Leu Pro Ile Met His
290                 295                 300

Gln Asp Trp Leu Asn Gly Lys Glu Phe Lys Cys Arg Val Asn Ser Ala
305                 310                 315                 320

Ala Phe Gly Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asn Phe Phe Pro
        355                 360                 365

Glu Asp Ile Thr Val Glu Trp Gln Trp Asn Gly Gln Pro Ala Glu Asn
370                 375                 380

Tyr Asp Asn Thr Gln Pro Ile Met Asp Thr Asp Gly Ser Tyr Phe Val
385                 390                 395                 400

Tyr Ser Asp Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Gly Gly Gly Ser Gly Gly
        435                 440                 445

Gly Ser Gly Gly Gly Ser Ala Pro Ala Ser Ser Ser Thr Ser Ser
    450                 455                 460

Ser Thr Ala Glu Ala Gln Gln Gln Gln Gln Gln Gln Gln Gln
465                 470                 475                 480

Gln His Leu Glu Gln Leu Leu Met Asp Leu Gln Glu Leu Leu Ser Arg
                485                 490                 495
```

```
Met Glu Asn Tyr Arg Asn Leu Lys Leu Pro Arg Met Leu Thr Ala Lys
                500                 505                 510

Phe Ala Leu Pro Lys Gln Ala Thr Glu Leu Lys Asp Leu Gln Cys Leu
            515                 520                 525

Glu Asp Glu Leu Gly Pro Leu Arg His Val Leu Asp Gly Thr Gln Ser
        530                 535                 540

Lys Ser Phe Gln Leu Glu Asp Ala Glu Asn Phe Ile Ser Asn Ile Arg
545                 550                 555                 560

Val Thr Val Val Lys Leu Lys Gly Ser Asp Asn Thr Phe Glu Cys Gln
                565                 570                 575

Phe Asp Asp Glu Ser Ala Thr Val Val Asp Phe Leu Arg Arg Trp Ile
            580                 585                 590

Ala Phe Ala Gln Ser Ile Ile Ser Thr Ser Pro Gln
        595                 600

<210> SEQ ID NO 48
<211> LENGTH: 441
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255
```

```
Val Val Ala Ile Ser Lys Asp Asp Pro Glu Val Gln Phe Ser Trp Phe
            260                 265                 270

Val Asp Asp Val Glu Val His Thr Ala Gln Thr Lys Pro Arg Glu Glu
        275                 280                 285

Gln Ile Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Gly Ala Pro Ile Glu Lys Thr Ile Ser Lys Thr Lys Gly Arg
                325                 330                 335

Pro Lys Ala Pro Gln Val Tyr Thr Ile Pro Pro Lys Lys Gln Met
                340                 345                 350

Ala Lys Asp Lys Val Ser Leu Thr Cys Met Ile Thr Asn Phe Phe Pro
            355                 360                 365

Glu Asp Ile Thr Val Glu Trp Gln Trp Asn Gly Gln Pro Ala Glu Asn
        370                 375                 380

Tyr Lys Asn Thr Gln Pro Ile Met Lys Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
            435                 440

<210> SEQ ID NO 49
<211> LENGTH: 215
<212> TYPE: PRT
<213> ORGANISM: Artificial Sequence
<220> FEATURE:
<223> OTHER INFORMATION: Synthetic Construct

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175
```

```
Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 50
<211> LENGTH: 450
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Gln Glu Ser Gly Pro Gly Leu Val Lys Pro Ser Gln
1               5                  10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Ser Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Ala Ala Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320
```

```
Glu Phe Lys Cys Lys Val Asn Asn Lys Asp Leu Gly Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 51
<211> LENGTH: 218
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Thr Lys Leu Glu Leu Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

IMMUNOCONJUGATES

CROSS REFERENCE TO RELATED APPLICATIONS

This application is a divisional of U.S. application Ser. No. 15/943,237, filed Apr. 2, 2018, now U.S. Pat. No. 11,413,331, which claims benefit of priority to European Application No. EP 17164533.6, filed Apr. 3, 2017, each of which is incorporated herein by reference in their entirety.

SEQUENCE LISTING

The instant application contains a Sequence Listing with 51 sequences, is submitted electronically in ASCII format and is hereby incorporated herein by reference in its entirety. Said ASCII copy, created Jun. 24, 2022, is named P34189-US-1_Sequence_listing.txt and is 101,381 bytes in size.

FIELD OF THE INVENTION

The present invention generally relates to immunoconjugates, particularly immunoconjugates comprising a mutant interleukin-2 polypeptide and an antibody that binds to PD-1. In addition, the invention relates to polynucleotide molecules encoding the immunoconjugates, and vectors and host cells comprising such polynucleotide molecules. The invention further relates to methods for producing the mutant immunoconjugates, pharmaceutical compositions comprising the same, and uses thereof.

BACKGROUND

Interleukin-2 (IL-2), also known as T cell growth factor (TCGF), is a 15.5 kDa globular glycoprotein playing a central role in lymphocyte generation, survival and homeostasis. It has a length of 133 amino acids and consists of four antiparallel, amphipatic α-helices that form a quaternary structure indispensable of its function (Smith, Science 240, 1169-76 (1988); Bazan, Science 257, 410-413 (1992)). Sequences of IL-2 from different species are found under NCBI RefSeq Nos. NP000577 (human), NP032392 (mouse), NP446288 (rat) or NP517425 (chimpanzee).

IL-2 mediates its action by binding to IL-2 receptors (IL-2R), which consist of up to three individual subunits, the different association of which can produce receptor forms that differ in their affinity to IL-2. Association of the α (CD25), β (CD122), and γ ($γ_c$, CD132) subunits results in a trimeric, high-affinity receptor for IL-2. Dimeric IL-2 receptor consisting of the α and γ subunits is termed intermediate-affinity IL-2R. The α subunit forms the monomeric low affinity IL-2 receptor. Although the dimeric intermediate-affinity IL-2 receptor binds IL-2 with approximately 100-fold lower affinity than the trimeric high-affinity receptor, both the dimeric and the trimeric IL-2 receptor variants are able to transmit signal upon IL-2 binding (Minami et al., Annu Rev Immunol 11, 245-268 (1993)). Hence, the α-subunit, CD25, is not essential for IL-2 signalling. It confers high-affinity binding to its receptor, whereas the β subunit, CD122, and the γ-subunit are crucial for signal transduction (Krieg et al., Proc Natl Acad Sci 107, 11906-11 (2010)). Trimeric IL-2 receptors including CD25 are expressed by (resting) CD4$^+$ forkhead box P3 (FoxP3)$^+$ regulatory T ($T_{reg}$) cells. They are also transiently induced on conventional activated T cells, whereas in the resting state these cells express only dimeric IL-2 receptors. $T_{reg}$ cells consistently express the highest level of CD25 in vivo (Fontenot et al., Nature Immunol 6, 1142-51 (2005)).

IL-2 is synthesized mainly by activated T-cells, in particular CD4$^+$ helper T cells. It stimulates the proliferation and differentiation of T cells, induces the generation of cytotoxic T lymphocytes (CTLs) and the differentiation of peripheral blood lymphocytes to cytotoxic cells and lymphokine-activated killer (LAK) cells, promotes cytokine and cytolytic molecule expression by T cells, facilitates the proliferation and differentiation of B-cells and the synthesis of immunoglobulin by B-cells, and stimulates the generation, proliferation and activation of natural killer (NK) cells (reviewed e.g. in Waldmann, Nat Rev Immunol 6, 595-601 (2009); Olejniczak and Kasprzak, Med Sci Monit 14, RA179-89 (2008); Malek, Annu Rev Immunol 26, 453-79 (2008)).

Its ability to expand lymphocyte populations in vivo and to increase the effector functions of these cells confers antitumor effects to IL-2, making IL-2 immunotherapy an attractive treatment option for certain metastatic cancers. Consequently, high-dose IL-2 treatment has been approved for use in patients with metastatic renal-cell carcinoma and malignant melanoma.

However, IL-2 has a dual function in the immune response in that it not only mediates expansion and activity of effector cells, but also is crucially involved in maintaining peripheral immune tolerance.

A major mechanism underlying peripheral self-tolerance is IL-2 induced activation-induced cell death (AICD) in T cells. AICD is a process by which fully activated T cells undergo programmed cell death through engagement of cell surface-expressed death receptors such as CD95 (also known as Fas) or the TNF receptor. When antigen-activated T cells expressing a high-affinity IL-2 receptor (after previous exposure to IL-2) during proliferation are re-stimulated with antigen via the T cell receptor (TCR)/CD3 complex, the expression of Fas ligand (FasL) and/or tumor necrosis factor (TNF) is induced, making the cells susceptible for Fas-mediated apoptosis. This process is IL-2 dependent (Lenardo, Nature 353, 858-61 (1991)) and mediated via STAT5. By the process of AICD in T lymphocytes tolerance can not only be established to self-antigens, but also to persistent antigens that are clearly not part of the host's makeup, such as tumor antigens.

Moreover, IL-2 is also involved in the maintenance of peripheral CD4$^+$CD25$^+$ regulatory T ($T_{reg}$) cells (Fontenot et al., Nature Immunol 6, 1142-51 (2005); D'Cruz and Klein, Nature Immunol 6, 1152-59 (2005); Maloy and Powrie, Nature Immunol 6, 1171-72 (2005), which are also known as suppressor T cells. They suppress effector T cells from destroying their (self-)target, either through cell-cell contact by inhibiting T cell help and activation, or through release of immunosuppressive cytokines such as IL-10 or TGF-β. Depletion of $T_{reg}$ cells was shown to enhance IL-2 induced anti-tumor immunity (Imai et al., Cancer Sci 98, 416-23 (2007)).

Therefore, IL-2 is not optimal for inhibiting tumor growth, because in the presence of IL-2 either the CTLs generated might recognize the tumor as self and undergo AICD or the immune response might be inhibited by IL-2 dependent $T_{reg}$ cells.

A further concern in relation to IL-2 immunotherapy are the side effects produced by recombinant human IL-2 treatment. Patients receiving high-dose IL-2 treatment frequently experience severe cardiovascular, pulmonary, renal, hepatic, gastrointestinal, neurological, cutaneous, haematological and systemic adverse events, which require intensive monitoring and in-patient management. The majority of these side effects can be explained by the development of so-called vascular (or capillary) leak syndrome (VLS), a pathological increase in vascular permeability leading to fluid extravasation in multiple organs (causing e.g. pulmonary and cutaneous edema and liver cell damage) and intravascular fluid depletion (causing a drop in blood pressure and compensatory increase in heart rate). There is no treatment of VLS other than withdrawal of IL-2. Low-dose IL-2 regimens have been tested in patients to avoid VLS, however, at the expense of suboptimal therapeutic results. VLS was believed to be caused by the release of proinflammatory cytokines, such as tumor necrosis factor (TNF)-$\alpha$ from IL-2-activated NK cells, however it has recently been shown that IL-2-induced pulmonary edema resulted from direct binding of IL-2 to lung endothelial cells, which expressed low to intermediate levels of functional $\alpha\beta\gamma$ IL-2 receptors (Krieg et al., Proc Nat Acad Sci USA 107, 11906-11 (2010)).

Several approaches have been taken to overcome these problems associated with IL-2 immunotherapy. For example, it has been found that the combination of IL-2 with certain anti-IL-2 monoclonal antibodies enhances treatment effects of IL-2 in vivo (Kamimura et al., J Immunol 177, 306-14 (2006); Boyman et al., Science 311, 1924-27 (2006)). In an alternative approach, IL-2 has been mutated in various ways to reduce its toxicity and/or increase its efficacy. Hu et al. (Blood 101, 4853-4861 (2003), US Pat. Publ. No. 2003/0124678) have substituted the arginine residue in position 38 of IL-2 by tryptophan to eliminate IL-2's vasopermeability activity. Shanafelt et al. (Nature Biotechnol 18, 1197-1202 (2000)) have mutated asparagine 88 to arginine to enhance selectivity for T cells over NK cells. Heaton et al. (Cancer Res 53, 2597-602 (1993); U.S. Pat. No. 5,229,109) have introduced two mutations, Arg38Ala and Phe42Lys, to reduce the secretion of proinflammatory cytokines from NK cells. Gillies et al. (US Pat. Publ. No. 2007/0036752) have substituted three residues of IL-2 (Asp20Thr, Asn88Arg, and Gln126Asp) that contribute to affinity for the intermediate-affinity IL-2 receptor to reduce VLS. Gillies et al. (WO 2008/0034473) have also mutated the interface of IL-2 with CD25 by amino acid substitution Arg38Trp and Phe42Lys to reduce interaction with CD25 and activation of $T_{reg}$ cells for enhancing efficacy. To the same aim, Wittrup et al. (WO 2009/061853) have produced IL-2 mutants that have enhanced affinity to CD25, but do not activate the receptor, thus act as antagonists. The mutations introduced were aimed at disrupting the interaction with the $\beta$- and/or $\gamma$-subunit of the receptor.

A particular mutant IL-2 polypeptide, designed to overcome the above-mentioned problems associated with IL-2 immunotherapy (toxicity caused by the induction of VLS, tumor tolerance caused by the induction of AICD, and immunosuppression caused by activation of $T_{reg}$ cells), is described in WO 2012/107417. Substitution of the phenylalanine residue at position 42 by alanine, the tyrosine residue at position 45 by alanine and the leucine residue at position 72 of IL-2 by glycine essentially abolishes binding of this mutant IL-2 polypeptide to the $\alpha$-subunit of the IL-2 receptor (CD25).

Further to the above-mentioned approaches, IL-2 immunotherapy may be improved by selectively targeting IL-2 to tumors, e.g. in the form of immunoconjugates comprising an antibody that binds to an antigen expressed on tumor cells. Several such immunoconjugates have been described (see e.g. Ko et al., J Immunother (2004) 27, 232-239; Klein et al., Oncoimmunology (2017) 6(3), e1277306).

Tumors may be able, however, to escape such targeting by shedding, mutating or downregulating the target antigen of the antibody. Moreover, tumor-targeted IL-2 may not come into optimal contact with effector cells such as cytotoxic T lymphocytes (CTLs), in tumor microenvironments that actively exclude lymphocytes.

Thus there remains a need to further improve IL-2 immunotherapy. An approach, which may circumvent the problems of tumor-targeting, is to target IL-2 directly to effector cells, in particular CTLs.

Ghasemi et al. have described a fusion protein of IL-2 and an NKG2D binding protein (Ghashemi et al., Nat Comm (2016) 7, 12878), for targeting IL-2 to NKG2D-bearing cells such as natural killer (NK) cells.

Programmed cell death protein 1 (PD-1 or CD279) is an inhibitory member of the CD28 family of receptors, that also includes CD28, CTLA-4, ICOS and BTLA. PD-1 is a cell surface receptor and is expressed on activated B cells, T cells, and myeloid cells (Okazaki et al (2002) Curr. Opin. Immunol. 14: 391779-82; Bennett et al. (2003) J Immunol 170:711-8). The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Two ligands for PD-1 have been identified, PD-L1 and PD-L2, that have been shown to downregulate T cell activation upon binding to PD-1 (Freeman et al (2000) J Exp Med 192: 1027-34; Latchman et al (2001) Nat Immunol 2:261-8; Carter etal (2002) Eur J Immunol 32:634-43). Both PD-L1 and PD-L2 are B7 homologs that bind to PD-1, but do not bind to other CD28 family members. One ligand for PD-1, PD-L1 is abundant in a variety of human cancers (Dong et al (2002) Nat. Med 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. MoI. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat 7. Acad. ScL USA 99: 12293-7; Brown et al. (2003) J. Immunol. 170:1257-66).

Antibodies that bind to PD-1 are described e.g. PCT patent application no. PCT/EP2016/073248.

SUMMARY OF THE INVENTION

The present invention provides a novel approach of targeting a mutant form of IL-2 with advantageous properties for immunotherapy directly to immune effector cells, such as cytotoxic T lymphocytes, rather than tumor cells. Targeting to immune effector cells is achieved by conjugation of the mutant IL-2 molecule to an antibody that binds to PD-1.

The IL-2 mutant used in the present invention has been designed to overcome the problems associated with IL-2 immunotherapy, in particular toxicity caused by the induction of VLS, tumor tolerance caused by the induction of AICD, and immunosuppression caused by activation of $T_{reg}$ cells. In addition to circumventing escape of tumors from tumor-targeting as mentioned above, targeting of the IL-2 mutant to immune effector cells may further increase the preferential activation of CTLs over immunosuppressive $T_{reg}$ cells. By using an antibody that binds to PD-1, the suppression of T-cell activity induced by the interaction of PD-1 with its ligand PD-L1 may additionally be reversed, thus further enhancing the immune response.

An IL-2 fusion protein comprising the anti-PD-L1 antibody atezolizumab has been described by Chen et al. (Chen et al., Biochem Biophys Res Comm (2016) 480, 160-165).

Of note, the immunoconjugate of the invention, comprising an antibody that binds to PD-1, shows significantly superior anti-tumor efficacy in vivo as compared to a similar immunoconjugate targeting PD-L1 (see Example 3 hereinbelow).

In a general aspect, the invention provides an immunoconjugate comprising an antibody that binds to PD-1 and a polypeptide that signals through IL-2Rβγ. The polypeptide signaling through IL-2Rβγ is particularly an IL-2 polypeptide or an IL-15 polypeptide. In a first aspect, the invention provides an immunoconjugate comprising a mutant IL-2 polypeptide and an antibody that binds to PD-1, wherein the mutant IL-2 polypeptide is a human IL-2 molecule comprising the amino acid substitutions F42A, Y45A and L72G (numbering relative to the human IL-2 sequence SEQ ID NO: 19).

In a further aspect, the invention provides an immunoconjugate comprising a mutant IL-2 polypeptide and an antibody that binds to PD-1, wherein the mutant IL-2 polypeptide is a human IL-2 molecule comprising the amino acid substitutions F42A, Y45A and L72G (numbering relative to the human IL-2 sequence SEQ ID NO: 19); and wherein the antibody comprises (a) a heavy chain variable region (VH) comprising a HVR-H1 comprising the amino acid sequence of SEQ ID NO:1, a HVR-H2 comprising the amino acid sequence of SEQ ID NO:2, a HVR-H3 comprising the amino acid sequence of SEQ ID NO:3, and a FR-H3 comprising the amino acid sequence of SEQ ID NO:7 at positions 71-73 according to Kabat numbering, and (b) a light chain variable region (VL) comprising a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:6, or wherein the antibody comprises (a) a heavy chain variable region (VH) comprising a HVR-H1 comprising the amino acid sequence of SEQ ID NO:8, a HVR-H2 comprising the amino acid sequence of SEQ ID NO:9, and a HVR-H3 comprising the amino acid sequence of SEQ ID NO:10, and (b) a light chain variable region (VL) comprising a HVR-L1 comprising the amino acid sequence of SEQ ID NO:11, a HVR-L2 comprising the amino acid sequence of SEQ ID NO:12, and a HVR-L3 comprising the amino acid sequence of SEQ ID NO:13.

In another aspect, the invention provides an immunoconjugate comprising a mutant IL-2 polypeptide and an antibody that binds to PD-1, wherein the mutant IL-2 polypeptide is a human IL-2 molecule comprising the amino acid substitutions F42A, Y45A and L72G (numbering relative to the human IL-2 sequence SEQ ID NO: 19); and wherein the antibody comprises (a) a heavy chain variable region (VH) comprising an amino acid sequence that is at least about 95%, 96%, 97%, 98%, 99% or 100% identical to the amino acid sequence of SEQ ID NO:14, and (b) a light chain variable region (VL) comprising an amino acid sequence that is at least about 95%, 96%, 97%, 98%, 99% or 100% identical to an amino acid sequence selected from the group consisting of SEQ ID NO:15, SEQ ID NO:16, SEQ ID NO: 17, and SEQ ID NO:18.

In some embodiments of the immunoconjugate according to the invention, the mutant IL-2 polypeptide further comprises the amino acid substitution T3A and/or the amino acid substitution C125A. In some embodiments, the mutant IL-2 polypeptide comprises the sequence of SEQ ID NO: 20. In some embodiments, the immunoconjugate comprises not more than one mutant IL-2 polypeptide. In some embodiments, the antibody comprises an Fc domain composed of a first and a second subunit. In some such embodiments, the Fc domain is an IgG class, particularly an IgG$_1$ subclass, Fc domain, and/or the Fc domain is a human Fc domain. In some embodiments, the antibody is an IgG class, particularly an IgG$_1$ subclass immunoglobulin.

In some embodiments wherein the immunoconjugate comprises an Fc domain, the Fc domain comprises a modification promoting the association of the first and the second subunit of the Fc domain. In some embodiments, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. In some embodiments, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index). In some such embodiments, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index). In some embodiments, the mutant IL-2 polypeptide is fused at its amino-terminal amino acid to the carboxy-terminal amino acid of one of the subunits of the Fc domain, particularly the first subunit of the Fc domain, optionally through a linker peptide. In some such embodiments, the linker peptide has the amino acid sequence of SEQ ID NO:21.

In some embodiments wherein the immunoconjugate comprises an Fc domain, the Fc domain comprises one or more amino acid substitution that reduces binding to an Fc receptor, particularly an Fcγ receptor, and/or effector function, particularly antibody-dependent cell-mediated cytotoxicity (ADCC). In some such embodiments, said one or more amino acid substitution is at one or more position selected from the group of L234, L235, and P329 (Kabat EU index numbering). In some embodiments, each subunit of the Fc domain comprises the amino acid substitutions L234A, L235A and P329G (Kabat EU index numbering).

In some embodiments, the immunoconjugate according to the invention comprises a polypeptide comprising an amino acid sequence that is at least about 80%, 85%, 90%, 95%, 96%, 97%, 98%, 99% or 100% identical to the sequence of SEQ ID NO:22, a polypeptide comprising an amino acid sequence that is at least about 80%, 85%, 90%, 95%, 96%, 97%, 98%, 99% or 100% identical to the sequence of SEQ ID NO:23 or SEQ ID NO:24, and a polypeptide comprising an amino acid sequence that is at least about 80%, 85%, 90%, 95%, 96%, 97%, 98%, 99% or 100% identical to the sequence of SEQ ID NO:25. In some embodiments, the immunoconjugate essentially consists of a mutant IL-2 polypeptide and an IgG$_1$ immunoglobulin molecule, joined by a linker sequence.

The invention further provides one or more isolated polynucleotide encoding an immunoconjugate of the invention, one or more vector (particularly expression vector) comprising said polynucleotides, and host cells comprising said polynucleotide(s) or said vector(s).

Also provided is a method of producing an immunoconjugate comprising a mutant IL-2 polypeptide and an antibody that binds to PD-1, comprising (a) culturing the host cell of the invention under conditions suitable for the expression of the immunoconjugate, and optionally (b) recovering the immunoconjugate. Also provided by the invention is an immunoconjugate comprising a mutant IL-2 polypeptide and an antibody that binds to PD-1, produced by said method.

The invention further provides a pharmaceutical composition comprising an immunoconjugate of the invention and a pharmaceutically acceptable carrier, and methods of using an immunoconjugate of the invention.

In particular, the invention encompasses an immunoconjugate according to the invention for use as a medicament, and for use in the treatment of a disease. In a particular embodiment, said disease is cancer.

Also encompassed by the invention is the use of an immunoconjugate according to the invention in the manufacture of a medicament for the treatment of a disease. In a particular embodiment, said disease is cancer.

Further provided is a method of treating disease in an individual, comprising administering to said individual a therapeutically effective amount of a composition comprising an immunoconjugate according to the invention in a pharmaceutically acceptable form. In a particular embodiment, said disease is cancer.

Also provided is a method of stimulating the immune system of an individual, comprising administering to said individual an effective amount of a composition comprising an immunoconjugate according to the invention in a pharmaceutically acceptable form.

BRIEF DESCRIPTION OF THE DRAWINGS

FIGS. 4A-4C. Activation of NK cells (FIG. 4A), CD8 T cells (FIG. 4B) and CD4 T cells (FIG. 4C) within PBMCs with PD1-IL2v, CEA-IL2v, and the combination of PD1 IgG plus CEA-IL2v. PD1 IgG was included as control. CD25 expression on NK cells, CD4 T cells and CD8 T cells was used as a marker of activation.

FIGS. 7A and 7B. Proliferation of the human NK cell line NK92 induced by PD-L1-IL2v in comparison to CEA-IL2v (FIG. 7A), or by PD-L1-IL2v in comparison to PD1-IL2v (FIG. 7B), measured after 2 days.

FIGS. 18A and 18B. Immunohistochemical images of pancreas tumors stained for anti-mouse CD3 (FIG. 18A) and the T cell quantification analysis (FIG. 18B).

FIG. 19. Immunohistochemical images of pancreas tumors stained for anti-mouse PD1.

FIGS. 29A-29D. STAT5 assay on resting PBMCs of a first donor (CD8 T-cells (FIG. 29A), NK cells (FIG. 29B), CD4 T-cells (FIG. 29C) and regulatory T-cells (FIG. 29D)).

FIGS. 30A-30D. STAT5 assay on resting PBMCs of a second donor (CD4 T-cells (FIG. 30A), CD8 T-cells (FIG. 30B), regulatory T-cells (FIG. 30C) and NK cells (FIG. 30D)).

FIGS. 32A-32D. STAT5 assay on resting PBMCs of a fourth donor (CD8 T-cells (FIG. 32A), NK cells (FIG. 32B), CD4 T-cells (FIG. 32C) and regulatory T-cells (FIG. 32D)).

DETAILED DESCRIPTION OF THE INVENTION

Definitions

Figure 1:
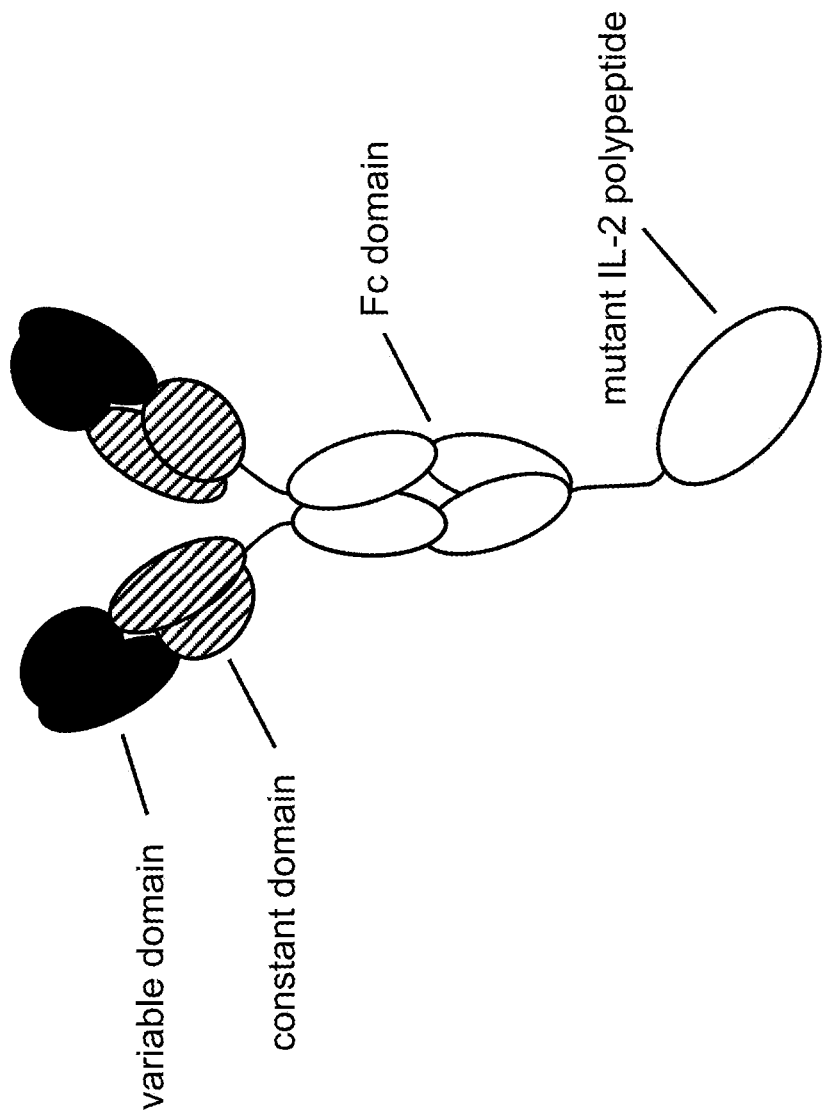
FIG. 1. Schematic representation of the IgG-IL-2 immunoconjugate format, comprising mutant IL-2 polypeptide.

Terms are used herein as generally used in the art, unless otherwise defined in the following.

The term "interleukin-2" or "IL-2" as used herein, refers to any native IL-2 from any vertebrate source, including mammals such as primates (e.g. humans) and rodents (e.g., mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 19. Unprocessed human IL-2 additionally comprises an N-terminal 20 amino acid signal peptide having the sequence of SEQ ID NO: 26, which is absent in the mature IL-2 molecule.

The term "IL-2 mutant" or "mutant IL-2 polypeptide" as used herein is intended to encompass any mutant forms of various forms of the IL-2 molecule including full-length IL-2, truncated forms of IL-2 and forms where IL-2 is linked to another molecule such as by fusion or chemical conjugation. "Full-length" when used in reference to IL-2 is intended to mean the mature, natural length IL-2 molecule. For example, full-length human IL-2 refers to a molecule that has 133 amino acids (see e.g. SEQ ID NO: 19). The various forms of IL-2 mutants are characterized in having a at least one amino acid mutation affecting the interaction of IL-2 with CD25. This mutation may involve substitution, deletion, truncation or modification of the wild-type amino acid residue normally located at that position. Mutants obtained by amino acid substitution are preferred. Unless otherwise indicated, an IL-2 mutant may be referred to herein as a mutant IL-2 peptide sequence, a mutant IL-2 polypeptide, a mutant IL-2 protein or a mutant IL-2 analog.

Designation of various forms of IL-2 is herein made with respect to the sequence shown in SEQ ID NO: 19. Various designations may be used herein to indicate the same mutation. For example a mutation from phenylalanine at position 42 to alanine can be indicated as 42A, A42, $A_{42}$, F42A, or Phe42Ala.

By a "human IL-2 molecule" as used herein is meant an IL-2 molecule comprising an amino acid sequence that is at least about 90%, at least about 91%, at least about 92%, at least about 93%, at least about 94%, at least about 95% or at least about 96% identical to the human IL-2 sequence of SEQ ID NO:19. Particularly, the sequence identity is at least about 95%, more particularly at least about 96%. In particular embodiments, the human IL-2 molecule is a full-length IL-2 molecule.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g. reduced binding to CD25. Amino acid sequence deletions and insertions include amino- and/or carboxy-terminal deletions and insertions of amino acids. An example of a terminal deletion is the deletion of the alanine residue in position 1 of full-length human IL-2. Preferred amino acid mutations are amino acid substitutions. For the purpose of altering e.g. the binding characteristics of an IL-2 polypeptide, non-conservative amino acid substitutions, i.e. replacing one amino acid with another amino acid having different structural and/or chemical properties, are particularly preferred. Preferred amino acid substitutions include replacing a hydrophobic by a hydrophilic amino acid. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

As used herein, a "wild-type" form of IL-2 is a form of IL-2 that is otherwise the same as the mutant IL-2 polypeptide except that the wild-type form has a wild-type amino acid at each amino acid position of the mutant IL-2 polypeptide. For example, if the IL-2 mutant is the full-length IL-2 (i.e. IL-2 not fused or conjugated to any other molecule), the wild-type form of this mutant is full-length native IL-2. If the IL-2 mutant is a fusion between IL-2 and another polypeptide encoded downstream of IL-2 (e.g. an antibody chain) the wild-type form of this IL-2 mutant is IL-2 with a wild-type amino acid sequence, fused to the same downstream polypeptide.

Furthermore, if the IL-2 mutant is a truncated form of IL-2 (the mutated or modified sequence within the non-truncated portion of IL-2) then the wild-type form of this IL-2 mutant is a similarly truncated IL-2 that has a wild-type sequence. For the purpose of comparing IL-2 receptor binding affinity or biological activity of various forms of IL-2 mutants to the corresponding wild-type form of IL-2, the term wild-type encompasses forms of IL-2 comprising one or more amino acid mutation that does not affect IL-2 receptor binding compared to the naturally occurring, native IL-2, such as e.g. a substitution of cysteine at a position corresponding to residue 125 of human IL-2 to alanine. In some embodiments wild-type IL-2 for the purpose of the present invention comprises the amino acid substitution C125A (see SEQ ID NO: 29). In certain embodiments according to the invention the wild-type IL-2 polypeptide to which the mutant IL-2 polypeptide is compared comprises the amino acid sequence of SEQ ID NO: 19. In other embodiments the wild-type IL-2 polypeptide to which the mutant IL-2 polypeptide is compared comprises the amino acid sequence of SEQ ID NO: 29.

The term "CD25" or "α-subunit of the IL-2 receptor" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of human CD25 is found e.g. in UniProt entry no. P01589 (version 185).

The term "high-affinity IL-2 receptor" as used herein refers to the heterotrimeric form of the IL-2 receptor, consisting of the receptor γ-subunit (also known as common cytokine receptor γ-subunit, $\gamma_c$, or CD132, see UniProt entry no. P14784 (version 192)), the receptor β-subunit (also known as CD122 or p70, see UniProt entry no. P31785 (version 197)) and the receptor α-subunit (also known as CD25 or p55, see UniProt entry no. P01589 (version 185)). The term "intermediate-affinity IL-2 receptor" by contrast refers to the IL-2 receptor including only the γ-subunit and the β-subunit, without the α-subunit (for a review see e.g. Olejniczak and Kasprzak, Med Sci Monit 14, RA179-189 (2008)).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

The affinity of the mutant or wild-type IL-2 polypeptide for various forms of the IL-2 receptor can be determined in accordance with the method set forth in the WO 2012/107417 by surface plasmon resonance (SPR), using standard instrumentation such as a BIAcore instrument (GE Healthcare) and receptor subunits such as may be obtained by recombinant expression (see e.g. Shanafelt et al., Nature Biotechnol 18, 1197-1202 (2000)). Alternatively, binding affinity of IL-2 mutants for different forms of the IL-2 receptor may be evaluated using cell lines known to express one or the other such form of the receptor. Specific illustrative and exemplary embodiments for measuring binding affinity are described hereinafter.

By "regulatory T cell" or "$T_{reg}$ cell" is meant a specialized type of CD4$^+$ T cell that can suppress the responses of other T cells. $T_{reg}$ cells are characterized by expression of the α-subunit of the IL-2 receptor (CD25) and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. $T_{reg}$ cells require IL-2 for their function and development and induction of their suppressive characteristics.

As used herein, the term "effector cells" refers to a population of lymphocytes that mediate the cytotoxic effects of IL-2. Effector cells include effector T cells such as CD8$^+$cytotoxic T cells, NK cells, lymphokine-activated killer (LAK) cells and macrophages/monocytes.

As used herein, the term "PD1", "human PD1", "PD-1" or "human PD-1" (also known as Programmed cell death protein 1, or Programmed Death 1) refers to the human protein PD1 (SEQ ID NO: 27, protein without signal sequence)/(SEQ ID NO: 28, protein with signal sequence). See also UniProt entry no. Q15116 (version 156). As used herein, an antibody "binding to PD-1", "specifically binding to PD-1", "that binds to PD-1" or "anti-PD-1 antibody" refers to an antibody that is capable of binding PD-1, especially a PD-1 polypeptide expressed on a cell surface, with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, e.g., by radioimmunoassay (RIA) or flow cytometry (FACS) or by a Surface Plasmon Resonance assay using a biosensor system such as a Biacore® system. In certain embodiments, an antibody that binds to PD-1 has a KD value of the binding affinity for binding to human PD-1 of <1 μM, <100 nM, <10 nM, <1 nM, <0.1 nM, <0.01 nM, or <0.001 nM (e.g. 10-8 M or less, e.g. from 10-8 M to 10-13 M, e.g., from 10-9 M to 10-13 M). In one embodiment, the KD value of the binding affinity is determined in a Surface Plasmon Resonance assay using the Extracellular domain (ECD) of human PD-1 (PD-1-ECD, see SEQ ID NO: 43) as antigen.

By "specific binding" is meant that the binding is selective for the antigen and can be discriminated from unwanted or non-specific interactions. The ability of an antibody to bind to a specific antigen (e.g. PD-1) can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). In one embodiment, the extent of binding of an antibody to an unrelated protein is less than about 10% of the binding of the antibody to the antigen as measured, e.g., by SPR. The antibody comprised in the immunoconjugate described herein specifically binds to PD-1.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein", "amino acid chain", or any other term used to refer to a chain of two or more amino acids, are included within the definition of "polypeptide", and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36, and is publicly available from http://fasta.bioch.virginia.edu/fasta_www2/fasta_down.shtml. Alternatively, a public server accessible at http://fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

"Isolated polynucleotide (or nucleic acid) encoding [e.g. an immunoconjugate of the invention]" refers to one or more polynucleotide molecules encoding antibody heavy and light chains and/or IL-2 polypeptides (or fragments thereof), including such polynucleotide molecule(s) in a single vector or separate vectors, and such nucleic acid molecule(s) present at one or more locations in a host cell.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette comprises polynucleotide sequences that encode immunoconjugates of the invention or fragments thereof.

The term "vector" or "expression vector" refers to a DNA molecule that is used to introduce and direct the expression of a specific gene to which it is operably associated in a cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the cell, the ribonucleic acid molecule or protein that is encoded by the gene is produced by the cellular transcription and/or translation machinery. In one embodiment, the expression vector of the invention comprises an expression cassette that comprises polynucleotide sequences that encode immunoconjugates of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the immunoconjugates of the present invention. Host cells include cultured cells, e.g. mammalian cultured cells, such as HEK cells, CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment, i.e. that is not in its natural milieu. No particular level of purification is required. For example, an isolated antibody can be removed from its native or natural environment. Recombinantly produced antibodies expressed in host cells are considered isolated for the purpose of the invention, as are native or recombinant antibodies which have been separated, fractionated, or partially or substantially purified by any suitable technique. As such, the immunoconjugates of the present invention are isolated. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., J. Chromatogr. B 848:79-87 (2007).

The terms "full-length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Holliger and Hudson, Nature Biotechnology 23:1126-1136 (2005). For a review of scFv fragments, see e.g. Pluckthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity. As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, Md. (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs; three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3(L3)-FR4.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some embodiments, some FR residues in a humanized antibody are substituted with corresponding residues from a non-human antibody (e.g., the antibody from which the HVR residues are derived), e.g., to restore or improve antibody specificity or affinity. A "humanized form" of an antibody, e.g. of a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain embodiments, a human antibody is derived from a non-human transgenic mammal, for example a mouse, a rat, or a rabbit. In certain embodiments, a human antibody is derived from a hybridoma cell line. Antibodies or antibody fragments isolated from human antibody libraries are also considered human antibodies or human antibody fragments herein.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in an immunoconjugate according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in an immunoconjuate according to the invention, comprises an additional C-terminal glycine residue (G446, numbering according to EU index of Kabat). Compositions of the invention, such as the pharmaceutical compositions described herein, comprise a population of immunoconjugates of the invention. The population of immunoconjugates may comprise molecules having a full-length heavy chain and molecules having a cleaved variant heavy chain. The population of immunoconjugates may consist of a mixture of molecules having a full-length heavy chain and molecules having a cleaved variant heavy chain, wherein at least 50%, at least 60%, at least 70%, at least 80% or at least 90% of the immunoconjugates have a cleaved variant heavy chain. In one embodiment of the invention, a composition comprising a population of immunoconjugates of the invention comprises an immunoconjugate comprising a heavy chain including a subunit of an Fc domain as specified herein with an additional C-terminal glycine-lysine dipeptide (G446 and K447, numbering according to EU index of Kabat). In one embodiment of the invention, a composition comprising a population of immunoconjugates of the invention comprises an immunoconjugate comprising a heavy chain including a subunit of an Fc domain as specified herein with an additional C-terminal glycine residue (G446, numbering according to EU index of Kabat). In one embodiment of the invention, such a composition comprises a population of immunoconjugates comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" when used in reference to antibodies refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

"Reduced binding", for example reduced binding to an Fc receptor or CD25, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

As used herein, the term "immunoconjugate" refers to a polypeptide molecule that includes at least one IL-2 molecule and at least one antibody. The IL-2 molecule can be joined to the antibody by a variety of interactions and in a variety of configurations as described herein. In particular embodiments, the IL-2 molecule is fused to the antibody via a peptide linker. Particular immunoconjugates according to the invention essentially consist of one IL-2 molecule and an antibody joined by one or more linker sequences.

By "fused" is meant that the components (e.g. an antibody and an IL-2 molecule) are linked by peptide bonds, either directly or via one or more peptide linkers.

As used herein, the terms "first" and "second" with respect to Fc domain subunits etc., are used for convenience of distinguishing when there is more than one of each type of moiety. Use of these terms is not intended to confer a specific order or orientation of the immunoconjugate unless explicitly so stated.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, immunoconjugates of the invention are used to delay development of a disease or to slow the progression of a disease.

DETAILED DESCRIPTION OF THE EMBODIMENTS

Mutant IL-2 Polypeptide

The immunoconjugates according to the present invention comprise a mutant IL-2 polypeptide having advantageous properties for immunotherapy. In particular, pharmacological properties of IL-2 that contribute to toxicity but are not essential for efficacy of IL-2 are eliminated in the mutant IL-2 polypeptide. Such mutant IL-2 polypeptides are described in detail in WO 2012/107417, which is incorporated herein by reference in its entirety. As discussed above, different forms of the IL-2 receptor consist of different subunits and exhibit different affinities for IL-2. The intermediate-affinity IL-2 receptor, consisting of the α and γ receptor subunits, is expressed on resting effector cells and is sufficient for IL-2 signaling. The high-affinity IL-2 receptor, additionally comprising the α-subunit of the receptor, is mainly expressed on regulatory T ($T_{reg}$) cells as well as on activated effector cells where its engagement by IL-2 can promote $T_{reg}$ cell-mediated immunosuppression or activation-induced cell death (AICD), respectively. Thus, without wishing to be bound by theory, reducing or abolishing the affinity of IL-2 to the α-subunit of the IL-2 receptor should reduce IL-2 induced downregulation of effector cell function by regulatory T cells and development of tumor tolerance by the process of AICD. On the other hand, maintaining the affinity to the intermediate-affinity IL-2 receptor should preserve the induction of proliferation and activation of effector cells like NK and T cells by IL-2.

The mutant interleukin-2 (IL-2) polypeptide comprised in the immunoconjugate according to the invention comprises at least one amino acid mutation that abolishes or reduces affinity of the mutant IL-2 polypeptide to the α-subunit of the IL-2 receptor and preserves affinity of the mutant IL-2 polypeptide to the intermediate-affinity IL-2 receptor each compared to a wild-type IL-2 polypeptide.

Mutants of human IL-2 (hIL-2) with decreased affinity to CD25 may for example be generated by amino acid substitution at amino acid position 35, 38, 42, 43, 45 or 72 or combinations thereof (numbering relative to the human IL-2 sequence SEQ ID NO: 19). Exemplary amino acid substitutions include K35E, K35A, R38A, R38N, R38F, R38S, R38L, R38G, R38Y, R38W, F42L, F42A, F42G, F42S, F42T, F42Q, F42E, F42N, F42D, F42R, F42K, K43E, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. Particular IL-2 mutants useful in the immunoconjugates of the invention comprise an amino acid mutation at an amino acid position corresponding to residue 42, 45, or 72 of human IL-2, or a combination thereof. In one embodiment said amino acid mutation is an amino acid substitution selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K, more specifically an amino acid substitution selected from the group of F42A, Y45A and L72G. These mutants exhibit substantially similar binding affinity to the intermediate-affinity IL-2 receptor, and have substantially reduced affinity to the α-subunit of the IL-2 receptor and the high-affinity IL-2 receptor compared to a wild-type form of the IL-2 mutant.

Other characteristics of useful mutants may include the ability to induce proliferation of IL-2 receptor-bearing T and/or NK cells, the ability to induce IL-2 signaling in IL-2 receptor-bearing T and/or NK cells, the ability to generate interferon (IFN)-γ as a secondary cytokine by NK cells, a reduced ability to induce elaboration of secondary cytokines—particularly IL-10 and TNF-α—by peripheral blood mononuclear cells (PBMCs), a reduced ability to activate regulatory T cells, a reduced ability to induce apoptosis in T cells, and a reduced toxicity profile in vivo.

Particular mutant IL-2 polypeptides useful in the invention comprise three amino acid mutations that abolish or reduce affinity of the mutant IL-2 polypeptide to the α-subunit of the IL-2 receptor but preserve affinity of the mutant IL-2 polypeptide to the intermediate affinity IL-2 receptor. In one embodiment said three amino acid mutations are at positions corresponding to residue 42, 45 and 72 of human IL-2. In one embodiment said three amino acid mutations are amino acid substitutions. In one embodiment said three amino acid mutations are amino acid substitutions selected from the group of F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K. In a specific embodiment said three amino acid mutations are amino acid substitutions F42A, Y45A and L72G (numbering relative to the human IL-2 sequence of SEQ ID NO: 19).

In certain embodiments said amino acid mutation reduces the affinity of the mutant IL-2 polypeptide to the α-subunit of the IL-2 receptor by at least 5-fold, specifically at least 10-fold, more specifically at least 25-fold. In embodiments where there is more than one amino acid mutation that reduces the affinity of the mutant IL-2 polypeptide to the α-subunit of the IL-2 receptor, the combination of these amino acid mutations may reduce the affinity of the mutant IL-2 polypeptide to the α-subunit of the IL-2 receptor by at least 30-fold, at least 50-fold, or even at least 100-fold. In one embodiment said amino acid mutation or combination of amino acid mutations abolishes the affinity of the mutant IL-2 polypeptide to the α-subunit of the IL-2 receptor so that no binding is detectable by surface plasmon resonance.

Substantially similar binding to the intermediate-affinity receptor, i.e. preservation of the affinity of the mutant IL-2 polypeptide to said receptor, is achieved when the IL-2 mutant exhibits greater than about 70% of the affinity of a wild-type form of the IL-2 mutant to the intermediate-affinity IL-2 receptor. IL-2 mutants of the invention may exhibit greater than about 80% and even greater than about 90% of such affinity.

Reduction of the affinity of IL-2 for the α-subunit of the IL-2 receptor in combination with elimination of the O-glycosylation of IL-2 results in an IL-2 protein with improved properties. For example, elimination of the O-glycosylation site results in a more homogenous product when the mutant IL-2 polypeptide is expressed in mammalian cells such as CHO or HEK cells.

Thus, in certain embodiments the mutant IL-2 polypeptide comprises an additional amino acid mutation which eliminates the O-glycosylation site of IL-2 at a position corresponding to residue 3 of human IL-2. In one embodiment said additional amino acid mutation which eliminates the O-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, and T3P. In a specific embodiment, said additional amino acid mutation is the amino acid substitution T3A.

In certain embodiments the mutant IL-2 polypeptide is essentially a full-length IL-2 molecule. In certain embodiments the mutant IL-2 polypeptide is a human IL-2 molecule. In one embodiment the mutant IL-2 polypeptide comprises the sequence of SEQ ID NO: 19 with at least one amino acid mutation that abolishes or reduces affinity of the mutant IL-2 polypeptide to the α-subunit of the IL-2 receptor but preserve affinity of the mutant IL-2 polypeptide to the intermediate affinity IL-2 receptor, compared to an IL-2 polypeptide comprising SEQ ID NO: 19 without said mutation. In another embodiment, the mutant IL-2 polypeptide comprises the sequence of SEQ ID NO: 29 with at least one amino acid mutation that abolishes or reduces affinity of the mutant IL-2 polypeptide to the α-subunit of the IL-2 receptor but preserve affinity of the mutant IL-2 polypeptide to the intermediate affinity IL-2 receptor, compared to an IL-2 polypeptide comprising SEQ ID NO: 29 without said mutation.

In a specific embodiment, the mutant IL-2 polypeptide can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

In one embodiment the mutant IL-2 polypeptide has a reduced ability to induce IL-2 signaling in regulatory T cells, compared to a wild-type IL-2 polypeptide. In one embodiment the mutant IL-2 polypeptide induces less activation-induced cell death (AICD) in T cells, compared to a wild-type IL-2 polypeptide. In one embodiment the mutant IL-2 polypeptide has a reduced toxicity profile in vivo, compared to a wild-type IL-2 polypeptide. In one embodiment the mutant IL-2 polypeptide has a prolonged serum half-life, compared to a wild-type IL-2 polypeptide.

A particular mutant IL-2 polypeptide useful in the invention comprises four amino acid substitutions at positions corresponding to residues 3, 42, 45 and 72 of human IL-2. Specific amino acid substitutions are T3A, F42A, Y45A and L72G. As demonstrated in WO 2012/107417, said quadruple mutant IL-2 polypeptide exhibits no detectable binding to CD25, reduced ability to induce apoptosis in T cells, reduced ability to induce IL-2 signaling in $T_{reg}$ cells, and a reduced toxicity profile in vivo. However, it retains ability to activate IL-2 signaling in effector cells, to induce proliferation of effector cells, and to generate IFN-γ as a secondary cytokine by NK cells.

Moreover, said mutant IL-2 polypeptide has further advantageous properties, such as reduced surface hydrophobicity, good stability, and good expression yield, as described in WO 2012/107417. Unexpectedly, said mutant IL-2 polypeptide also provides a prolonged serum half-life, compared to wild-type IL-2.

IL-2 mutants useful in the invention, in addition to having mutations in the region of IL-2 that forms the interface of IL-2 with CD25 or the glycosylation site, also may have one or more mutations in the amino acid sequence outside these regions. Such additional mutations in human IL-2 may provide additional advantages such as increased expression or stability. For example, the cysteine at position 125 may be replaced with a neutral amino acid such as serine, alanine, threonine or valine, yielding C125S IL-2, C125A IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 mutant may include a mutation whereby methionine normally occurring at position 104 of wild-type human IL-2 is replaced by a neutral amino acid such as alanine (see U.S. Pat. No. 5,206,344). The resulting mutants, e. g., des-A1 M104A IL-2, des-A1 M104A C125S IL-2, M104A IL-2, M104A C125A IL-2, des-A1 M104A C125A IL-2, or M104A C125S IL-2 (these and other mutants may be found in U.S. Pat. No. 5,116,943 and in Weiger et al., Eur J Biochem 180, 295-300 (1989)) may be used in conjunction with the particular IL-2 mutations of the invention.

Thus, in certain embodiments the mutant IL-2 polypeptide comprises an additional amino acid mutation at a position corresponding to residue 125 of human IL-2. In one embodiment said additional amino acid mutation is the amino acid substitution C125A.

The skilled person will be able to determine which additional mutations may provide additional advantages for the purpose of the invention. For example, he will appreciate that amino acid mutations in the IL-2 sequence that reduce or abolish the affinity of IL-2 to the intermediate-affinity IL-2 receptor, such as D20T, N88R or Q126D (see e.g. US 2007/0036752), may not be suitable to include in the mutant IL-2 polypeptide according to the invention.

In one embodiment, the mutant IL-2 polypeptide comprises no more than 12, no more than 11, no more than 10, no more than 9, no more than 8, no more than 7, no more than 6, or no more than 5 amino acid mutations as compared to the corresponding wild-type IL-2 sequence, e.g. the human IL-2 sequence of SEQ ID NO: 19. In a particular embodiment, the mutant IL-2 polypeptide comprises no more than 5 amino acid mutations as compared to the corresponding wild-type IL-2 sequence, e.g. the human IL-2 sequence of SEQ ID NO: 19.

In one embodiment the mutant IL-2 polypeptide comprises the sequence of SEQ ID NO: 20. In one embodiment the mutant IL-2 polypeptide consists of the sequence of SEQ ID NO: 20.

Immunoconjugates

Immunoconjugates as described herein comprise an IL- molecule and an antibody. Such immunoconjugates significantly increase the efficacy of IL-2 therapy by directly targeting IL-2 e.g. into a tumor microenvironment. According to the invention, an antibody comprised in the immunoconjugate can be a whole antibody or immunoglobulin, or a portion or variant thereof that has a biological function such as antigen specific binding affinity.

The general benefits of immunoconjugate therapy are readily apparent. For example, an antibody comprised in an immunoconjugate recognizes a tumor-specific epitope and results in targeting of the immunoconjugate molecule to the tumor site. Therefore, high concentrations of IL-2 can be delivered into the tumor microenvironment, thereby resulting in activation and proliferation of a variety of immune effector cells mentioned herein using a much lower dose of the immunoconjugate than would be required for unconjugated IL-2. Moreover, since application of IL-2 in form of immunoconjugates allows lower doses of the cytokine itself, the potential for undesirable side effects of IL-2 is restricted, and targeting the IL-2 to a specific site in the body by means of an immunoconjugate may also result in a reduction of systemic exposure and thus less side effects than obtained with unconjugated IL-2. In addition, the increased circulating half-life of an immunoconjugate compared to unconjugated IL-2 contributes to the efficacy of the immunoconjugate. However, this characteristic of IL-2 immunoconjugates may again aggravate potential side effects of the IL-2 molecule: Because of the significantly longer circulating half-life of IL-2 immunoconjugate in the bloodstream relative to unconjugated IL-2, the probability for IL-2 or other portions of the fusion protein molecule to activate components generally present in the vasculature is increased. The same concern applies to other fusion proteins that contain IL-2 fused to another moiety such as Fc or albumin, resulting in an extended half-life of IL-2 in the circulation. Therefore an immunoconjugate comprising a mutant IL-2 polypeptide as described herein and in WO 2012/107417, with reduced toxicity compared to wild-type forms of IL-2, is particularly advantageous.

As described hereinabove, targeting IL-2 directly to immune effector cells rather than tumor cells may be advantageous for IL-2 immunotherapy.

Accordingly, the invention provides a mutant IL-2 polypeptide as described hereinbefore, and an antibody that binds to PD-1. In one embodiment the mutant IL-2 polypeptide and the antibody form a fusion protein, i.e. the mutant IL-2 polypeptide shares a peptide bond with the antibody. In some embodiments, the antibody comprises an Fc domain composed of a first and a second subunit. In a specific embodiment the mutant IL-2 polypeptide is fused at its amino-terminal amino acid to the carboxy-terminal amino acid of one of the subunits of the Fc domain, optionally through a linker peptide. In some embodiments, the antibody is a full-length antibody. In some embodiments, the antibody is an immunoglobulin molecule, particularly an IgG class immunoglobulin molecule, more particularly an IgG$_1$ subclass immunoglobulin molecule. In one such embodiment, the mutant IL-2 polypeptide shares an amino-terminal peptide bond with one of the immunoglobulin heavy chains. In certain embodiments the antibody is an antibody fragment. In some embodiments the antibody is a Fab molecule or a scFv molecule. In one embodiment the antibody is a Fab molecule. In another embodiment the antibody is a scFv molecule. The immunoconjugate may also comprise more than one antibody. Where more than one antibody is comprised in the immunoconjugate, e.g. a first and a second antibody, each antibody can be independently selected from various forms of antibodies and antibody fragments. For example, the first antibody can be a Fab molecule and the second antibody can be a scFv molecule. In a specific embodiment each of said first and said second antibodies is a scFv molecule or each of said first and said second antibodies is a Fab molecule. In a particular embodiment each of said first and said second antibodies is a Fab molecule. In one embodiment each of said first and said second antibodies binds to PD-1.

Immunoconjugate Formats

Exemplary immunoconjugate formats are described in PCT publication no. WO 2011/020783, which is incorporated herein by reference in its entirety. These immunoconjugates comprise at least two antibodies. Thus, in one embodiment, the immunoconjugate according to the present invention comprises a mutant IL-2 polypeptide as described herein, and at least a first and a second antibody. In a particular embodiment, said first and second antibody are independently selected from the group consisting of an Fv molecule, particularly a scFv molecule, and a Fab molecule. In a specific embodiment, said mutant IL-2 polypeptide shares an amino- or carboxy-terminal peptide bond with said first antibody and said second antibody shares an amino- or carboxy-terminal peptide bond with either i) the mutant IL-2 polypeptide or ii) the first antibody. In a particular embodiment, the immunoconjugate consists essentially of a mutant IL-2 polypeptide and first and second antibodies, particularly Fab molecules, joined by one or more linker sequences. Such formats have the advantage that they bind with high affinity to the target antigen (PD-1), but provide only monomeric binding to the IL-2 receptor, thus avoiding targeting the immunoconjugate to IL-2 receptor bearing immune cells at other locations than the target site. In a particular embodiment, a mutant IL-2 polypeptide shares a carboxy-terminal peptide bond with a first antibody, particularly a first Fab molecule, and further shares an amino-terminal peptide bond with a second antibody, particularly a second Fab molecule. In another embodiment, a first antibody, particularly a first Fab molecule, shares a carboxy-terminal peptide bond with a mutant IL-2 polypeptide, and further shares an amino-terminal peptide bond with a second antibody, particularly a second Fab molecule. In another embodiment, a first antibody, particularly a first Fab molecule, shares an amino-terminal peptide bond with a first mutant IL-2 polypeptide, and further shares a carboxy-terminal peptide with a second antibody, particularly a second Fab molecule. In a particular embodiment, a mutant IL-2 polypeptide shares a carboxy-terminal peptide bond with a first heavy chain variable region and further shares an amino-terminal peptide bond with a second heavy chain variable region. In another embodiment a mutant IL-2 polypeptide shares a carboxy-terminal peptide bond with a first light chain variable region and further shares an amino-terminal peptide bond with a second light chain variable region. In another embodiment, a first heavy or light chain variable region is joined by a carboxy-terminal peptide bond to a mutant IL-2 polypeptide and is further joined by an amino-terminal peptide bond to a second heavy or light chain variable region. In another embodiment, a first heavy or light chain variable region is joined by an amino-terminal peptide bond to a mutant IL-2 polypeptide and is further joined by a carboxy-terminal peptide bond to a second heavy or light chain variable region. In one embodiment, a mutant IL-2 polypeptide shares a carboxy-terminal peptide bond with a first Fab heavy or light chain and further shares an amino-terminal peptide bond with a second Fab heavy or light chain. In another embodiment, a first Fab heavy or light chain shares a carboxy-terminal peptide bond with a mutant IL-2 polypeptide and further shares an amino-terminal peptide bond with a second Fab heavy or light chain. In other embodiments, a first Fab heavy or light chain shares an amino-terminal peptide bond with a mutant IL-2 polypeptide and further shares a carboxy-terminal peptide bond with a second Fab heavy or light chain. In one embodiment, the immunoconjugate comprises a mutant IL-2 polypeptide sharing an amino-terminal peptide bond with one or more scFv molecules and further sharing a carboxy-terminal peptide bond with one or more scFv molecules.

Particularly suitable formats for the immunoconjugates according to the present invention, however comprise an immunoglobulin molecule as antibody. Such immunoconjugate formats are described in WO 2012/146628, which is incorporated herein by reference in its entirety.

Accordingly, in particular embodiments, the immunoconjugate comprises a mutant IL-2 polypeptide as described herein and an immunoglobulin molecule that binds to PD-1, particularly an IgG molecule, more particularly an $IgG_1$ molecule. In one embodiment the immunoconjugate comprises not more than one mutant IL-2 polypeptide. In one embodiment the immunoglobulin molecule is human. In one embodiment, the immunoglobulin molecule comprises a human constant region, e.g. a human CH1, CH2, CH3 and/or CL domain. In one embodiment, the immunoglobulin comprises a human Fc domain, particularly a human $IgG_1$ Fc domain. In one embodiment the mutant IL-2 polypeptide shares an amino- or carboxy-terminal peptide bond with the immunoglobulin molecule. In one embodiment, the immunoconjugate essentially consists of a mutant IL-2 polypeptide and an immunoglobulin molecule, particularly an IgG molecule, more particularly an $IgG_1$ molecule, joined by one or more linker sequences. In a specific embodiment the mutant IL-2 polypeptide is fused at its amino-terminal amino acid to the carboxy-terminal amino acid of one of the immunoglobulin heavy chains, optionally through a linker peptide.

The mutant IL-2 polypeptide may be fused to the antibody directly or through a linker peptide, comprising one or more amino acids, typically about 2-20 amino acids. Linker peptides are known in the art and are described herein. Suitable, non-immunogenic linker peptides include, for example, $(G_4S)_n$, $(SG_4)_n$, $(G_4S)_n$ or $G_4(SG_4)_n$ linker peptides. "n" is generally an integer from 1 to 10, typically from 2 to 4. In one embodiment the linker peptide has a length of at least 5 amino acids, in one embodiment a length of 5 to 100, in a further embodiment of 10 to 50 amino acids. In a particular embodiment, the linker peptide has a length of 15 amino acids. In one embodiment the linker peptide is $(GxS)_n$ or $(GXS)_n G_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=3. In a particular embodiment the linker peptide is $(G_4S)_3$ (SEQ ID NO: 21). In one embodiment, the linker peptide has (or consists of) the amino acid sequence of SEQ ID NO: 21.

In a particular embodiment, the immunoconjugate comprises a mutant IL-2 molecule and an immunoglobulin molecule, particularly an $IgG_1$ subclass immunoglobulin molecule, that binds to PD-1, wherein the mutant IL-2 molecule is fused at its amino-terminal amino acid to the carboxy-terminal amino acid of one of the immunoglobulin heavy chains through the linker peptide of SEQ ID NO: 21.

In a particular embodiment, the immunoconjugate comprises a mutant IL-2 molecule and an antibody that binds to PD-1, wherein the antibody comprises an Fc domain, particularly a human $IgG_1$ Fc domain, composed of a first and a second subunit, and the mutant IL-2 molecule is fused at its amino-terminal amino acid to the carboxy-terminal amino acid of one of the subunits of the Fc domain through the linker peptide of SEQ ID NO: 21.

PD-1 Antibodies

The antibody comprised in the immunoconjugate of the invention binds to PD-1, particularly human PD-1, and is able to direct the mutant IL-2 polypeptide to a target site where PD-1 is expressed, particularly to a T cell that expresses PD-1, for example associated with a tumor.

Suitable PD-1 antibodies that may be used in the immunoconjugate of the invention are described in PCT patent application no. PCT/EP2016/073248, which is incorporated herein by reference in its entirety.

The immunoconjugate of the invention may comprise two or more antibodies, which may bind to the same or to different antigens. In particular embodiments, however, each of these antibodies binds to PD-1. In one embodiment, the antibody comprised in the immunoconjugate of the invention is monospecific. In a particular embodiment, the immunoconjugate comprises a single, monospecific antibody, particularly a monospecific immunoglobulin molecule.

The antibody can be any type of antibody or fragment thereof that retains specific binding to PD-1, particularly human PD-1. Antibody fragments include, but are not limited to, Fv molecules, scFv molecule, Fab molecule, and F(ab')₂ molecules. In particular embodiments, however, the antibody is a full-length antibody. In some embodiments, the antibody comprises an Fc domain, composed of a first and a second subunit. In some embodiments, the antibody is an immunoglobulin, particularly an IgG class, more particularly an IgG$_1$ subclass immunoglobulin.

In some embodiments, the antibody is a monoclonal antibody.

In some embodiments, the antibody comprises a HVR-H1 comprising the amino acid sequence of SEQ ID NO:1, a HVR-H2 comprising the amino acid sequence of SEQ ID NO:2, a HVR-H3 comprising the amino acid sequence of SEQ ID NO:3, a FR-H3 comprising the amino acid sequence of SEQ ID NO:7 at positions 71-73 according to Kabat numbering, a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:6.

In some embodiments, the antibody comprises (a) a heavy chain variable region (VH) comprising a HVR-H1 comprising the amino acid sequence of SEQ ID NO:1, a HVR-H2 comprising the amino acid sequence of SEQ ID NO:2, a HVR-H3 comprising the amino acid sequence of SEQ ID NO:3, and a FR-H3 comprising the amino acid sequence of SEQ ID NO:7 at positions 71-73 according to Kabat numbering, and (b) a light chain variable region (VL) comprising a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:6. In some embodiments, the heavy and/or light chain variable region is a humanized variable region. In some embodiments, the heavy and/or light chain variable region comprises human framework regions (FR).

In some embodiments, the antibody comprises a HVR-H1 comprising the amino acid sequence of SEQ ID NO:8, a HVR-H2 comprising the amino acid sequence of SEQ ID NO:9, a HVR-H3 comprising the amino acid sequence of SEQ ID NO:10, a HVR-L1 comprising the amino acid sequence of SEQ ID NO:11, a HVR-L2 comprising the amino acid sequence of SEQ ID NO:12, and a HVR-L3 comprising the amino acid sequence of SEQ ID NO:13.

In some embodiments, the antibody comprises (a) a heavy chain variable region (VH) comprising a HVR-H1 comprising the amino acid sequence of SEQ ID NO:8, a HVR-H2 comprising the amino acid sequence of SEQ ID NO:9, and a HVR-H3 comprising the amino acid sequence of SEQ ID NO:10, and (b) a light chain variable region (VL) comprising a HVR-L1 comprising the amino acid sequence of SEQ ID NO:11, a HVR-L2 comprising the amino acid sequence of SEQ ID NO:12, and a HVR-L3 comprising the amino acid sequence of SEQ ID NO:13. In some embodiments, the heavy and/or light chain variable region is a humanized variable region. In some embodiments, the heavy and/or light chain variable region comprises human framework regions (FR).

In some embodiments, the antibody comprises a heavy chain variable region (VH) comprising an amino acid sequence that is at least about 95%, 96%, 97%, 98%, 99% or 100% identical to the amino acid sequence of SEQ ID NO:14. In some embodiments, the antibody comprises a light chain variable region (VL) comprising an amino acid sequence that is at least about 95%, 96%, 97%, 98%, 99% or 100% identical to an amino acid sequence selected from the group consisting of SEQ ID NO:15, SEQ ID NO:16, SEQ ID NO: 17, and SEQ ID NO:18. In some embodiments, the antibody comprises (a) a heavy chain variable region (VH) comprising an amino acid sequence that is at least about 95%, 96%, 97%, 98%, 99% or 100% identical to the amino acid sequence of SEQ ID NO:14, and (b) a light chain variable region (VL) comprising an amino acid sequence that is at least about 95%, 96%, 97%, 98%, 99% or 100% identical to an amino acid sequence selected from the group consisting of SEQ ID NO:15, SEQ ID NO:16, SEQ ID NO: 17, and SEQ ID NO:18.

In a particular embodiment, the antibody comprises (a) a heavy chain variable region (VH) comprising the amino acid sequence of SEQ ID NO: 14, and (b) a light chain variable region (VL) comprising the amino acid sequence of SEQ ID NO: 15.

In some embodiments, the antibody is a humanized antibody. In one embodiment, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 31 and 32 (human kappa and lambda CL domains, respectively) and SEQ ID NO: 33 (human IgG1 heavy chain constant domains CH1-CH2-CH3). In some embodiments, the antibody comprises a light chain constant region comprising the amino acid sequence of SEQ ID NO: 31 or SEQ ID NO: 32, particularly the amino acid sequence of SEQ ID NO: 31. In some embodiments, the antibody comprises a heavy chain constant region comprising an amino acid sequence that is at least about 95%, 96%, 97%, 98%, 99% or 100% identical to the amino acid sequence of SEQ ID NO: 33. Particularly, the heavy chain constant region may comprise amino acid mutations in the Fc domain as described herein.

Fc Domain

In particular embodiments, the antibody comprised in the immunoconjugates according to the invention comprises an Fc domain, composed of a first and a second subunit. The Fc domain of an antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the immunoconjugate of the invention comprises not more than one Fc domain. In one embodiment the Fc domain of the antibody comprised in the immunoconjugate is an IgG Fc domain. In a particular embodiment the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat EU index numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further particular embodiment the Fc domain is a human Fc domain. In an even more particular embodiment, the Fc domain is a human IgG$_1$ Fc domain. An exemplary sequence of a human IgG$_1$ Fc region is given in SEQ ID NO: 30.

Fc Domain Modifications Promoting Heterodimerization

Immunoconjugates according to the invention comprise a mutant IL-2 polypeptide, particularly a single (not more than one) mutant IL-2 polypeptide, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of the immunoconjugate in recombinant production, it will thus be advantageous to introduce in the Fc domain of the antibody a modification promoting the association of the desired polypeptides.

Accordingly, in particular embodiments, the Fc domain of the antibody comprised in the immunoconjugate according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed).

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the antibody comprised in the immunoconjugate an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain (the "knobs" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index). In some embodiments, the second subunit of the Fc domain additionally comprises the amino acid substitutions H435R and Y436F (numbering according to Kabat EU index).

In a particular embodiment the mutant IL-2 polypeptide is fused (optionally through a linker peptide) to the first subunit of the Fc domain (comprising the "knob" modification). Without wishing to be bound by theory, fusion of the mutant IL-2 polypeptide to the knob-containing subunit of the Fc domain will (further) minimize the generation of immunoconjugates comprising two mutant IL-2 polypeptides (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459, is used alternatively. This approach is based on the introduction of charged amino acids with opposite charges at specific amino acid positions in the CH3/CH3 domain interface between the two subunits of the Fc domain. One preferred embodiment for the antibody comprised in the immunoconjugate of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment, the antibody comprised in the immunoconjugate of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment, the antibody comprised in the immunoconjugate of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment, the heterodimerization approach described in WO 2013/157953 is used alternatively. In one embodiment, a first CH3 domain comprises amino acid mutation T366K and a second CH3 domain comprises amino acid mutation L351D (numberings according to Kabat EU index). In a further embodiment, the first CH3 domain comprises further amino acid mutation L351K. In a further embodiment, the second CH3 domain comprises further an amino acid mutation selected from Y349E, Y349D and L368E (preferably L368E) (numberings according to Kabat EU index).

In one embodiment, the heterodimerization approach described in WO 2012/058768 is used alternatively. In one embodiment, a first CH3 domain comprises amino acid mutations L351Y, Y407A and a second CH3 domain comprises amino acid mutations T366A, K409F. In a further embodiment, the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment, a first CH3 domain comprises amino acid mutations L351Y, Y407A and a second CH3 domain comprises amino acid mutations T366V, K409F. In a further embodiment a first CH3 domain comprises amino acid mutation Y407A and a second CH3 domain comprises amino acid mutations T366A, K409F. In a further embodiment, the second CH3 domain further comprises amino acid mutations K392E, T411E, D399R and S400R (numberings according to Kabat EU index).

In one embodiment the heterodimerization approach described in WO 2011/143545 is used alternatively, e.g. with the amino acid modification at a position selected from the group consisting of 368 and 409 (numbering according to Kabat EU index).

In one embodiment, the heterodimerization approach described in WO 2011/090762, which also uses the knobs-into-holes technology described above, is used alternatively. In one embodiment, a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (numberings according to Kabat EU index).

In one embodiment, the antibody comprised in the immunoconjugate or its Fc domain is of $IgG_2$ subclass and the heterodimerization approach described in WO 2010/129304 is used alternatively.

In an alternative embodiment, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment, the first CH3 domain further comprises amino acid substitution of K409 or R409 with a negatively charged amino acid (e.g. glutamic acid (E), or aspartic acid (D), preferably K409D or R409D). In a further embodiment, the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (numberings according to Kabat EU index).

In still another embodiment, the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the immunoconjugate favorable pharmacokinetic properties, including a long serum half-life which contributes to good accumulation in the target tissue and a favorable tissue-blood distribution ratio. At the same time it may, however, lead to undesirable targeting of the immunoconjugate to cells expressing Fc receptors rather than to the preferred antigen-bearing cells. Moreover, the co-activation of Fc receptor signaling pathways may lead to cytokine release which, in combination with the IL-2 polypeptide and the long half-life of the immunoconjugate, results in excessive activation of cytokine receptors and severe side effects upon systemic administration. In line with this, conventional IgG-IL-2 immunoconjugates have been described to be associated with infusion reactions (see e.g. King et al., J Clin Oncol 22, 4463-4473 (2004)).

Accordingly, in particular embodiments, the Fc domain of the antibody comprised in the immunoconjugate according to the invention exhibits reduced binding affinity to an Fc receptor and/or reduced effector function, as compared to a native IgG$_1$ Fc domain. In one such embodiment the Fc domain (or the antibody comprising said Fc domain) exhibits less than 50%, preferably less than 20%, more preferably less than 10% and most preferably less than 5% of the binding affinity to an Fc receptor, as compared to a native IgG$_1$ Fc domain (or an antibody comprising a native IgG$_1$ Fc domain), and/or less than 50%, preferably less than 20%, more preferably less than 10% and most preferably less than 5% of the effector function, as compared to a native IgG$_1$ Fc domain domain (or an antibody comprising a native IgG$_1$ Fc domain). In one embodiment, the Fc domain domain (or an antibody comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native IgG$_1$ Fc domain domain. Substantially similar binding to FcRn is achieved when the Fc domain (or an antibody comprising said Fc domain) exhibits greater than about 70%, particularly greater than about 80%, more particularly greater than about 90% of the binding affinity of a native IgG$_1$Fc domain (or an antibody comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the antibody comprised in the immunoconjugate comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the antibody comprising an engineered Fc domain exhibits less than 20%, particularly less than 10%, more particularly less than 5% of the binding affinity to an Fc receptor as compared to an antibody comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or an antibody comprising said Fc domain) exhibits greater than about 70% of the binding affinity of a non-engineered form of the Fc domain (or an antibody comprising said non-engineered form of the Fc domain) to FcRn. The Fc domain, or antibody comprised in the immunoconjugate of the invention comprising said Fc domain, may exhibit greater than about 80% and even greater than about 90% of such affinity. In certain embodiments the Fc domain of the antibody comprised in the immunoconjugate is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or an antibody comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329 (numberings according to Kabat EU index). In a more specific embodiment the Fc domain comprises an amino acid substitution at a position selected from the group of L234, L235 and P329 (numberings according to Kabat EU index). In some embodiments the Fc domain comprises the amino acid substitutions L234A and L235A (numberings according to Kabat EU index). In one such embodiment, the Fc domain is an IgG$_1$Fc domain, particularly a human IgG$_1$ Fc domain. In one embodiment the Fc domain comprises an amino acid substitution at position P329. In a more specific embodiment the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297 and P331 (numberings according to Kabat EU index). In a more specific embodiment the further amino acid substitution is E233P, L234A, L235A, L235E, N297A, N297D or P331S. In particular embodiments the Fc domain comprises amino acid substitutions at positions P329, L234 and L235 (numberings according to Kabat EU index). In more particular embodiments the Fc domain comprises the amino acid mutations L234A, L235A and P329G ("P329G LALA", "PGLALA" or "LALAPG"). Specifically, in particular embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In one such embodiment, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the antibody comprised in the immunoconjugate of the invention is an IgG$_4$ Fc domain, particularly a human IgG$_4$ Fc domain. In one embodiment the IgG$_4$ Fc domain comprises amino acid substitutions at position S228, specifically the amino acid substitution S228P (numberings according to Kabat EU index). To further reduce its binding affinity to an Fc receptor and/or its effector function, in one embodiment the IgG$_4$ Fc domain comprises an amino acid substitution at position L235, specifically the amino acid substitution L235E (numberings according to Kabat EU index). In another embodiment, the IgG$_4$ Fc domain comprises an amino acid substitution at position P329, specifically the amino acid substitution P329G (numberings according to Kabat EU index). In a particular embodiment, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a particular embodiment, the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain embodiments N-glycosylation of the Fc domain has been eliminated. In one such embodiment, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or antibodies comprising an Fc domain for Fc receptors may be evaluated using cell lines known to express particular Fc receptors, such as human NK cells expressing FcγIIIa receptor.

Effector function of an Fc domain, or an antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96© non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half life determinations can also be performed using methods known in the art (see, e.g., Petkova, S. B. et al., Int'l. Immunol. 18(12):1759-1769 (2006); WO 2013/120929).

Particular Aspects of the Invention

In one aspect, the invention provides an immunoconjugate comprising a mutant IL-2 polypeptide and an antibody that binds to PD-1,
wherein the mutant IL-2 polypeptide is a human IL-2 molecule comprising the amino acid substitutions F42A, Y45A and L72G (numbering relative to the human IL-2 sequence SEQ ID NO: 19); and
wherein the antibody comprises (a) a heavy chain variable region (VH) comprising the amino acid sequence of SEQ ID NO:14, and (b) a light chain variable region (VL) comprising the amino acid sequence of SEQ ID NO:15.

In one aspect, the invention provides an immunoconjugate comprising a mutant IL-2 polypeptide and an antibody that binds to PD-1,
wherein the mutant IL-2 polypeptide is a human IL-2 molecule comprising the amino acid substitutions T3A, F42A, Y45A, L72G and C125A (numbering relative to the human IL-2 sequence SEQ ID NO: 19); and
wherein the antibody comprises (a) a heavy chain variable region (VH) comprising the amino acid sequence of SEQ ID NO:14, and (b) a light chain variable region (VL) comprising the amino acid sequence of SEQ ID NO:15.

In one aspect, the invention provides an immunoconjugate comprising a mutant IL-2 polypeptide and an antibody that binds to PD-1,
wherein the mutant IL-2 polypeptide comprises the amino acid sequence of SEQ ID NO: 20; and
wherein the antibody comprises (a) a heavy chain variable region (VH) comprising the amino acid sequence of SEQ ID NO:14, and (b) a light chain variable region (VL) comprising the amino acid sequence of SEQ ID NO:15.

In one embodiment according to any of the above aspects of the invention, the antibody is an IgG class immunoglobulin, comprising a human IgG$_1$ Fc domain composed of a first and a second subunit,
wherein in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index),
and wherein further each subunit of the Fc domain comprises the amino acid substitutions L234A, L235A and P329G (Kabat EU index numbering).

In this embodiment, the mutant IL-2 polypeptide may be fused at its amino-terminal amino acid to the carboxy-terminal amino acid of the first subunit of the Fc domain, through a linker peptide of SEQ ID NO: 21.

In one aspect, the invention provides an immunoconjugate comprising a polypeptide comprising an amino acid sequence that is at least about 80%, 85%, 90%, 95%, 96%, 97%, 98%, 99% or 100% identical to the sequence of SEQ ID NO:22, a polypeptide comprising an amino acid sequence that is at least about 80%, 85%, 90%, 95%, 96%, 97%, 98%, 99% or 100% identical to the sequence of SEQ ID NO:23 or SEQ ID NO:24, and a polypeptide comprising an amino acid sequence that is at least about 80%, 85%, 90%, 95%, 96%, 97%, 98%, 99% or 100% identical to the sequence of SEQ ID NO:25.

Polynucleotides

The invention further provides isolated polynucleotides encoding an immunoconjugate as described herein or a fragment thereof. In some embodiments, said fragment is an antigen binding fragment.

The polynucleotides encoding immunoconjugates of the invention may be expressed as a single polynucleotide that encodes the entire immunoconjugate or as multiple (e.g., two or more) polynucleotides that are co-expressed. Polypeptides encoded by polynucleotides that are co-expressed may associate through, e.g., disulfide bonds or other means to form a functional immunoconjugate. For example, the light chain portion of an antibody may be encoded by a separate polynucleotide from the portion of the immunoconjugate comprising the heavy chain portion of the antibody and the mutant IL-2 polypeptide. When co-expressed, the heavy chain polypeptides will associate with the light chain polypeptides to form the immunoconjugate. In another example, the portion of the immunoconjugate comprising one of the two Fc domain subunits and the mutant IL-2 polypeptide could be encoded by a separate polynucleotide from the portion of the immunoconjugate comprising the other of the two Fc domain subunits. When co-expressed, the Fc domain subunits will associate to form the Fc domain.

In some embodiments, the isolated polynucleotide encodes the entire immunoconjugate according to the invention as described herein. In other embodiments, the isolated polynucleotide encodes a polypeptide comprised in the immunoconjugate according to the invention as described herein.

In one embodiment, an isolated polynucleotide of the invention encodes the heavy chain of the antibody comprised in the immunoconjugate (e.g. an immunoglobulin heavy chain), and the mutant IL-2 polypeptide. In another embodiment, an isolated polynucleotide of the invention encodes the light chain of the antibody comprised in the immunoconjugate.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Mutant IL-2 polypeptides useful in the invention can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. In this regard, the nucleotide sequence of native IL-2 has been described by Taniguchi et al. (Nature 302, 305-10 (1983)) and nucleic acid encoding human IL-2 is available from public depositories such as the American Type Culture Collection (Rockville Md.). The sequence of native human IL-2 is shown in SEQ ID NO: 19. Substitution or insertion may involve natural as well as non-natural amino acid residues. Amino acid modification includes well known methods of chemical modification such as the addition of glycosylation sites or carbohydrate attachments, and the like.

Immunoconjugates of the invention may be obtained, for example, by solid-state peptide synthesis (e.g. Merrifield solid phase synthesis) or recombinant production. For recombinant production one or more polynucleotide encoding the immunoconjugate (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an immunoconjugate (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the immunoconjugate (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the immunoconjugate of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. For example, human IL-2 is translated with a 20 amino acid signal sequence at the N-terminus of the polypeptide, which is subsequently cleaved off to produce the mature, 133 amino acid human IL-2. In certain embodiments, the native signal peptide, e.g. the IL-2 signal peptide or an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the immunoconjugate may be included within or at the ends of the immunoconjugate (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) one or more vector comprising one or more polynucleotide that encodes the immunoconjugate of the invention. As used herein, the term "host cell" refers to any kind of cellular system which can be engineered to generate the immunoconjugates of the invention or fragments thereof. Host cells suitable for replicating and for supporting expression of immunoconjugates are well known in the art. Such cells may be transfected or transduced as appropriate with the particular expression vector and large quantities of vector containing cells can be grown for seeding large scale fermenters to obtain sufficient quantities of the immunoconjugate for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NSO, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NSO, Sp20 cell).

Standard technologies are known in the art to express foreign genes in these systems. Cells expressing a mutant-IL-2 polypeptide fused to either the heavy or the light chain of an antibody may be engineered so as to also express the other of the antibody chains such that the expressed mutant IL-2 fusion product is an antibody that has both a heavy and a light chain.

In one embodiment, a method of producing an immunoconjugate according to the invention is provided, wherein the method comprises culturing a host cell comprising one or more polynucleotide encoding the immunoconjugate, as provided herein, under conditions suitable for expression of the immunoconjugate, and optionally recovering the immunoconjugate from the host cell (or host cell culture medium).

In the immunoconjugate of the invention, the mutant IL-2 polypeptide may be genetically fused to the antibody, or may be chemically conjugated to the antibody. Genetic fusion of the IL-2 polypeptide to the antibody can be designed such that the IL-2 sequence is fused directly to the polypeptide or indirectly through a linker sequence. The composition and length of the linker may be determined in accordance with methods well known in the art and may be tested for efficacy. Particular linker peptides are described herein. Additional sequences may also be included to incorporate a cleavage site to separate the individual components of the fusion if desired, for example an endopeptidase recognition sequence. In addition, an IL-2 fusion protein may also be synthesized chemically using methods of polypeptide synthesis as is well known in the art (e.g. Merrifield solid phase synthesis). Mutant IL-2 polypeptides may be chemically conjugated to other molecules, e.g. antibodies, using well known chemical conjugation methods. Bi-functional cross-linking reagents such as homofunctional and heterofunctional cross-linking reagents well known in the art can be used for this purpose. The type of cross-linking reagent to use depends on the nature of the molecule to be coupled to IL-2 and can readily be identified by those skilled in the art. Alternatively, or in addition, mutant IL-2 and/or the molecule to which it is intended to be conjugated may be chemically derivatized such that the two can be conjugated in a separate reaction as is also well known in the art.

The immunoconjugates of the invention comprise an antibody. Methods to produce antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty). Immunoconjugates, antibodies, and methods for producing the same are also described in detail e.g. in PCT publication nos. WO 2011/020783, WO 2012/107417, and WO 2012/146628, each of which are incorporated herein by reference in their entirety.

Any animal species of antibody may be used in the immunoconjugates of the invention. Non-limiting antibodies useful in the present invention can be of murine, primate, or human origin. If the immunoconjugate is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., Methods 36:61-68 (2005) and Klimka et al., *Br. J. Cancer*, 83:252-260 (2000) (describing the "guided selection" approach to FR shuffling). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human antibodies can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolation from human antibody libraries, as described herein.

Antibodies useful in the invention may be isolated by screening combinatorial libraries for antibodies with the desired activity or activities. Methods for screening combinatorial libraries are reviewed, e.g., in Lerner et al. in *Nature Reviews* 16:498-508 (2016). For example, a variety of methods are known in the art for generating phage display libraries and screening such libraries for antibodies possessing the desired binding characteristics. Such methods are reviewed, e.g., in Frenzel et al. in mAbs 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178: 1-37 (O'Brien et al., ed., Human Press, Totowa, N.J., 2001) and in Marks and Bradbury in *Methods in Molecular Biology* 248:161-175 (Lo, ed., Human Press, Totowa, N.J., 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in *EMBO Journal* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319:155-175 (2015) as well as in the Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Further chemical modification of the immunoconjugate of the invention may be desirable. For example, problems of immunogenicity and short half-life may be improved by conjugation to substantially straight chain polymers such as polyethylene glycol (PEG) or polypropylene glycol (PPG) (see e.g. WO 87/00056).

Immunoconjugates prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the immunoconjugate binds. For example, an antibody which specifically binds the mutant IL-2 polypeptide may be used. For affinity chromatography purification of immunoconjugates of the invention, a matrix with protein A or protein G may be used. For example, sequential Protein A or G affinity chromatography and size exclusion chromatography can be used to isolate an immunoconjugate essentially as described in the Examples. The purity of the immunoconjugate can be determined by any of a variety of well known analytical methods including gel electrophoresis, high pressure liquid chromatography, and the like.

Compositions, Formulations, and Routes of Administration

In a further aspect, the invention provides pharmaceutical compositions comprising an immunoconjugate as described herein, e.g., for use in any of the below therapeutic methods. In one embodiment, a pharmaceutical composition comprises any of the immunoconjugates provided herein and a pharmaceutically acceptable carrier. In another embodiment, a pharmaceutical composition comprises any of the immunoconjugates provided herein and at least one additional therapeutic agent, e.g., as described below.

Further provided is a method of producing an immunoconjugate of the invention in a form suitable for administration in vivo, the method comprising (a) obtaining an immunoconjugate according to the invention, and (b) formulating the immunoconjugate with at least one pharmaceutically acceptable carrier, whereby a preparation of immunoconjugate is formulated for administration in vivo.

Pharmaceutical compositions of the present invention comprise a therapeutically effective amount of immunoconjugate dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains immunoconjugate and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

An immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the immunoconjugates of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the immunoconjugates may be in powder form for constitution with a suitable vehicle, e.g., sterile pyrogen-free water, before use. Sterile injectable solutions are prepared by incorporating the immunoconjugates of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the immunoconjugates may also be formulated as a depot preparation. Such long acting formulations may be administered by implantation (for example subcutaneously or intramuscularly) or by intramuscular injection. Thus, for example, the immunoconjugates may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the immunoconjugates of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The immunoconjugates may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the immunoconjugates provided herein may be used in therapeutic methods. Immunoconjugates of the invention may be used as immunotherapeutic agents, for example in the treatment of cancers.

For use in therapeutic methods, immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Immunoconjugates of the invention may be particularly useful in treating disease states where stimulation of the immune system of the host is beneficial, in particular conditions where an enhanced cellular immune response is desirable. These may include disease states where the host immune response is insufficient or deficient. Disease states for which the immunoconjugates of the invention may be administered comprise, for example, a tumor or infection where a cellular immune response would be a critical mechanism for specific immunity. The immunoconjugates of the invention may be administered per se or in any suitable pharmaceutical composition.

In one aspect, immunoconjugates of the invention for use as a medicament are provided. In further aspects, immunoconjugates of the invention for use in treating a disease are provided. In certain embodiments, immunoconjugates of the invention for use in a method of treatment are provided. In one embodiment, the invention provides an immunoconjugate as described herein for use in the treatment of a disease in an individual in need thereof. In certain embodiments, the invention provides an immunoconjugate for use in a method of treating an individual having a disease comprising administering to the individual a therapeutically effective amount of the immunoconjugate. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides an immunoconjugate for use in stimulating the immune system. In certain embodiments, the invention provides an immunoconjugate for use in a method of stimulating the immune system in an individual comprising administering to the individual an effective amount of the immunoconjugate to stimulate the immune system. An "individual" according to any of the above embodiments is a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the invention provides for the use of an immunoconjugate of the invention in the manufacture or preparation of a medicament. In one embodiment, the medicament is for the treatment of a disease in an individual in need thereof. In one embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for stimulating the immune system. In a further embodiment, the medicament is for use in a method of stimulating the immune system in an individual comprising administering to the individual an effective amount of the medicament to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the invention provides a method for treating a disease in an individual. In one embodiment, the method comprises administering to an individual having such disease a therapeutically effective amount of an immunoconjugate of the invention. In one embodiment a composition is administered to said individual, comprising the immunoconjugate of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In a further aspect, the invention provides a method for stimulating the immune system in an individual, comprising administering to the individual an effective amount of an immunoconjugate to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an immunoconjugate of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of kidney cancer, skin cancer, lung cancer, colorectal cancer, breast cancer, brain cancer, head and neck cancer, prostate cancer and bladder cancer. A skilled artisan readily recognizes that in many cases the immunoconjugates may not provide a cure but may only provide partial benefit. In some embodiments, a physiological change having some benefit is also considered therapeutically beneficial. Thus, in some embodiments, an amount of immunoconjugate that provides a physiological change is considered an "effective amount" or a "therapeutically effective amount". The subject, patient, or individual in need of treatment is typically a mammal, more specifically a human.

In some embodiments, an effective amount of an immunoconjugate of the invention is administered to a cell. In other embodiments, a therapeutically effective amount of an immunoconjugates of the invention is administered to an individual for the treatment of disease.

For the prevention or treatment of disease, the appropriate dosage of an immunoconjugate of the invention (when used alone or in combination with one or more other additional therapeutic agents) will depend on the type of disease to be treated, the route of administration, the body weight of the patient, the type of molecule (e.g. comprising an Fc domain or not), the severity and course of the disease, whether the immunoconjugate is administered for preventive or therapeutic purposes, previous or concurrent therapeutic interventions, the patient's clinical history and response to the immunoconjugate, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The immunoconjugate is suitably administered to the patient at one time or over a series of treatments. Depending on the type and severity of the disease, about 1 µg/kg to 15 mg/kg (e.g. 0.1 mg/kg-10 mg/kg) of immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the immunoconjugate would be in the range from about 0.005 mg/kg to about 10 mg/kg. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the immunoconjugate). An initial higher loading dose, followed by one or more lower doses may be administered. However, other dosage regimens may be useful. The progress of this therapy is easily monitored by conventional techniques and assays.

The immunoconjugates of the invention will generally be used in an amount effective to achieve the intended purpose. For use to treat or prevent a disease condition, the immunoconjugates of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the immunoconjugates which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the immunoconjugates may not be related to plasma concentration. One having skill in the art will be able to optimize therapeutically effective local dosages without undue experimentation.

A therapeutically effective dose of the immunoconjugates described herein will generally provide therapeutic benefit without causing substantial toxicity. Toxicity and therapeutic efficacy of an immunoconjugate can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Immunoconjugates that exhibit large therapeutic indices are preferred. In one embodiment, the immunoconjugate according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with immunoconjugates of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The maximum therapeutic dose of an immunoconjugate comprising a mutant IL-2 polypeptide as described herein may be increased from those used for an immunoconjugate comprising wild-type IL-2.

Other Agents and Treatments

The immunoconjugates according to the invention may be administered in combination with one or more other agents in therapy. For instance, an immunoconjugate of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of immunoconjugate used, the type of disorder or treatment, and other factors discussed above. The immunoconjugates are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the immunoconjugate of the invention can occur prior to, simultaneously, and/or following, administration of the additional therapeutic agent and/or adjuvant. Immunoconjugates of the invention may also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an immunoconjugate of the invention. The label or package insert indicates that the composition is used for treating the condition of choice. Moreover, the article of manufacture may comprise (a) a first container with a composition contained therein, wherein the composition comprises an immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Amino Acid Sequences

|  | AMINO ACID SEQUENCE | SEQ ID NO |
|---|---|---|
| PD-1 minimal HVR-H1 | SSYT | 1 |
| PD-1 minimal HVR-H2 | SGGGRDIY | 2 |
| PD-1 minimal HVR-H3 | GRVYF | 3 |
| PD-1 minimal HVR-L1 | TSDNSF | 4 |
| PD-1 minimal HVR-L2 | RSSTLES | 5 |
| PD-1 minimal HVR-L3 | NYDVPW | 6 |
| fragment of FR-H3 (RDN at Kabat pos. 71-73) | RDN | 7 |
| PD-1 HVR-H1 | GFSFSSY | 8 |
| PD-1 HVR-H2 | GGR | 9 |
| PD-1 HVR-H3 | TGRVYFALD | 10 |
| PD-1 HVR-L1 | SESVDTSDNSF | 11 |
| PD-1 HVR-L2 | RSS | 12 |
| PD-1 HVR-L3 | NYDVPW | 13 |
| PD-1 VH (1, 2, 3, 4) | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSS | 14 |
| PD-1 VL(1) | DIVMTQSPDSLAVSLGERATINCKASESVDTSDN SFIHWYQQKPGQSPKLLIYRSSTLESGVPDRFSG SGSGTDFTLTISSLQAEDVAVYYCQQNYDVPWTF GQGTKVEIK | 15 |
| PD-1 VL (2) | DVVMTQSPLSLPVTLGQPASISCRASESVDTSDN SFIHWYQQRPGQSPRLLIYRSSTLESGVPDRFSG SGSGTDFTLKISRVEAEDVGVYYCQQNYDVPWTF GQGTKVEIK | 16 |
| PD-1 VL (3) | EIVLTQSPATLSLSPGERATLSCRASESVDTSDN SFIHWYQQKPGQSPRLLIYRSSTLESGIPARFSG SGSGTDFTLTISSLEPEDFAVYYCQQNYDVPWTF GQGTKVEIK | 17 |
| PD-1 VL (4) | EIVLTQSPATLSLSPGERATLSCRASESVDTSDN SFIHWYQQKPGQSPRLLIYRSSTLESGIPARFSG SGSGTDFTLTISSLEPEDFAVYYCQQNYDVPWTF GQGTKVEIK | 18 |
| Human IL-2 | APTSSSTKKTQLQLEHLLLDLQMILNGINNYKNP KLTRMLTFKFYMPKKATELKHLQCLEEELKPLEE VLNLAQSKNFHLRPRDLISNINVIVLELKGSETT FMCEYADETATIVEFLNRWITFCQSIISTLT | 19 |
| Human IL-2 (T3A, F42A, Y45Y, L72G, C125A) | APASSSTKKTQLQLEHLLLDLQMILNGINNYKNP KLTRMLTAKFAMPKKATELKHLQCLEEELKPLEE VLNGAQSKNFHLRPRDLISNINVIVLELKGSETT FMCEYADETATIVEFLNRWITFAQSIISTLT | 20 |
| linker | GGGGSGGGGSGGGGS | 21 |

| | AMINO ACID SEQUENCE | SEQ ID NO |
|---|---|---|
| PD-1 IL2v - HC with IL2v (Fc knob, LALAPG) | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSPGGGGSGGGGSGGGGSAPASSSTKKTQL QLEHLLLDLQMILNGINNYKNPKLTRMLTAKFAM PKKATELKHLQCLEEELKPLEEVLNGAQSKNFHL RPRDLISNINVIVLELKGSETTFMCEYADETATI VEFLNRWITFAQSIISTLT | 22 |
| PD-1 IL2v - HC without IL2v (Fc hole, LALAPG) | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSSASTKGPSVFPLAPSSK STSGGTAALGCLVKDYFPEPVTVSWNSGALTSGV HTFPAVLQSSGLYSLSSWTVPSSSLGTQTYICNV NHKPSNTKVDKKVEPKSCDKTHTCPPCPAPEAAG GPSVFLFPPKPKDTLMISRTPEVTCVVVDVSHED PEVKFNWYVDGVEVHNAKTKPREEQYNSTYRVVS VLTVLHQDWLNGKEYKCKVSNKALGAPIEKTISK AKGQPREPQVCTLPPSRDELTKNQVSLSCAVKGF YPSDIAVEWESNGQPENNYKTTPPVLDSDGSFFL VSKLTVDKSRWQQGNVFSCSVMHEALHNHYTQKS LSLSP | 23 |
| PD-1 IL2v - HC without IL2v (Fc hole, LALAPG, HYRF) | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSSASTKGPSVFPLAPSSK STSGGTAALGCLVKDYFPEPVTVSWNSGALTSGV HTFPAVLQSSGLYSLSSWTVPSSSLGTQTYICNV NHKPSNTKVDKKVEPKSCDKTHTCPPCPAPEAAG GPSVFLFPPKPKDTLMISRTPEVTCVVVDVSHED PEVKFNWYVDGVEVHNAKTKPREEQYNSTYRVVS VLTVLHQDWLNGKEYKCKVSNKALGAPIEKTISK AKGQPREPQVCTLPPSRDELTKNQVSLSCAVKGF YPSDIAVEWESNGQPENNYKTTPPVLDSDGSFFL VSKLTVDKSRWQQGNVFSCSVMHEALHNRFTQKS LSLSP | 24 |
| PD-1 IL2v - LC | DIVMTQSPDSLAVSLGERATINCKASESVDTSDN SFIHWYQQKPGQSPKLLIYRSSTLESGVPDRFSG SGSGTDFTLTISSLQAEDVAVYYCQQNYDVPWTF GQGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC | 25 |
| hIL-2 signal peptide | MYRMQLLSCIALSLALVTNS | 26 |
| hPD-1 (without signal sequence) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTYL CGAISLAPKAQIKESLRAELRVTERRAEVPTAHP SPSPRPAGQFQTLVVGVVGGLLGSLVLLVWVLAV ICSRAARGTIGARRTGQPLKEDPSAVPVFSVDYG ELDFQWREKTPEPPVPCVPEQTEYATIVFPSGMG TSSPARRGSADGPRSAQPLRPEDGHCSWPL | 27 |
| hPD-1 (with signal sequence) | MQIPQAPWPVVWAVLQLGWRPGWFLDSPDRPWNP PTFSPALLVVTEGDNATFTCSFSNTSESFVLNWY RMSPSNQTDKLAAFPEDRSQPGQDCRFRVTQLPN GRDFHMSVVRARRNDSGTYLCGAISLAPKAQIKE SLRAELRVTERRAEVPTAHPSPSPRPAGQFQTLV | 28 |

| | AMINO ACID SEQUENCE | SEQ ID NO |
|---|---|---|
| | VGVVGGLLGSLVLLVWVLAVICSRAARGTIGARR TGQPLKEDPSAVPVFSVDYGELDFQWREKTPEPP VPCVPEQTEYATIVFPSGMGTSSPARRGSADGPR SAQPLRPEDGHCSWPL | |
| Human IL-2 (C125A) | APTSSSTKKTQLQLEHLLLDLQMILNGINNYKNP KLTRMLTFKFYMPKKATELKHLQCLEEELKPLEE VLNLAQSKNFHLRPRDLISNINVIVLELKGSETT FMCEYADETATIVEFLNRWITFAQSIISTLT | 29 |
| Human IgG1 Fc domain | DKTHTCPPCPAPELLGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALPAPIEKTISKAKGQPREPQVYTLPPSRD ELTKNQVSLTCLVKGFYPSDIAVEWESNGQPENN YKTTPPVLDSDGSFFLYSKLTVDKSRWQQGNVFS CSVMHEALHNHYTQKSLSLSP | 30 |
| Human kappa CL domain | RTVAAPSVFIFPPSDEQLKSGTASVVCLLNNFYP REAKVQWKVDNALQSGNSQESVTEQDSKDSTYSL SSTLTLSKADYEKHKVYACEVTHQGLSSPVTKSF NRGEC | 31 |
| Human lambda CL domain | QPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPT ECS | 32 |
| Human IgG1 heavy chain constant region (CH1-CH2-CH3) | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR DELTKNQVSLTCLVKGFYPSDIAVEWESNGQPEN NYKTTPPVLDSDGSFFLYSKLTVDKSRWQQGNVF SCSVMHEALHNHYTQKSLSLSP | 33 |
| Murine surrogate PD-1 IL2v - HC with IL2v | EVQLQESGPGLVKPSQSLSLTCSVTGYSITSSYR WNWIRKFPGNRLEWMGYINSAGISNYNPSLKRRI SITRDTSKNQFFLQVNSVTTEDAATYYCARSDNM GTTPFTYWGQGTLVTVSSAKTTPPSVYPLAPGSA AQTNSMVTLGCLVKGYFPEPVTVTWNSGSLSSGV HTFPAVLQSDLYTLSSSVTVPSSTWPSQTVTCNV AHPASSTKVDKKIVPRDCGCKPCICTVPEVSSVF IFPPKPKDVLTITLTPKVTCVVVAISKDDPEVQF SWFVDDVEVHTAQTKPREEQINSTFRSVSELPIM HQDWLNGKEFKCRVNSAAFGAPIEKTISKTKGRP KAPQVYTIPPPKEQMAKDKVSLTCMITNFFPEDI TVEWQWNGQPAENYDNTQPIMDTDGSYFVYSDLN VQKSNWEAGNTFTCSVLHEGLHNHHTEKSLSHSP GGGGGSGGGGSGGGGSAPASSSTSSSTAEAQQQQ QQQQQQQQHLEQLLMDLQELLSRMENYRNLKLPR MLTAKFALPKQATELKDLQCLEDELGPLRHVLDG TQSKSFQLEDAENFISNIRVTVVKLKGSDNTFEC QFDDESATVVDFLRRWIAFAQSIISTSPQ | 34 |
| Murine surrogate PD-1 IL2v - HC without IL2v | EVQLQESGPGLVKPSQSLSLTCSVTGYSITSSYR WNWIRKFPGNRLEWMGYINSAGISNYNPSLKRRI SITRDTSKNQFFLQVNSVTTEDAATYYCARSDNM GTTPFTYWGQGTLVTVSSAKTTPPSVYPLAPGSA AQTNSMVTLGCLVKGYFPEPVTVTWNSGSLSSGV HTFPAVLQSDLYTLSSSVTVPSSTWPSQTVTCNV AHPASSTKVDKKIVPRDCGCKPCICTVPEVSSVF IFPPKPKDVLTITLTPKVTCVWAISKDDPEVQFS WFVDDVEVHTAQTKPREEQINSTFRSVSELPIMH QDWLNGKEFKCRVNSAAFGAPIEKTISKTKGRPK APQVYTIPPPKKQMAKDKVSLTCMITNFFPEDIT VEWQWNGQPAENYKNTQPIMKTDGSYFVYSKLNV QKSNWEAGNTFTCSVLHEGLHNHHTEKSLSHSP | 35 |
| Murine surrogate PD-1 IL2v - LC | DIVMTQGTLPNPVPSGESVSITCRSSKSLLYSDG KTYLNWYLQRPGQSPQLLIYWMSTRASGVSDRFS GSGSGTDFTLKISGVEAEDVGIYYCQQGLEFPTF GGGTKLELKRTDAAPTVSIFPPSSEQLTSGGASV | 36 |

| | AMINO ACID SEQUENCE | SEQ ID NO |
|---|---|---|
| | VCFLNNFYPKDINVKWKIDGSERQNGVLNSWTDQ DSKDSTYSMSSTLTLTKDEYERHNSYTCEATHKT STSPIVKSFNRNEC | |
| PD-L1 IL2v - HC with IL2v (Fc knob, LALAPG) | EVQLVESGGGLVQPGGSLRLSCAASGFTFSDSWI HWVRQAPGKGLEWVAWISPYGGSTYYADSVKGRF TISADTSKNTAYLQMNSLRAEDTAVYYCARRHWP GGFDYWGQGTLVTVSAASTKGPSVFPLAPSSKST SGGTAALGCLVKDYFPEPVTVSWNSGALTSGVHT FPAVLQSSGLYSLSSWTVPSSSLGTQTYICNVNH KPSNTKVDKKVEPKSCDKTHTCPPCPAPEAAGGP SVFLFPPKPKDTLMISRTPEVTCVVVDVSHEDPE VKFNWYVDGVEVHNAKTKPREEQYNSTYRVVSVL TVLHQDWLNGKEYKCKVSNKALGAPIEKTISKAK GQPREPQVYTLPPCRDELTKNQVSLWCLVKGFYP SDIAVEWESNGQPENNYKTTPPVLDSDGSFFLYS KLTVDKSRWQQGNVFSCSVMHEALHNHYTQKSLS LSPGGGGSGGGGSGGGGSAPASSSTKKTQLQLE HLLLDLQMILNGINNYKNPKLTRMLTAKFAMPKK ATELKHLQCLEEELKPLEEVLNGAQSKNFHLRPR DLISNINVIVLELKGSETTFMCEYADETATIVEF LNRWITFAQSIISTLT | 37 |
| PD-L1 IL2v - HC without IL2v (Fc hole, LALAPG) | EVQLVESGGGLVQPGGSLRLSCAASGFTFSDSWI HWVRQAPGKGLEWVAWISPYGGSTYYADSVKGRF TISADTSKNTAYLQMNSLRAEDTAVYYCARRHWP GGFDYWGQGTLVTVSAASTKGPSVFPLAPSSKST SGGTAALGCLVKDYFPEPVTVSWNSGALTSGVHT FPAVLQSSGLYSLSSWTVPSSSLGTQTYICNVNH KPSNTKVDKKVEPKSCDKTHTCPPCPAPEAAGGP SVFLFPPKPKDTLMISRTPEVTCVVVDVSHEDPE VKFNWYVDGVEVHNAKTKPREEQYNSTYRVVSVL TVLHQDWLNGKEYKCKVSNKALGAPIEKTISKAK GQPREPQVCTLPPSRDELTKNQVSLSCAVKGFYP SDIAVEWESNGQPENNYKTTPPVLDSDGSFFLVS KLTVDKSRWQQGNVFSCSVMHEALHNHYTQKSLS LSP | 38 |
| PD-L1 IL2v - LC | DIQMTQSPSSLSASVGDRVTITCRASQDVSTAVA WYQQKPGKAPKLLIYSASFLYSGVPSRFSGSGSG TDFTLTISSLQPEDFATYYCQQYLYHPATFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | 39 |
| Murine surrogate PD-L1 IL2v - HC with IL2v | EVQLVESGGGLVQPGGSLRLSCAASGFTFSDSWI HWVRQAPGKGLEWVAWISPYGGSTYYADSVKGRF TISADTSKNTAYLQMNSLRAEDTAVYYCARRHWP GGFDYWGQGTLVTVSAAKTTPPSVYPLAPGSAAQ TNSMVTLGCLVKGYFPEPVTVTWNSGSLSSGVHT FPAVLQSDLYTLSSSVTVPSSTWPSETVTCNVAH PASSTKVDKKIVPRDCGCKPCICTVPEVSSVFIF PPKPKDVLTITLTPKVTCVVVAISKDDPEVQFSW FVDDVEVHTAQTQPREEQFNSTFRSVSELPIMHQ DWLNGKEFKCRVNSAAFGAPIEKTISKTKGRPKA PQVYTIPPPKEQMAKDKVSLTCMITDFFPEDITV EWQWNGQPAENYDNTQPIMDTDGSYFVYSDLNVQ KSNWEAGNTFTCSVLHEGLHNHHTEKSLSHSPGG GGGSGGGGSGGGGSAPASSSTSSSTAEAQQQQQQ QQQQQQHLEQLLMDLQELLSRMENYRNLKLPRML TAKFALPKQATELKDLQCLEDELGPLRHVLDGTQ SKSFQLEDAENPISNIRVTVVKLKGSDNTFECQF DDESATVVDFLRRWIAFAQSIISTSPQ | 40 |
| Murine surrogate PD-L1 IL2v - HC without IL2v | EVQLVESGGGLVQPGGSLRLSCAASGFTFSDSWI HWVRQAPGKGLEWVAWISPYGGSTYYADSVKGRF TISADTSKNTAYLQMNSLRAEDTAVYYCARRHWP GGFDYWGQGTLVTVSAAKTTPPSVYPLAPGSAAQ TNSMVTLGCLVKGYFPEPVTVTWNSGSLSSGVHT FPAVLQSDLYTLSSSVTVPSSTWPSETVTCNVAH PASSTKVDKKIVPRDCGCKPCICTVPEVSSVFIF PPKPKDVLTITLTPKVTCVVVAISKDDPEVQFSW FVDDVEVHTAQTQPREEQFNSTFRSVSELPIMHQ | 41 |

| | AMINO ACID SEQUENCE | SEQ ID NO |
|---|---|---|
| | DWLNGKEFKCRVNSAAFGAPIEKTISKTKGRPKA PQVYTIPPPKKQMAKDKVSLTCMITDFFPEDITV EWQWNGQPAENYKNTQPIMKTDGSYFVYSKLNVQ KSNWEAGNTFTCSVLHEGLHNHHTEKSLSHSP | |
| Murine surrogate PD-L1 IL2v - LC | DIQMTQSPSSLSASVGDRVTITCRASQDVSTAVA WYQQKPGKAPKLLIYSASFLYSGVPSRFSGSGSG TDFTLTISSLQPEDFATYYCQQYLYHPATFGQGT KVEIKRADAAPTVSIFPPSSEQLTSGGASVVCFL NNFYPKDINVKWKIDGSERQNGVLNSWTDQDSKD STYSMSSTLTLTKDEYERHNSYTCEATHKTSTSP IVKSFNRNEC | 42 |
| hPD-1 Extracellular Domain (ECD) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTYL CGAISLAPKAQIKESLRAELRVTERRAEVPTAHP SPSPRPAGQFQTLV | 43 |
| muCEA HC-Fc (DD) - muIL2v | QVQLVQSGAEVKKPGASVKVSCKASGYTFTEFGM NWVRQAPGQGLEWMGWINTKTGEATYVEEFKGRV TFTTDTSTSTAYMELRSLRSDDTAVYYCARWDFA YYVEAMDYWGQGTTVTVSSAKTTPPSVYPLAPGS AAQTNSMVTLGCLVKGYFPEPVTVTWNSGSLSSG VHTFPAVLQSDLYTLSSSVTVPSSTWPSQTVTCN VAHPASSTKVDKKIVPRDCGCKPCICTVPEVSSV FIFPPPKPKDVLTITLTPKVTCVVVAISKDDPEVQ FSWFVDDVEVHTAQTKPREEQINSTFRSVSELPI MHQDWLNGKEFKCRVNSAAFGAPIEKTISKTKGR PKAPQVYTIPPPKEQMAKDKVSLTCMITNFFPED ITVEWQWNGQPAENYDNTQPIMDTDGSYFVYSDL NVQKSNWEAGNTFTCSVLHEGLHNHHTEKSLSHS PGGGGGSGGGGSGGGGSAPASSSTSSSTAEAQQQ QQQQQQQQHLEQLLMDLQELLSRMENYRNLKLP RMLTAKFALPKQATELKDLQCLEDELGPLRHVLD GTQSKSFQLEDAENFISNIRVTVVKLKGSDNTFE CQFDDESATVVDFLRRWIAFAQSIISTSPQ | 44 |
| muCEA HC-Fc (KK) - muIL2v | QVQLVQSGAEVKKPGASVKVSCKASGYTFTEFGM NWVRQAPGQGLEWMGWINTKTGEATYVEEFKGRV TFTTDTSTSTAYMELRSLRSDDTAVYYCARWDFA YYVEAMDYWGQGTTVTVSSAKTTPPSVYPLAPGS AAQTNSMVTLGCLVKGYFPEPVTVTWNSGSLSSG VHTFPAVLQSDLYTLSSSVTVPSSTWPSQTVTCN VAHPASSTKVDKKIVPRDCGCKPCICTVPEVSSV FIFPPPKPKDVLTITLTPKVTCVVVAISKDDPEVQ FSWFVDDVEVHTAQTKPREEQINSTFRSVSELPI MHQDWLNGKEFKCRVNSAAFGAPIEKTISKTKGR PKAPQVYTIPPPKKQMAKDKVSLTCMITNFFPED ITVEWQWNGQPAENYKNTQPIMKTDGSYFVYSKL NVQKSNWEAGNTFTCSVLHEGLHNHHTEKSLSHS PGK | 45 |
| muCEA LC | DIQMTQSPSSLSASVGDRVTITCKASAAVGTYVA WYQQKPGKAPKLLIYSASYRKRGVPSRFSGSGSG TDFTLTISSLQPEDFATYYCHQYYTYPLFTFGQG TKLEIKRADAAPTVSIFPPSSEQLTSGGASVVCF LNNFYPKDINVKWKIDGSERQNGVLNSWTDQDSK DSTYSMSSTLTLTKDEYERHNSYTCEATHKTSTS PIVKSFNRNEC | 46 |
| muFAP HC-Fc (DD) - muIL2v | EVQLLESGGGLVQPGGSLRLSCAASGFTFSSYAM SWVRQAPGKGLEWVSAIIGSGASTYYADSVKGRF TISRDNSKNTLYLQMNSLRAEDTAVYYCAKGWFG GFNYWGQGTLVTVSSAKTTPPSVYPLAPGSAAQT NSMVTLGCLVKGYFPEPVTVTWNSGSLSSGVHTF PAVLQSDLYTLSSSVTVPSSTWPSQTVTCNVAHP ASSTKVDKKIVPRDCGCKPCICTVPEVSSVFIFP PKPKDVLTITLTPKVTCVVVAISKDDPEVQFSWF VDDVEVHTAQTKPREEQINSTFRSVSELPIMHQD WLNGKEFKCRVNSAAFGAPIEKTISKTKGRPKAP QVYTIPPPKEQMAKDKVSLTCMITNFFPEDITVE WQWNGQPAENYDNTQPIMDTDGSYFVYSDLNVQK SNWEAGNTFTCSVLHEGLHNHHTEKSLSHSPGGG GGSGGGGSGGGGSAPASSSTSSSTAEAQQQQQQQ QQQQQHLEQLLMDLQELLSRMENYRNLKLPRMLT | 47 |

| | AMINO ACID SEQUENCE | SEQ ID NO |
|---|---|---|
| | AKFALPKQATELKDLQCLEDELGPLRHVLDGTQS KSFQLEDAENFISNIRVTVVKLKGSDNTFECQFD DESATVVDFLRRWIAFAQSIISTSPQ | |
| muFAP HC-Fc (KK) | EVQLLESGGGLVQPGGSLRLSCAASGFTFSSYAM SWVRQAPGKGLEWVSAIIGSGASTYYADSVKGRF TISRDNSKNTLYLQMNSLRAEDTAVYYCAKGWFG GFNYWGQGTLVTVSSAKTTPPSVYPLAPGSAAQT NSMVTLGCLVKGYFPEPVTVTWNSGSLSSGVHTF PAVLQSDLYTLSSSVTVPSSTWPSQTVTCNVAHP ASSTKVDKKIVPRDCGCKPCICTVPEVSSVFIFP PKPKDVLTITLTPKVTCVVVAISKDDPEVQFSWF VDDVEVHTAQTKPREEQINSTFRSVSELPIMHQD WLNGKEFKCRVNSAAFGAPIEKTISKTKGRPKAP QVYTIPPPKKQMAKDKVSLTCMITNFFPEDITVE WQWNGQPAENYKNTQPIMKTDGSYFVYSKLNVQK SNWEAGNTFTCSVLHEGLHNHHTEKSLSHSPGK | 48 |
| muFAP LC | EIVLTQSPGTLSLSPGERATLSCRASQSVTSSYL AWYQQKPGQAPRLLINVGSRRATGIPDRFSGSGS GTDFTLTISRLEPEDFAVYYCQQGIMLPPTFGQG TKVEIKRADAAPTVSIFPPSSEQLTSGGASVVCF LNNFYPKDINVKWKIDGSERQNGVLNSWTDQDSK DSTYSMSSTLTLTKDEYERHNSYTCEATHKTSTS PIVKSFNRNEC | 49 |
| anti-muPD1-HC_mIgG2a-LALAPG | EVQLQESGPGLVKPSQSLSLTCSVTGYSITSSYR WNWIRKFPGNRLEWMGYINSAGISNYNPSLKRRI SITRDTSKNQFFLQVNSVTTEDAATYYCARSDNM GTTPFTYWGQGTLVTVSSASTTAPSVYPLAPVCG DTTGSSVTLGCLVKGYFPEPVTLTWNSGSLSSGV HTFPAVLQSDLYTLSSSVTVTSSTWPSQSITCNV AHPASSTKVDKKIEPRGPTIKPCPPCKCPAPNAA GGPSVFIFPPKIKDVLMISLSPIVTCVVVDVSED DPDVQISWFVNNVEVHTAQTQTHREDYNSTLRVV SALPIQHQDWMSGKEFKCKVNNKDLGAPIERTIS KPKGSVRAPQVYVLPPPEEEMTKKQVTLTCMVTD FMPEDIYVEWTNNGKTELNYKNTEPVLDSDGSYF MYSKLRVEKKNWVERNSYSCSVVHEGLHNHHTTK SFSRTPGK | 50 |
| anti muPD1-LC | DIVMTQGTLPNPVPSGESVSITCRSSKSLLYSDG KTYLNWYLQRPGQSPQLLIYWMSTRASGVSDRFS GSGSGTDFTLKISGVEAEDVGIYYCQQGLEFPTF GGGTKLELKRTDAAPTVSIFPPSSEQLTSGGASV VCFLNNFYPKDINVKWKIDGSERQNGVLNSWTDQ DSKDSTYSMSSTLTLTKDEYERHNSYTCEATHKT STSPIVKSFNRNEC | 51 |

EXAMPLES

The following are examples of methods and compositions of the invention. It is understood that various other embodiments may be practiced, given the general description provided above.

Example 1

Example 1A. Preparation of PD1-IL2V Fusion Proteins

The expression cassette for the antibody heavy chain-interleukin-2 (IL-2) fusion protein [heavy chain variable region of anti-human PD-1 antibody, human IgG$_1$ heavy chain (bearing mutations L234A, L235A and P329G (EU numbering) for removal of effector functions, and mutations S354C and T366W (EU numbering) for heterodimerization ("knob")), (G$_4$S)$_3$ linker, and human IL-2v (bearing the mutations T3A, F42A, Y45A, L72G and C125A)], the expression cassette for the antibody heavy chain [heavy chain variable region of anti-human PD-1 antibody, and human IgG$_1$ heavy chain (bearing mutations L234A, L235A and P329G (EU numbering) for removal of effector functions, mutations Y349C, T366S, L368A and Y410V (EU numbering) for heterodimerization ("hole"), and optionally mutations H435R and Y436F (EU numbering)] and the expression cassette for the antibody light chain [light chain variable region of anti-human PD-1 antibody, and human C$_{kappa}$ constant region] and was produced by gene-synthesis.

They were each cloned via HindIII and NheI digestion into an expression vector under the control of the CMV-promoter followed by IntronA and terminated by BGH-poly A signal. The vector further contained a bacterial ampicillin resistance gene and an origin of replication from *E. coli*.

The human PD1-IL-2v fusion protein (SEQ ID NOs 22, 24 and 25) was generated by cotransfection of HEK293F cells (Invitrogen) with the above-described vectors in the ratio of 1:1:1 in shaking flasks. After one week supernatant was harvested and filtrated through sterile filters.

The fusion protein was purified from the supernatant by a combination of Protein A affinity chromatography and size exclusion chromatography. The obtained product was characterized for identity by mass spectrometry and analytical properties such as purity by capillary electrophoresis (CE-SDS), monomer content and stability.

The murine surrogate PD1-IL2v fusion protein (SEQ ID NOs 34-36) was produced analogously. The surrogate molecule comprises a murine IgG1 anti-mouse PD-1 antibody (bearing Fc mutations for removal of effector function and for heterodimerization) and murine interleukin-2 with analogous mutations to the human molecule.

Both fusion proteins could be produced in good yields and are stable.

Example 1B. Preparation of Pd-L1-IL2V Fusion Proteins

The expression cassette for the antibody heavy chain-interleukin-2 (IL-2) fusion protein [heavy chain variable region of anti-human PD-L1 antibody, human IgG$_1$ heavy chain (bearing mutations L234A, L235A and P329G (EU numbering) for removal of effector functions, and mutations S354C and T366W (EU numbering) for heterodimerization ("knob")), (G$_4$S)$_3$ linker, and human IL-2v (bearing the mutations T3A, F42A, Y45A, L72G and C125A)], the expression cassette for the antibody heavy chain [heavy chain variable region of anti-human PD-L1 antibody, and human IgG$_1$ heavy chain (bearing mutations L234A, L235A and P329G (EU numbering) for removal of effector functions, mutations Y349C, T366S, L368A and Y410V (EU numbering) for heterodimerization ("hole"))], and the expression cassette for the antibody light chain [light chain variable region of anti-human PD-L1 antibody, and human C$_{kappa}$ constant region] were produced by gene-synthesis. The antibody expression was driven by a chimeric MPSV promoter and a synthetic polyA signal sequence was located at the 3' end of the CDS. In addition each vector contained an EBV OriP sequence.

The molecules were produced by co-transfecting HEK293-EBNA cells growing in suspension with the mammalian expression vectors using polyethylenimine. The cells were transfected with the corresponding expression vectors in a 1:1:2 ratio ("vector heavy chain (VH-CH1-CH2-CH3-IL2v)": "vector heavy chain (VH-CH1-CH2-CH3)": "vector light chain (VL-CL)").

For transfection HEK293 EBNA cells are cultivated in suspension in serum free Excell culture medium containing 6 mM L-glutamine and 250 mg/l G418 culture medium. For the production in 600 ml tubespin flasks (max. working volume 400 mL) 600 million HEK293 EBNA cells were seeded 24 hours before transfection. For transfection, cells were centrifuged for 5 min by 210×g, and supernatant was replaced by 20 ml pre-warmed CD CHO medium. Expression vectors were mixed in 20 ml CD CHO medium to a final amount of 400 µg DNA. After addition of 1080 µl PEI solution (2.7 µg/ml), the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% CO$_2$ atmosphere. After the incubation time 360 ml Excell+6 mM L-glutamine+5 g/L Pepsoy+1.0 mM VPA medium were added and cells were cultivated for 24 hours. One day after transfection 7% Feed 7 was added. After 7 days cultivation, supernatant was collected for purification by centrifugation for 20-30 min at 3600×g (Sigma 8K centrifuge), the solution was sterile filtered (0.22 mm filter) and sodium azide in a final concentration of 0.01% (w/v) was added. The solution was kept at 4° C.

The human PD-L1-IL2v construct (SEQ ID NOs 37-39) was purified by one affinity step with proteinA (MabSelectSure, GE Healthcare) followed by size exclusion chromatography (HiLoad 16/60 Superdex 200, GE Healthcare). For affinity chromatography supernatant was loaded on a HiTrap ProteinA HP column (CV=5 mL, GE Healthcare) equilibrated with 25 ml 20 mM sodium phosphate, 20 mM sodium citrate, pH 7.5. Unbound protein was removed by washing with at least 10 column volumes 20 mM sodium phosphate, 20 mM sodium citrate, pH 7.5 and target protein was eluted in 6 column volumes 20 mM sodium citrate, 100 mM sodium chloride, 100 mM glycine, 0.01% Tween20 pH 3.0. Protein solution was neutralized by adding 1/10 of 0.5M sodium phosphate, pH 8.0. Target protein was concentrated and filtered prior to loading on a HiLoad Superdex 200 column (GE Healthcare) equilibrated with 20 mM histidine, 140 mM sodium chloride, pH 6.0, 0.01% Tween20.

The murine PD-L1-IL2v construct (SEQ ID NOs 40-42) was likewise purified by one affinity step with proteinA (MabSelectSure, GE Healthcare) followed by size exclusion chromatography (HiLoad 16/60 Superdex 200, GE Healthcare). For affinity chromatography supernatant was mixed 1:1 with 2 M glycine, 0.6 M NaCl pH 8.6 and loaded on a HiTrap ProteinA HP column (CV=5 mL, GE Healthcare) equilibrated with 25 ml 1 M glycine, 0.3 M NaCl pH 8.6. Unbound protein was removed by washing with at least 10 column volumes of 1 M glycine, 0.3 M NaCl pH 8.6 and target protein was eluted in 6 column volume of 1 M glycine, 0.3 M NaCl pH 4.0. Protein solution was neutralized by adding 1/10 of 0.5 M sodium phosphate, pH 8.0. Target protein was concentrated and filtered prior to loading on a HiLoad Superdex 200 column (GE Healthcare) equilibrated with 20 mM histidine, 140 mM sodium chloride, pH 6.0, 0.01% Tween20.

The final preparation of human PD-L1-IL2v contained 99% monomer (determined on a TSKgel G3000 SW XL analytical size-exclusion column (Tosoh) in 25 mM K$_2$HPO$_4$, 125 mM NaCl, 200 mM L-arginine monohydrochloride, 0.02% (w/v) NaN$_3$, pH 6.7 running buffer at 25° C.) and had 100% purity (determined by non-reduced SDS capillary electrophoresis on a Caliper LabChip GXII system (Caliper lifescience) used according to the manufacturer's instruction). The production yield was 23 mg/L. Mass spectrometry analysis revealed a mostly correctly assembled molecule with traces (<5%) of molecules without interleukin-2 (mass spectrometry performed on an Agilent LC-MS system (Agilent Technologies) with a NUCLEOGEL RP1000-8, 250 mm×4.6 mm column (MACHEREY-NAGEL GmbH) and an acetonitrile-formic acid gradient).

For the murine surrogate PD-L1-IL2v, the monomer content was of 96%, the purity 100% and the production yield 3.8 mg/L.

Example 1C. Preparation of Murine Surrogate CEA-IL2V and Murine Surrogate Fap-IL2V A murinized surrogate molecule of the CEA-targeted IL-2 variant immunocytokine CEA-IL2v, termed muCEA-muIL2v (also termed muCEA-IL2v), was generated for use in vivo tumor models in fully immunocompetent mice in order to reduce the formation of anti-drug antibodies (ADA). In addition, a murinized chimeric version of the FAP-targeted IL-2 variant immunocytokine FAP-IL2v, termed muFAP-muIL2v (also termed muFAP-IL2v), respectively, was generated for use in vivo tumor models in fully immunocompetent mice in order to reduce the formation of anti-drug antibodies (ADA). In the murinized surrogate molecules, the Fc domain knob-into-holes mutations were replaced by DDKK mutations on muIgG1 and the LALA P329G mutations were replaced by DAPG mutations on muIgG1 (as disclosed in PCT application WO 2016/0330350 A1, which is incorporated by reference in its entirety).

For example, muCEA-muIL2v is characterized by the following features. As parental antibody a human-mouse chimeric IgG1 antibody is applied with human(ized) variable regions, but murine constant regions. In order to avoid potential immunogenicity the corresponding Black 6 allotype was used (sequence published by Mouse Genomes Project). Binding to muIL2Ru was abolished by three mutations homologous to those identified in human IL-2v and the respective O-glycosylation site was removed: T23A (O-Glyco), F76A, Y79A, L106G. In addition, like in aldesleukin the cysteine residue was mutated to avoid aggregation by a C160A mutation (numbering based on UniProt ID P04351 including the signal peptide). Although muIgG1 already has reduced FcγR binding, binding to murine FcγRs was completely abolished by introduction of the DAPG mutations (D265A, P329G), while muFcRn binding is retained. muIL-2v was fused via a non-immunogenic (G4S)$_2$-connector only to the C-terminus of one heavy chain of the muIgG1 antibody. In order to achieve this, the immunocytokine was engineered using electrostatic steering via DDKK mutations in the Fc domain to allow heterodimerization in the mouse background.

The polypeptide sequences of muCEA-muIL2v are as follows:

```
Heavy chain with DD mutation and with
fused muIL2v (SEQ ID NO: 44):
QVQLVQSGAEVKKPGASVKVSCKASGYTFTEFGMNWVRQAPGQGLEWMGW

INTKTGEATYVEEFKGRVTFTTDTSTSTAYMELRSLRSDDTAVYYCARWD

FAYYVEAMDYWGQGTTVTVSSAKTTPPSVYPLAPGSAAQTNSMVTLGCLV

KGYFPEPVTVTWNSGSLSSGVHTFPAVLQSDLYTLSSSVTVPSSTWPSQT

VTCNVAHPASSTKVDKKIVPRDCGCKPCICTVPEVSSVFIFPPKPKDVLT

ITLTPKVTCVVVAISKDDPEVQFSWFVDDVEVHTAQTKPREEQINSTFRS

VSELPIMHQDWLNGKEFKCRVNSAAFGAPIEKTISKTKGRPKAPQVYTIP

PPKEQMAKDKVSLTCMITNFFPEDITVEWQWNGQPAENYDNTQPIMDTDG

SYFVYSDLNVQKSNWEAGNTFTCSVLHEGLHNHHTEKSLSHSPGGGGSG

GGGSGGGGSAPASSSTSSSTAEAQQQQQQQQQQQHLEQLLMDLQELLSR

MENYRNLKLPRMLTAKFALPKQATELKDLQCLEDELGPLRHVLDGTQSKS

FQLEDAENFISNIRVTVVKLKGSDNTFECQFDDESATVVDFLRRWIAFAQ

SIISTSPQ

Heavy chain with KK mutation
(SEQ ID NO: 45):
QVQLVQSGAEVKKPGASVKVSCKASGYTFTEFGMNWVRQAPGQGLEWMGW

INTKTGEATYVEEFKGRVTFTTDTSTSTAYMELRSLRSDDTAVYYCARWD

FAYYVEAMDYWGQGTTVTVSSAKTTPPSVYPLAPGSAAQTNSMVTLGCLV

KGYFPEPVTVTWNSGSLSSGVHTFPAVLQSDLYTLSSSVTVPSSTWPSQT

VTCNVAHPASSTKVDKKIVPRDCGCKPCICTVPEVSSVFIFPPKPKDVLT

ITLTPKVTCVVVAISKDDPEVQFSWFVDDVEVHTAQTKPREEQINSTFRS

VSELPIMHQDWLNGKEFKCRVNSAAFGAPIEKTISKTKGRPKAPQVYTIP

PPKKQMAKDKVSLTCMITNFFPEDITVEWQWNGQPAENYKNTQPIMKTDG

SYFVYSKLNVQKSNWEAGNTFTCSVLHEGLHNHHTEKSLSHSPGK

Light chain (SEQ ID NO: 46):
DIQMTQSPSSLSASVGDRVTITCKASAAVGTYVAWYQQKPGKAPKLLIYS

ASYRKRGVPSRFSGSGSGTDFTLTISSLQPEDFATYYCHQYYTYPLFTFG

QGTKLEIKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKSFNRNEC

The polypeptide sequences of muFAP-muIL2v
are as follows:
Heavy chain with DD mutation and with
fused muIL2v (SEQ ID NO: 47):
EVQLLESGGGLVQPGGSLRLSCAASGFTFSSYAMSWVRQAPGKGLEWVSA

IIGSGASTYYADSVKGRFTISRDNSKNTLYLQMNSLRAEDTAVYYCAKGW

FGGFNYWGQGTLVTVSSAKTTPPSVYPLAPGSAAQTNSMVTLGCLVKGYF

PEPVTVTWNSGSLSSGVHTFPAVLQSDLYTLSSSVTVPSSTWPSQTVTCN

VAHPASSTKVDKKIVPRDCGCKPCICTVPEVSSVFIFPPKPKDVLTITLT

PKVTCVVVAISKDDPEVQFSWFVDDVEVHTAQTKPREEQINSTFRSVSEL

PIMHQDWLNGKEFKCRVNSAAFGAPIEKTISKTKGRPKAPQVYTIPPPKE

QMAKDKVSLTCMITNFFPEDITVEWQWNGQPAENYDNTQPIMDTDGSYFV

YSDLNVQKSNWEAGNTFTCSVLHEGLHNHHTEKSLSHSPGGGGSGGGGS

GGGGSAPASSSTSSSTAEAQQQQQQQQQQQHLEQLLMDLQELLSRMENY

RNLKLPRMLTAKFALPKQATELKDLQCLEDELGPLRHVLDGTQSKSFQLE

DAENFISNIRVTVVKLKGSDNTFECQFDDESATVVDFLRRWIAFAQSIIS

TSPQ

Heavy chain with KK mutation
(SEQ ID NO: 48):
EVQLLESGGGLVQPGGSLRLSCAASGFTFSSYAMSWVRQAPGKGLEWVSA

IIGSGASTYYADSVKGRFTISRDNSKNTLYLQMNSLRAEDTAVYYCAKGW

FGGFNYWGQGTLVTVSSAKTTPPSVYPLAPGSAAQTNSMVTLGCLVKGYF

PEPVTVTWNSGSLSSGVHTFPAVLQSDLYTLSSSVTVPSSTWPSQTVTCN

VAHPASSTKVDKKIVPRDCGCKPCICTVPEVSSVFIFPPKPKDVLTITLT

PKVTCVVVAISKDDPEVQFSWFVDDVEVHTAQTKPREEQINSTFRSVSEL

PIMHQDWLNGKEFKCRVNSAAFGAPIEKTISKTKGRPKAPQVYTIPPPKK

QMAKDKVSLTCMITNFFPEDITVEWQWNGQPAENYKNTQPIMKTDGSYFV

YSKLNVQKSNWEAGNTFTCSVLHEGLHNHHTEKSLSHSPGK

Light chain (SEQ ID NO: 49):
EIVLTQSPGTLSLSPGERATLSCRASQSVTSSYLAWYQQKPGQAPRLLIN

VGSRRATGIPDRFSGSGSGTDFTLTISRLEPEDFAVYYCQQGIMLPPTFG

QGTKVEIKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKSFNRNEC
```

-continued

```
The polypeptide sequences of muPD1
are as follows:
Heavy chain (SEQ ID NO: 50):
EVQLQESGPGLVKPSQSLSLTCSVTGYSITSSYRWNWIRKFPGNRLEWMG

YINSAGISNYNPSLKRRISITRDTSKNQFFLQVNSVTTEDAATYYCARSD

NMGTTPFTYWGQGTLVTVSSASTTAPSVYPLAPVCGDTTGSSVTLGCLVK

GYFPEPVTLTWNSGSLSSGVHTFPAVLQSDLYTLSSSVTVTSSTWPSQSI

TCNVAHPASSTKVDKKIEPRGPTIKPCPPCKCPAPNAAGGPSVFIFPPKI

KDVLMISLSPIVTCVVVDVSEDDPDVQISWFVNNVEVHTAQTQTHREDYN

STLRVVSALPIQHQDWMSGKEFKCKVNNKDLGAPIERTISKPKGSVRAPQ

VYVLPPPEEEMTKKQVTLTCMVTDFMPEDIYVEWTNNGKTELNYKNTEPV

LDSDGSYFMYSKLRVEKKNWVERNSYSCSVVHEGLHNHHTTKSFSRTPGK

Light chain (SEQ ID NO: 51):
DIVMTQGTLPNPVPSGESVSITCRSSKSLLYSDGKTYLNWYLQRPGQSPQ

LLIYWMSTRASGVSDRFSGSGSGTDFTLKISGVEAEDVGIYYCQQGLEFP

TFGGGTKLELKRTDAAPTVSIFPPSSEQLTSGGASVVCFLNNFYPKDINV

KWKIDGSERQNGVLNSWTDQDSKDSTYSMSSTLTLTKDEYERHNSYTCEA

THKTSTSPIVKSFNRNEC
```

The immunoconjugates prepared in this Example were further used in the following Examples.

Example 2

Example 2A. Binding of PD1-IL2V to Activated CD8 and CD4 T Cells

Freshly isolated PBMCs from healthy human donors were stimulated overnight with CD3 and CD28 to induce upregulation of PD1 on T cells. PBMCs were seeded in medium (RPMI1640, 10% FCS, 2 mM Glutamine) into cell culture flasks that were coated for 1 h at 37° C. with 1 g/ml CD3 (clone OKT3, #317304, BioLegend). CD28 was added in solution to the PBMCs at a concentration of 2 µg/ml (clone CD28.2, #302914, BioLegend). On the next day PBMCs were harvested and transferred into a 96 well round bottom plate (200'000 cells per well). The cells were washed with FACS buffer (PBS, 2% FBS, 5 mM EDTA, 0.025% $NaN_3$) and stained with 40 µl of the indicated molecules (PD1 IgG, PD1-IL2v and CEA-IL2v) in FACS buffer for 30 min at 4° C. The cells were washed twice with FACS buffer to remove unbound molecules. Then 40 µl of the diluted PE anti-human Fc specific secondary antibody (#109-116-170, Jackson ImmunoResearch) was added to the cells. After 30 min incubation at 4° C. the cells were washed twice with FACS buffer. To detect T cells, PBMCs were stained with 40 µl of a mixture of CD3 FITC (clone UCHT1, #300406, BioLegend), CD4 APC (clone RPA-T4, 300514, BioLegend) and CD8 BV421 (clone RPA-T8, #301036, BioLegend) for 30 min at 4° C. The unbound antibodies were removed by washing twice with FACS buffer. Finally the cells were fixed with 1% PFA in FACS buffer and measured using a BD Fortessa gating on CD3+CD4+ cells (CD4 T cells) and CD3+CD8+ cells (CD8 T cells).

Figure 2A:
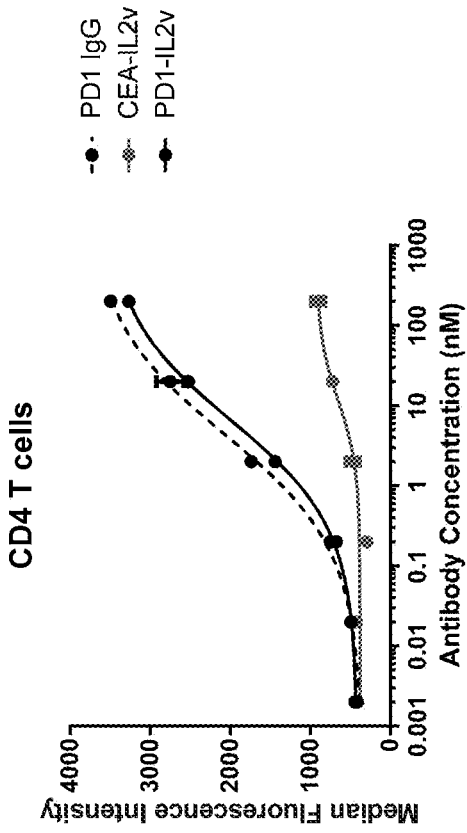
FIGS. 2A and 2B. Binding of PD1-IL2v to CD4 T cells (FIG. 2A) and CD8 T cells (FIG. 2B) within PHA activated PBMCs, in comparison to PD1 IgG and CEA-IL2v.
Figure 2B:
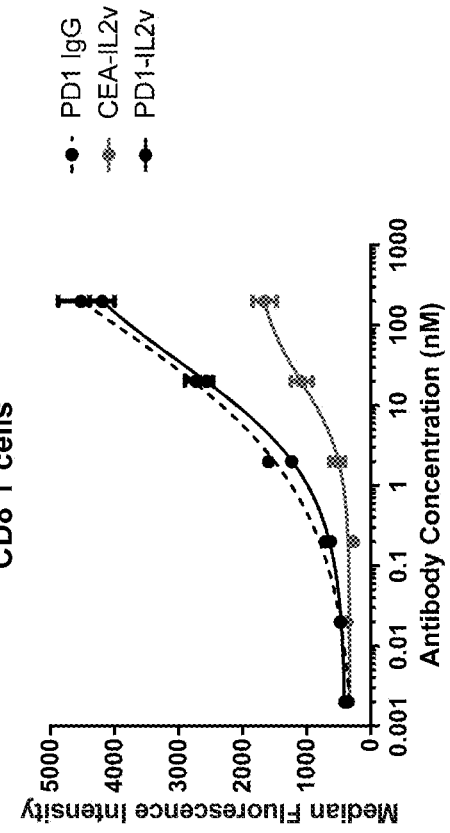

As shown in FIG. 2, PD1-IL2v and the corresponding PD1 IgG bind similarly to CD4 and CD8 T cells. An analogous immunocytokine: CEA-IL2v, targeted to CEA on tumor cells instead of PD1 served as an untargeted control to compare to the effect of IL2v based immunocytokine alone that are not targeted to PD1.

Example 2B. Activation and Proliferation of T Cells and Nk Cells with PD1-IL2V Freshly isolated PBMCs from healthy human donors were incubated overnight and then labeled with CFSE (5(6)-Carboxyfluorescein diacetate N-succinimidyl ester, #21888, Sigma-Aldrich). Briefly 30 million PBMCs were washed once with PBS. In parallel the CSFE stock solution (2 mM in DMSO) was diluted 1:20 in PBS. PBMCs were resuspended in 30 ml prewarmed PBS, 30 µl of the CFSE solution was added and the cells were mixed immediately. For an optimal labeling the cells were incubated for 15 min at 37° C. Then 10 ml prewarmed medium (RPMI1640, 10% FCS, 1% Glutamine) were added to stop the labeling reaction. The cells were spun down for 10 min at 400×g and resuspended in 20 ml fresh medium and incubated for additional 30 min at 37° C. Finally the cells were washed once with medium and resuspended in fresh medium at 1 million cells per ml. The labeled PBMCs were seeded in a 96 well round bottom plate (200'000 cells per well) and treated for 5 days with the indicated molecules (PD1-IL2v, CEA-IL2v, PD1 IgG, and the combination of PD1 IgG plus CEA-IL2v). After the incubation the cells were washed once with FACS buffer and stained with 20 µl of a mixture of CD3 APC/Cy7 (clone UCHT1, #300426, BioLegend), CD56 APC (clone HCH56, 3 #18310, BioLegend), CD4 PE (clone RPA-T4, #300508, BioLegend) and CD25 BV421 (clone M-A251, BioLegend) in FACS buffer for 30 min at 4° C. Afterwards PBMCs were washed twice with FACS buffer before fixing them with 1% PFA in FACS buffer and measuring the fluorescence with a BD Fortessa. Proliferation was determined by measuring CFSE dilution of CD8 T cells (CD3+CD4−), CD4 T cells (CD3+CD4+) and NK cells (CD3-CD56+).

Figure 3A:
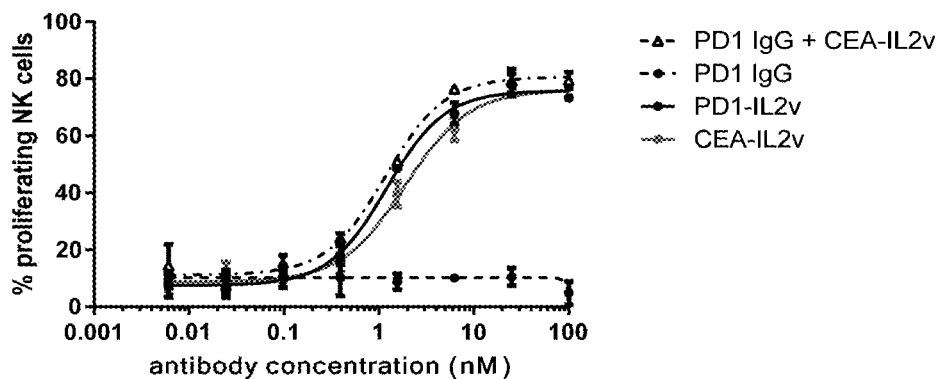
FIGS. 3A-3C. Proliferation of NK cells (FIG. 3A), CD8 T cells (FIG. 3B) and CD4 T cells (FIG. 3C) within PBMCs with PD1-IL2v, CEA-IL2v, and the combination of PD1 IgG plus CEA-IL2v. PD1 IgG was included as control.
Figure 3B:
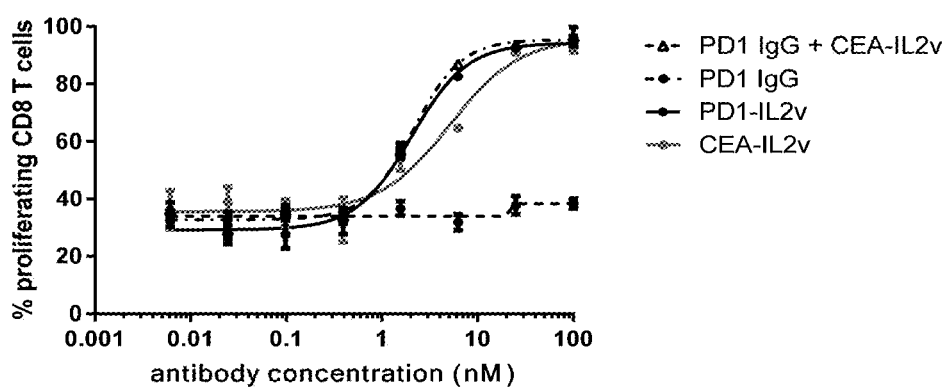
Figure 3C:
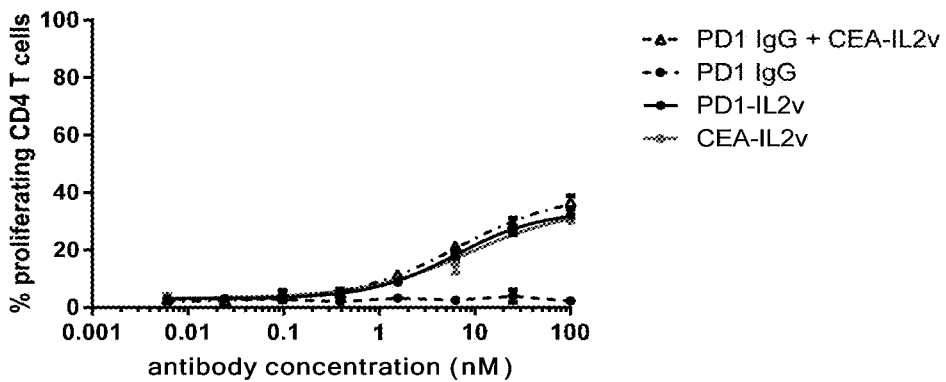

As shown in FIG. 3, the activity of PD1-IL2v is comparable to the activity of CEA-IL2v, and CEA-IL2v in combination with PD1 IgG. PD1 IgG alone has no activity in this setting.

FIG. 4 shows that PD1-IL2v induces activation (as measured by upregulation of CD25) of NK cells, CD8 T cells and CD4 T cells. The activation induced by CEA-IL2v and the combination of CEA-IL2v with PD1 IgG is similar. PD1 IgG alone does not induce activation in this setting.

Example 2C. Activation and Proliferation of Pre-Activated CD8 and CD4 T Cells with Pd1-IL2V Freshly isolated PBMCs from healthy human donors were labeled with CFSE (5(6)-Carboxyfluorescein diacetate N-succinimidyl ester, #21888, Sigma-Aldrich). Briefly 30 million PBMCs were washed once with PBS. In parallel the CSFE stock solution (2 mM in DMSO) was diluted 1:20 in PBS. PBMCs were resuspended in 30 ml prewarmed PBS, 30 µl of the CFSE solution was added and the cells were mixed immediately. For an optimal labeling the cells were incubated for 15 min at 37° C. Then 10 ml prewarmed medium (RPMI1640, 10% FCS, 1% Glutamine) were added to stop the labeling reaction. The cells were spun down for 10 min at 400×g and resuspended in 20 ml fresh medium and incubated for additional 30 min at 37° C. Finally the cells were washed once with medium and resuspended in fresh medium at 1 million cells per ml. The CFSE labeled PBMCs were pre-activated overnight with 1 µg/ml PHA (#L8902, Sigma-Aldrich) to induce upregulation of PD-1 on T cells.

On the next day the pre-activated PBMCs were collected and counted. The PBMCs were then seeded in a 96 well round bottom plate (200'000 cells per well) and treated for 4 days with the indicated molecules (PD1-IL2v, CEA-IL2v, PD1 gG, and the combination of PD1 gG plus CEA-IL2v). After the incubation the cells were washed once with FACS buffer and stained with 20 µl of a mixture of CD3 APC/Cy7 (clone UCHT1, #300426, BioLegend), CD8 APC (clone SKI, BioLegend) and CD25 BV421 (clone M-A251, BioLegend) in FACS buffer for 30 min at 4° C. Afterwards PBMCs were washed twice with FACS buffer before fixing them with 1% PFA in FACS buffer and measuring the fluorescence with a BD Fortessa. Proliferation was determined by measuring CFSE dilution of CD8 T cells (CD3+CD8+) and CD4 T cells (CD3+CD8−).

Figure 5A:
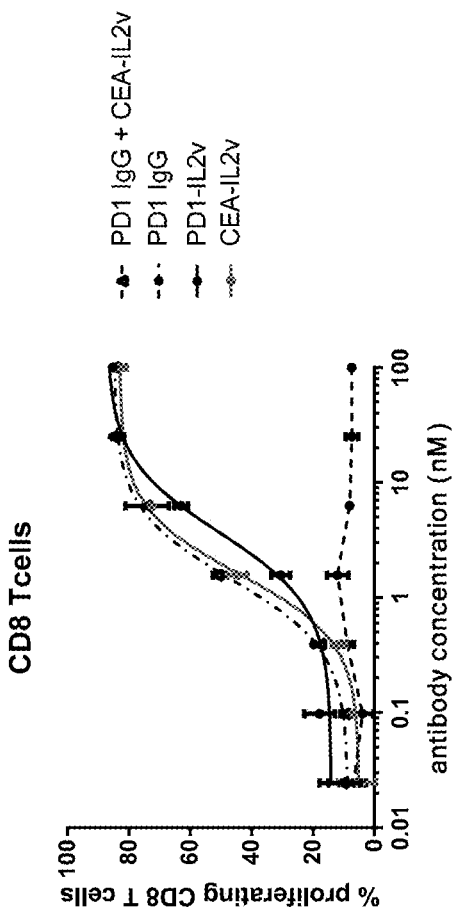
FIGS. 5A and 5B. Proliferation of PHA pre-activated CD8 T cells (FIG. 5A) and CD4 T cells (FIG. 5B) within PBMCs with PD1-IL2v, CEA-IL2v, and the combination of PD1 IgG plus CEA-IL2. PD1 IgG was included as control.
Figure 5B:
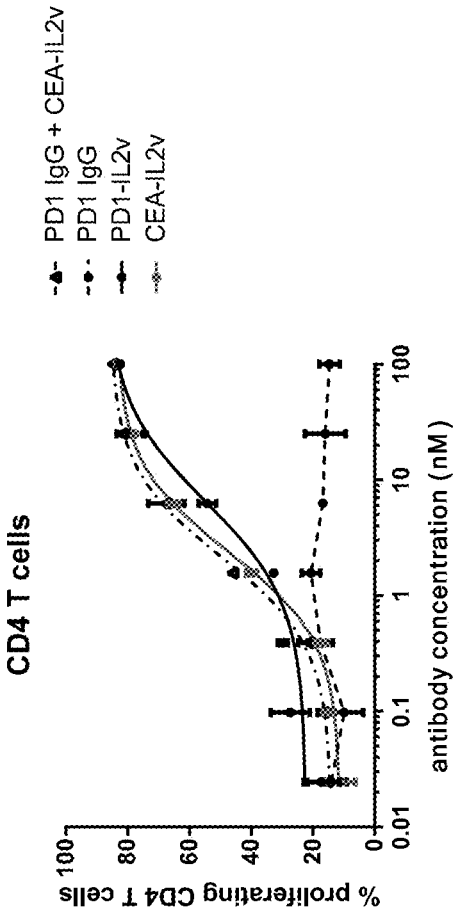

FIG. 5 shows that PD1-IL2v induces proliferation of PHA activated CD8 and CD4 T cells which express PD-1. The activity is comparable to CEA-IL2v and the combination of CEA-IL2v with PD1 IgG. PD1 IgG alone has no activity in this setting. No additional effect of PD-1 blocking can be observed in this setting probably due to the absence of PD-L1 positive tumor cells.

Figure 6A:
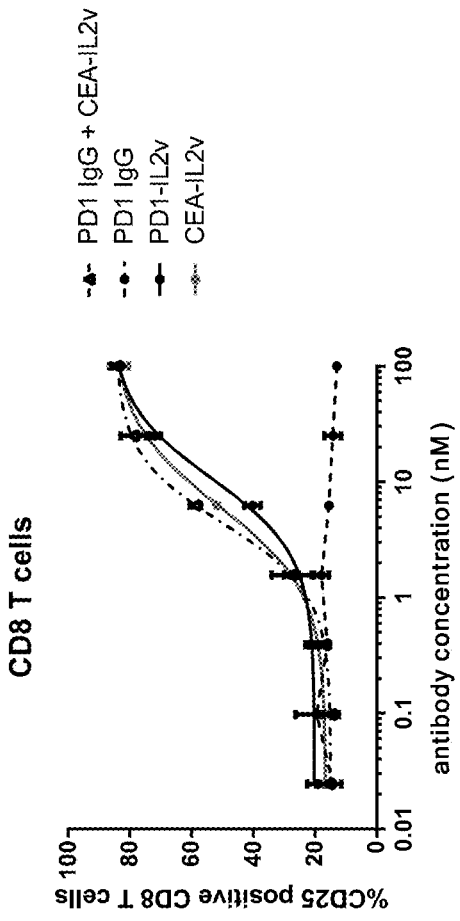
FIGS. 6A and 6B. Activation of PHA pre-stimulated CD8 T cells (FIG. 6A) and CD4 T cells (FIG. 6B) within PBMCs with PD1-IL2v, CEA-IL2v, and the combination of PD1 IgG plus CEA-IL2v. PD1 IgG was included as control. CD25 expression on CD4 T cells and CD8 T cells was used as a marker of activation.
Figure 6B:
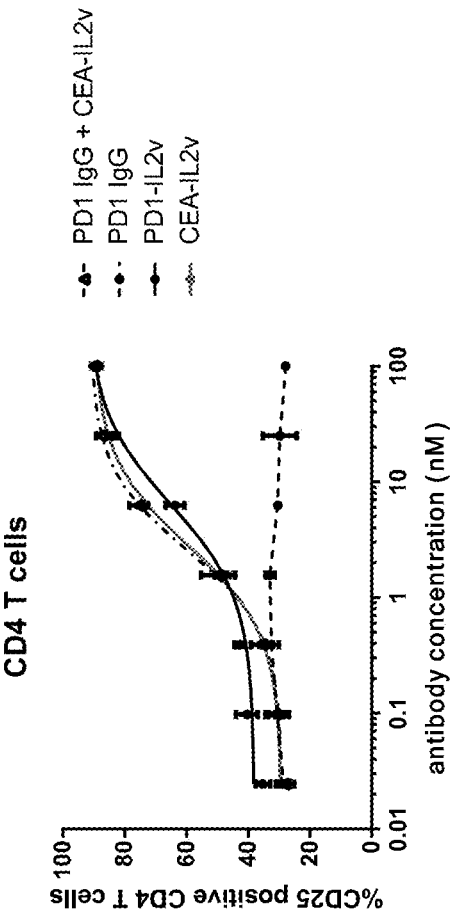

As shown in FIG. 6, PD1-IL2v induces activation of PHA activated CD8 and CD4 T cells which express PD-1 (using CD25 expression as a marker of activation). CEA-IL2v and the combination of CEA-IL2v with PD1 IgG induce a comparable activation of T cells. PD1 IgG alone has no activity in this setting. No additional effect of PD-1 blocking can be observed in this setting probably due to the absence of PD-L1 positive tumor cells.

Example 2D. Proliferation of NK92 with PD1-IL2v and PD-L1-IL2v

NK92 cells were harvested, counted and assessed for viability. Cells were washed three times with PBS to remove residual IL-2 and were re-suspended in medium (RPMI1640, 10% FCS, 1% Glutamine) without IL-2. The washed NK92 cells were incubated for two hours in cell incubator (IL-2 starvation). After starvation, cells were re-suspended in fresh medium without IL2- to 200,000 cells per ml and 50 µl of the cell suspension was transferred in a 96-well cell culture treated flat bottom plate and supplemented with 50 µl of the diluted antibodies (in medium without IL-2), Proleukin (1.5 µg/ml final concentration) or medium (control wells) to reach a final volume of 100 µl per well. The plate was incubated for 2 days in the incubator. After 2 days the CellTiter-Glo (Promega) reagents and the cell culture plate were equilibrated to room temperature. The CellTiter-Glo solution was prepared as described in the manufacturer's instructions and 100 µl of the solution was added to each well. After 10 min of incubation remaining aggregates were re-suspended by pipetting and 150 µl of the mixture was transferred to a white flat bottom plate. The luminescence was measured with Tecan Spark 10M multimode reader.

FIG. 7A shows that PD-L1-IL2v induces proliferation of NK92 cells as efficiently as CEA-IL2v.

FIG. 7B shows that PD-L1-IL2v and PD1-IL2v have the same activity in inducing proliferation of NK92 cells. NK92 cells are PD1 negative.

Example 2E. Binding of PD-L1-IL2V to CTLL2 Cells

The murine T cell line CTLL2 expresses PD-L1. These cells were used to test binding of PD-L1-IL2v (murine surrogate) to PD-L1. The cells were harvested, viability was checked and they were transferred into a 96 well round bottom plate (200'000 cells per well). The cells were washed with FACS buffer (PBS, 2% FBS, 5 mM EDTA, 0.025% $NaN_3$) and stained with 40 µl of the indicated molecules in FACS buffer for 30 min at 4° C. The cells were washed twice with FACS buffer to remove unbound molecules. Then 40 µl of the diluted APC anti-mouse Fc specific secondary antibody (#115-136-071, Jackson ImmunoResearch) was added to the cells. After 30 min incubation at 4° C. the cells were washed twice with FACS buffer. The cells were analyzed with a BD LSR Fortessa.

Figure 8:
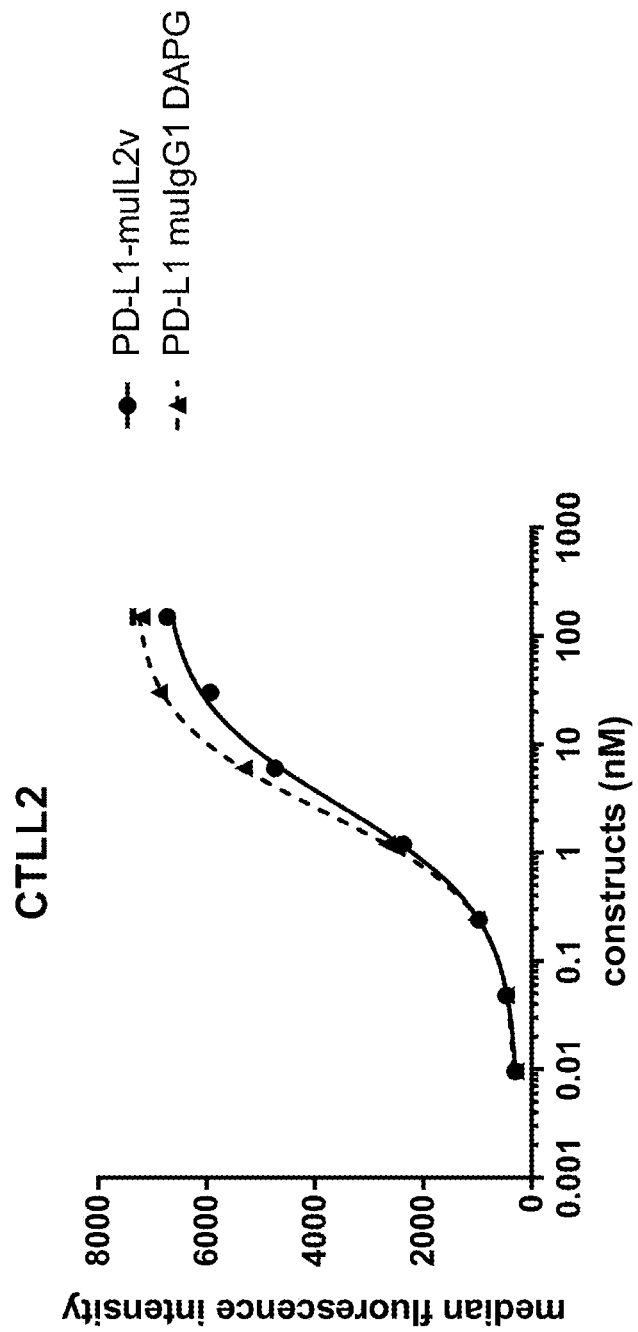
FIG. 8. Binding of PD-L1-muIL2v and PD-L1 muIgG1 to the PD-L1 positive mouse T cell line CTLL2.

FIG. 8 shows that PD-L1-IL2v binds as good as the corresponding PD-L1 muIgG1 to CTLL2 cells. These cells are PD1 negative.

Example 2F. Proliferation of CTLL2 Cells with PD1-IL2v and PD-L1-IL2v

CTLL2 cells were harvested, counted and assessed for viability. The cells were washed three times with PBS (to remove residual IL-2), re-suspended in medium (RPMI1640, 10% FCS, 1% Glutamine) without IL-2 and incubated for two hours in cell incubator (IL-2 starvation). After starvation, 200'000 CTLL2 cells per ml were re-suspended in fresh medium without IL2 and 50 µl of cell suspension transferred in a 96-well cell culture treated flat bottom plate. 50 µl of diluted murine surrogate PD1-IL2v, murine surrogate PD-L1-IL2v, murine surrogate CEA-IL2v, diluted Proleukin (1.5 µg/ml final concentration) or medium alone (all using IL-2-free medium) were added to wells to a final volume of 100 µl/well. Samples were incubated for 3 days in cells incubator and proliferation was assessed using CellTiter-Glo according to manufacturer's instructions. Briefly, 100 µl reagents were added to each well and incubated for 10 min. Remaining aggregates were re-suspended by pipetting and 150 µl of mixture were transferred to a white flat bottom plate. The luminescence was measured with Tecan Spark 10M multimode reader.

Figure 9A:
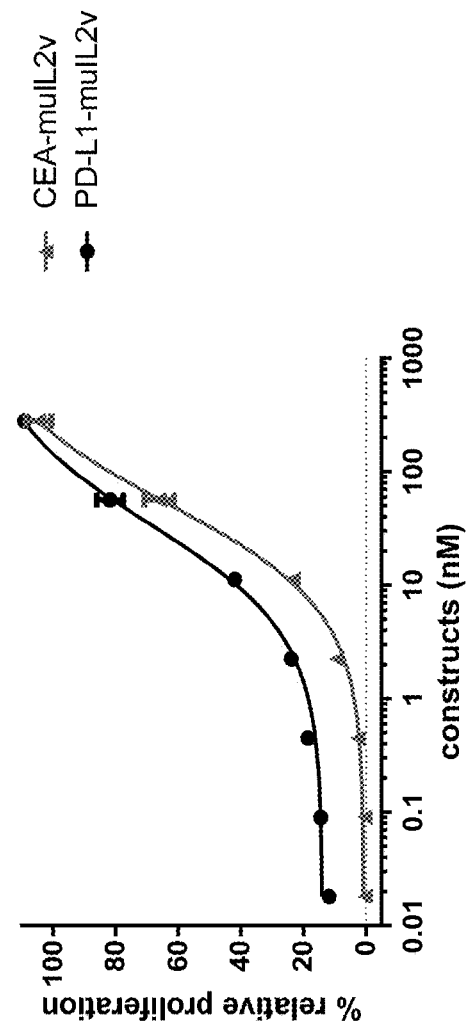
FIGS. 9A and 9B. Proliferation of the murine PD-L1 positive T cell line CTLL2 induced by PD1-muIL2v in comparison to CEA-muIL2v (FIG. 9A), or by PD1-muIL2v in comparison to PD-L1-muIL2v (FIG. 9B), determined after 3 days.
Figure 9B:
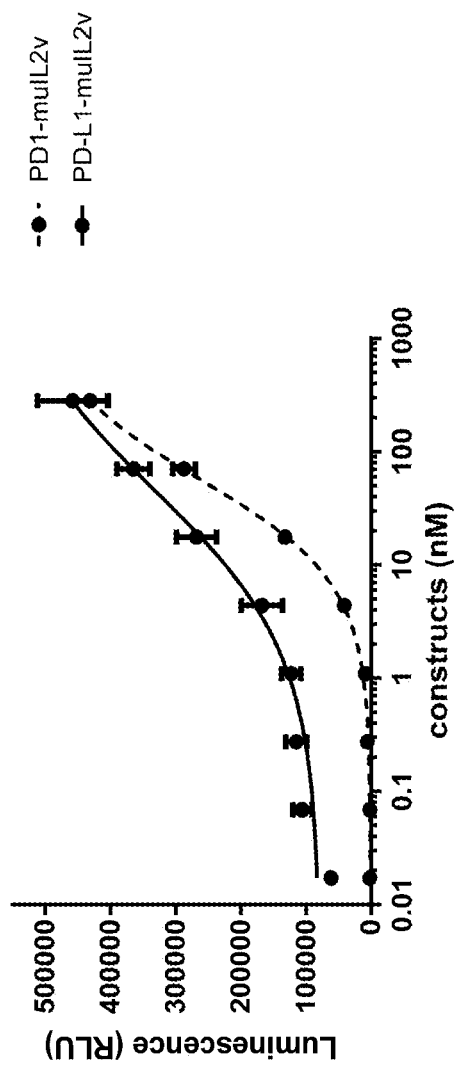

FIG. 9A shows that PD-L1-IL2v induces proliferation of CTLL2 cells. The activity seems to be higher compared to CEA-IL2v probably due to the expression of PD-L1 on CTLL2 cells. FIG. 9B again shows that PD1-IL2v induces proliferation of CTLL2 cells. The activity seems to be lower compared to PD-L1-IL2v probably because these cells express only PD-L1 but not PD1.

Example 3

In Vivo Efficacy of PD1-IL2v and PD-L1-IL2v in a Syngeneic Mouse Tumor Model

The PD1-IL2v and PD-L1-IL2v immunoconjugates (murine surrogates) were tested alone and in comparison to corresponding PD1 and PD-L1 antibodies for their antitumoral efficacy in the Panc02-Fluc syngeneic model.

Panc02-H7 cells (mouse pancreatic carcinoma) were originally obtained from the MD Anderson cancer center (Texas, USA) and after expansion deposited in the Roche-Glycart internal cell bank. Panc02-H7-Fluc cell line was produced in house by calcium transfection and sub-cloning techniques. Panc02-H7-Fluc was cultured in RPMI medium containing 10% FCS (Sigma), 500 µg/ml hygromicin and 1% of Glutamax. The cells were cultured at 37° C. in a water-saturated atmosphere at 5% $CO_2$. Passage 23 was used for transplantation. Cell viability was 90.4%. $1 \times 10^5$ cells per animal were injected into the pancreas of Black 6 mice using a 0.3 ml tuberculin syringe (BD Biosciences, Germany). For this a small incision was made at the left abdominal site of anesthetized mice. The peritoneal wall was opened and the pancreas carefully isolated with forceps. Ten microliters ($1 \times 10^5$ Panc02-H7-Fluc cells in RPMI medium) cell suspension was injected in the tail of the pancreas. Peritoneal wall and skin wounds were closed using 5/0 resolvable sutures.

Female Black 6 mice aged 10-12 weeks at the start of the experiment (Charles Rivers, Lyon, France) were maintained under specific-pathogen-free condition with daily cycles of 12 h light/12 h darkness according to committed guidelines (GV-Solas; Felasa; TierschG). The experimental study protocol was reviewed and approved by local government (ZH193/2014). After arrival, animals were maintained for one week to get accustomed to the new environment and for observation. Continuous health monitoring was carried out on a regular basis.

Mice were injected intra-pancreatically on study day 0 with $1 \times 10^5$ Panc02-Fluc cells, randomized and weighed. One week after the tumor cell injection mice were injected i.v. with PD1-IL2v, PD-L1-IL2v or PD1 and PD-L1 antibodies, once weekly for four weeks.

All mice were injected i.v. with 200 µl of the appropriate solution. The mice in the vehicle group were injected with histidine buffer and the treatment groups with the murine surrogate PD1-IL2v and PD-L1-IL2v conjugates or the corresponding PD1 and PD-L1 antibodies, diluted with histidine buffer as appropriate. The amount of antibodies injected per mouse in mg/kg was the following: 1.5 mg/kg PD1-IL2v and PD-L1-IL2v, 10 mg/kg PD1 and PD-L1 antibodies.

Figure 10:
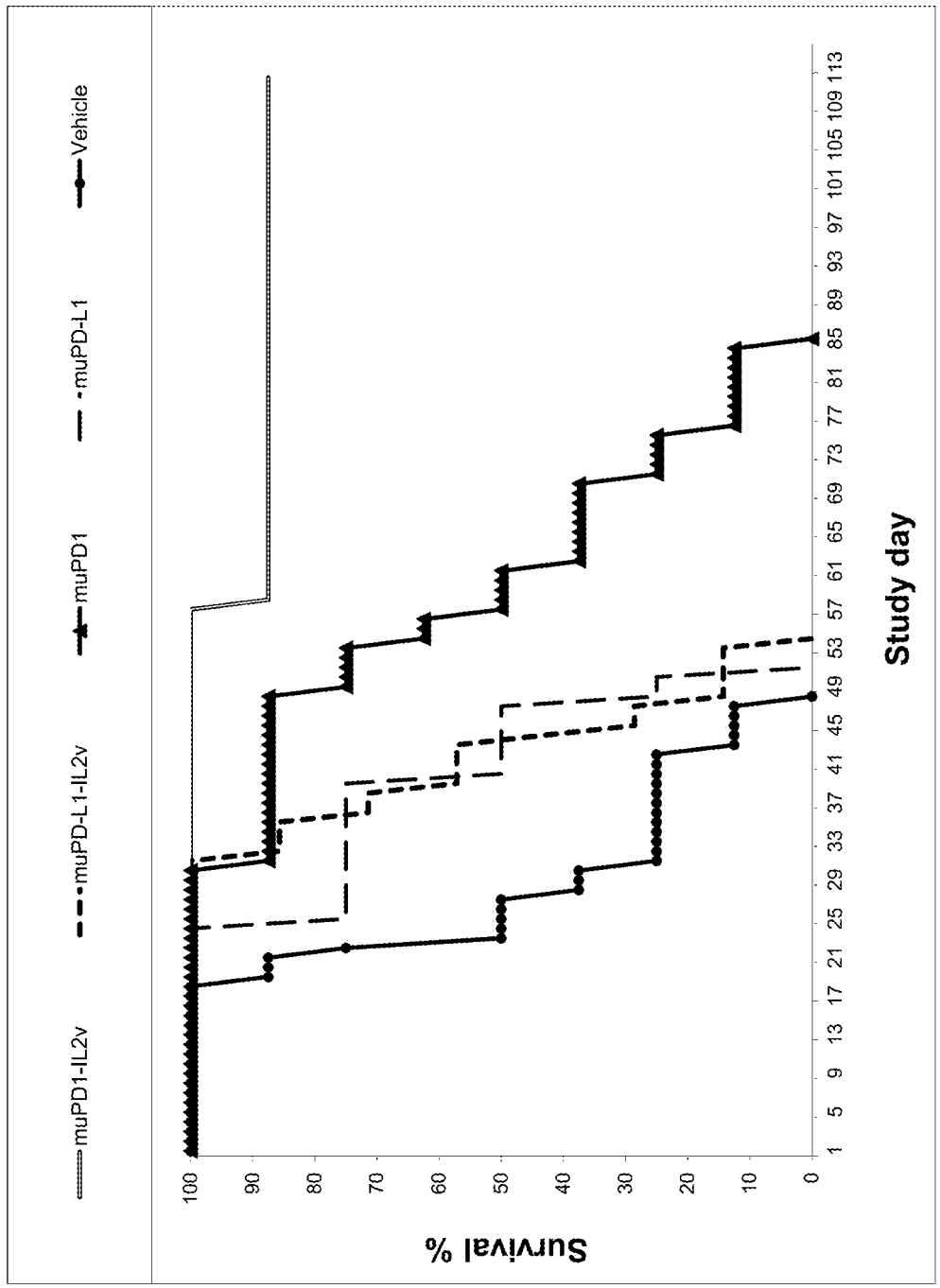
FIG. 10. Results of an efficacy experiment with PD1-IL2v, PD-L1-IL2v or PD1 and PD-L1 antibodies as single agents. The Panc02-H7-Fluc transfectant pancreatic carcinoma cell line was injected into the pancreas of Black 6 mice to study survival in a pancreatic orthotopic syngeneic model.

FIG. 10 and Table 1 show that PD1-IL2v mediated significantly superior efficacy in terms of enhanced median and overall survival compared to all other single agents tested, notably including PD-L1-IL2v.

TABLE 1

Median and overall survival of Black 6 mice treated with PD1-IL2v, PD-L1-IL2v, PD1 or PD-L1 antibody, in the Panc02-Fluc syngeneic tumor model.

| Groups | Median Survival in days | p-value vs control | Overals survival |
|---|---|---|---|
| muPD1-IL2v | Not reached | <0.0001*** | 7/8 |
| muPD-L1-IL2v | 43 | 0.0045* | 0/8 |
| muPD1 | 58 | 0.0002** | 0/8 |
| muPD-L1 | 28 | 0.0985 | 0/8 |
| Vehicle | 24 | 1 | 0/8 |

For Bioluminescence imaging by IVIS® SPECTRUM, the mice were injected intra-peritoneally with 150 mg/kg of D-Luciferin 10 minutes before bioluminescence imaging acquisition (BLI) and later anesthetized with 4% isoflurane. Subsequently the mice were transferred into an isolation chamber, which is positioned into the IVIS® spectrum. In vivo BLI acquisitions were performed by acquiring the luminescence signal for 10-50 seconds. Data was stored as Radiance (photons)/sec/cm2/sr. In vivo BLI data analysis was performed with the Living Image® 4.4 software and represented by a tumor inhibition curve.

Figure 11:
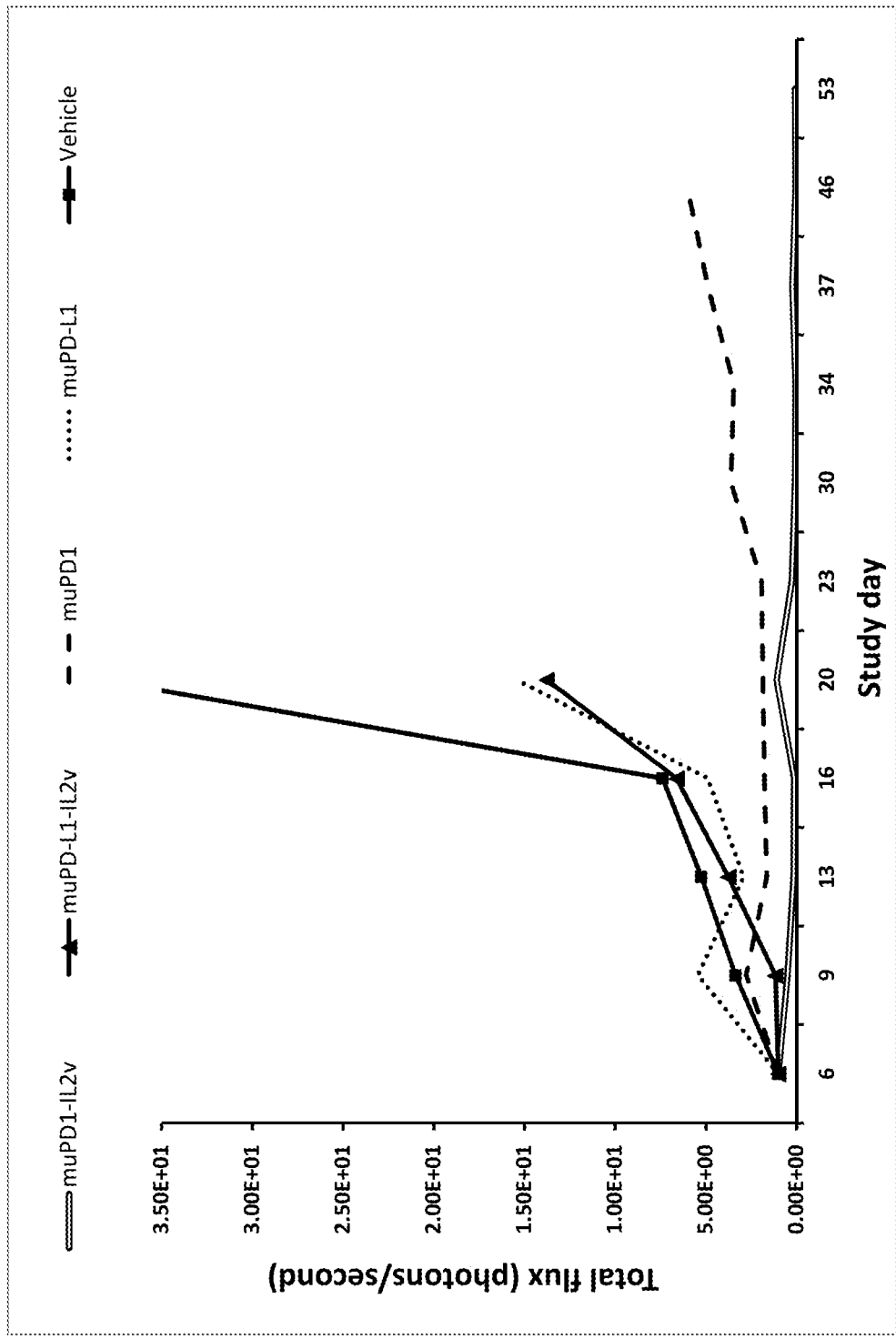
FIG. 11. Results of an efficacy experiment with PD1-IL2v, PD-L1-IL2v or PD1 and PD-L1 antibodies as single agents. The Panc02-H7-Fluc transfectant pancreatic carcinoma cell line was injected into the pancreas in Black 6 mice to study survival in a pancreatic orthotopic syngeneic model by means of bioluminescence.

FIG. 11 shows PD1-IL2v superior efficacy in terms of decreasing the bioluminescence signal (photons/second) compared to all other groups, notably including PD-L1-IL2v. As early as after the first therapy administration at day 7 a reduction in the Panc02-Fluc bioluminescence signal was detected by IVIS® Spectrum in several treated groups, but only PD1-IL2v show a complete disappearance of the BLI signal in most mice that lasted the entire duration of the experiment, indicative of a complete response in 7 out of 8 mice.

Example 4

Effect of IL-2v Delivery to Exhausted Virus-Specific T Cells Through Either PD-1 or PD-L1 Blockade PD-1 expression has been described for the first time on exhausted virus-specific T cells as a consequence of chronic-exposure to viral antigens and it has been associated with T-cell inability to mount an effective anti-viral response. Virus-specific CD4 T cells able to simultaneously secrete IL-2 and IFN-γ confer protection from viral re-activation in chronic infections. Indeed, the polyfunctional signature of CD4 T cells has been associated with viral-control in healthy individuals infected by Cytomegalovirus (CMV), Epstein-Barr virus (EBV) and Herpes Simplex virus (HSV) as well as in those individuals infected with Human Immunodeficiency virus (HIV) who remain symptoms-free for several years.

In the context of chronic viral infections, we therefore developed an in-vitro assay to evaluate the effect of PD-1 and PD-L1 targeting to deliver a mutated version of IL-2 (IL-2v) to dysfunctional antigen-specific T cells. To avoid restrictions on the amount of suitable donors for our assay, we opted for a CMV immunogenic viral-protein (pp65) as re-call antigen for T cells given that roughly 80% of the population is CMV-seropositive. Hence, we stimulated healthy human donor peripheral blood mononuclear cells (PBMCs) with CMV-pp65 for a couple of hours before adding our constructs at the concentration of 10 µg/ml. 43 hours later we blocked the protein transport from the Golgi by adding Golgi Plug (Brefeldin A) and Golgi Stop (Monensin) and incubated the cells at 37° C. for additional 5 hours. The cells were then washed, stained on the surface with anti-human CD3, CD4, CD8, CD62L and CD45RO antibodies before being fixed/permeabilized with Fix/Perm Buffer (BD Bioscience). At last we performed intracellular staining for IL-2, IFN-γ and Ki67 (both from eBioscience).

Figure 12A:
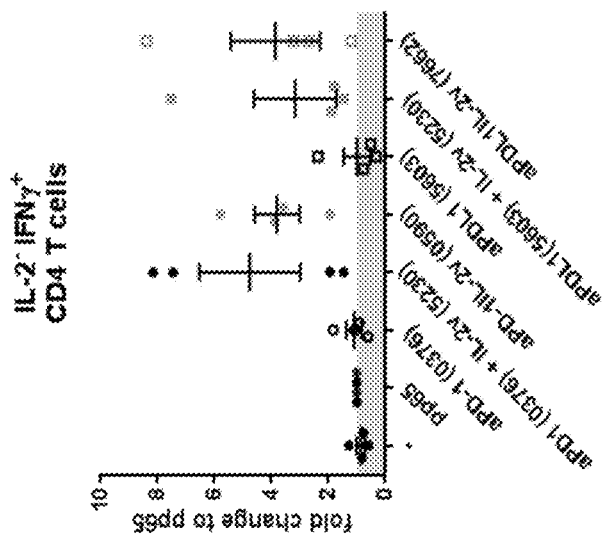
FIGS. 12A-12C. Ability of CD4 T cells to secrete IL-2 (FIG. 12A), IL-2 and IFN-γ (FIG. 12B) or IFN-γ (FIG. 12C) upon 48 hours recall with CMV immunogenic protein pp65 in presence of either anti-PD-1 or anti-PD-L1 alone, in combination with IL-2v, or as fusion proteins.
Figure 12B:
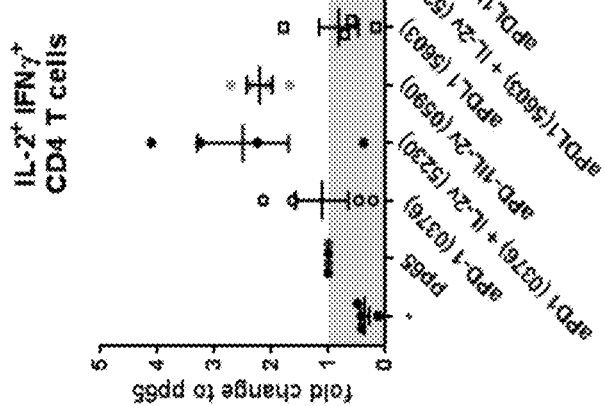
Figure 12C:
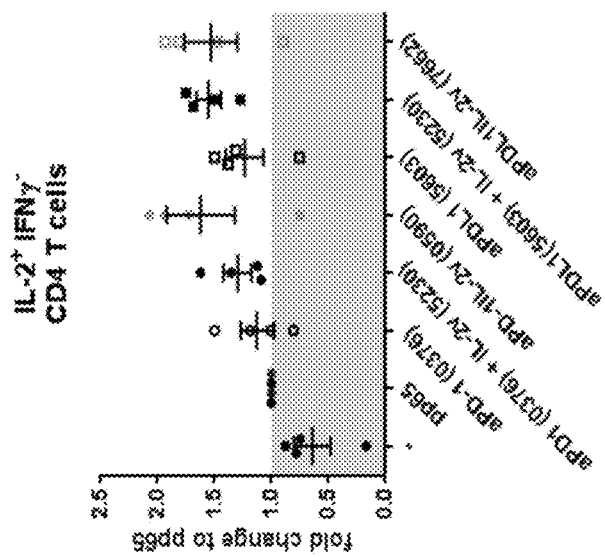
Figure 13A:
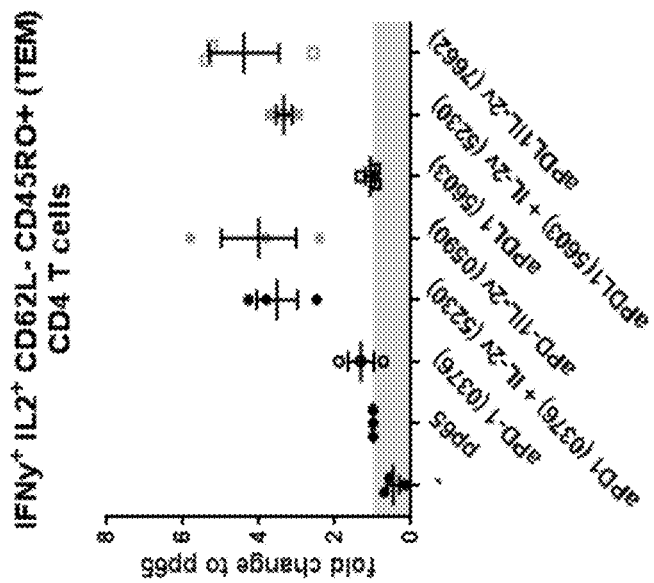
FIGS. 13A-13D. Differentiation state of virus-specific CD4 T cells secreting only IL-2 (FIG. 13A), both IL-2 and IFN-γ (FIG. 13B), or only IFN-γ (FIGS. 13C and 13D) upon 48 hours recall with CMV immunogenic protein pp65 in presence of either anti-PD-1 or anti-PD-L1 alone, in combination with IL-2v, or as fusion proteins.
Figure 13B:
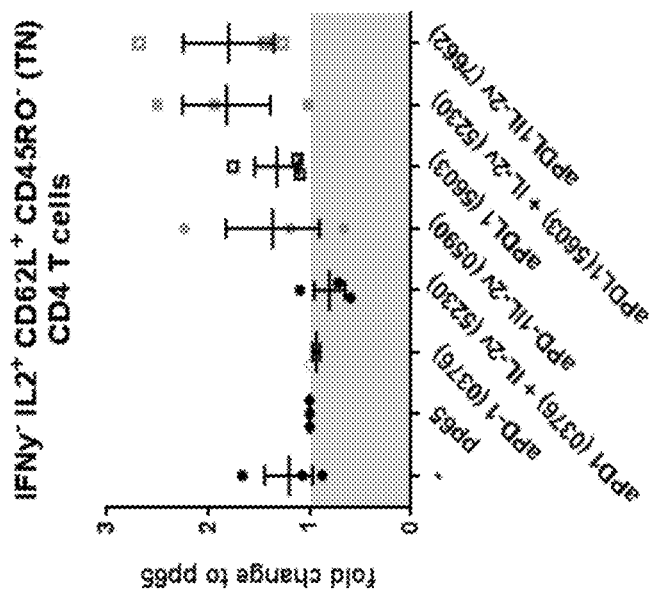
Figure 13C:
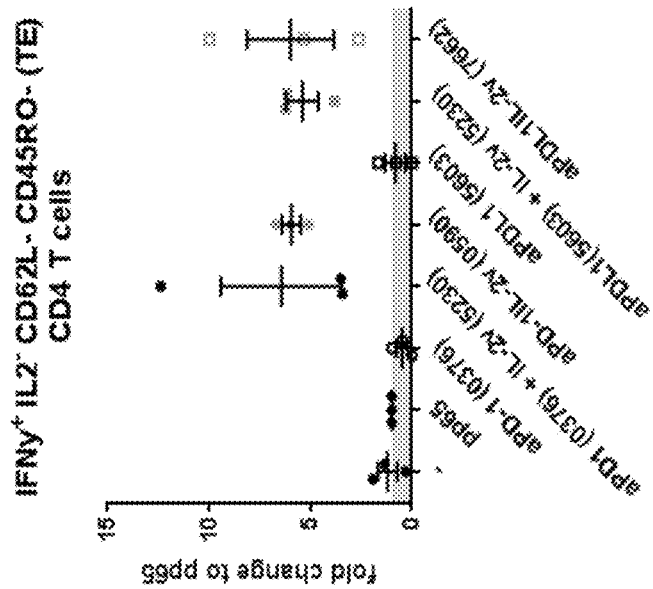
Figure 13D:
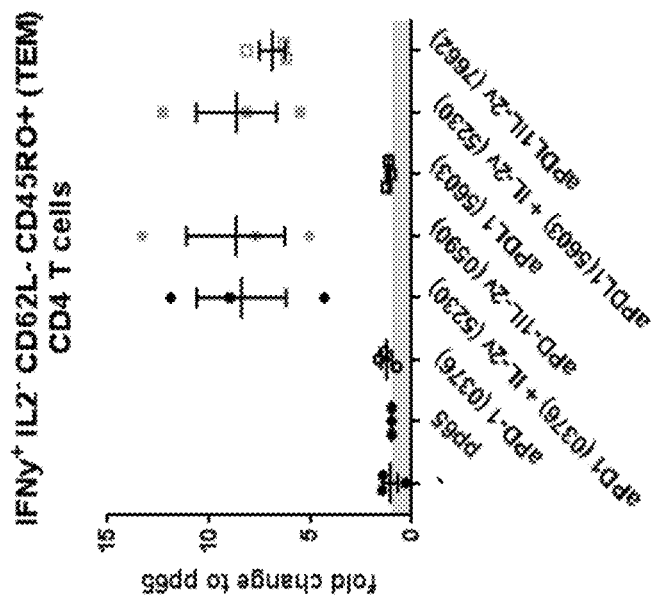

We observed that both PD1-IL2v and PD-L1-IL2v, as well as the combination of the corresponding IgG antibodies with IL-2v, increased, at comparable levels, the frequencies of polyfunctional (FIG. 12B) and IL-2 and IFN-γ monofunctional (FIGS. 12A and 12C, respectively) CD4 T cells, providing an enhanced effect as compared to anti-PD-1 and anti-PD-L1 blockade, respectively. The expanded populations in the polyfunctional (FIG. 13B) and IFN-γ monofunctional CD4 T cells (FIGS. 13C and 13D) show an effector-memory (CD45RO+CD62L−) and terminally differentiated effector profile (CD45RO− CD62L−). Conversely, the IL-2-monofunctional CD4 T cells induced by PD-L1 antagonism, and further expanded by the co-delivery of IL-2v, display a naive signature (CD62L+ CD45RO−) (FIG. 13A).

We can conclude that delivering IL-2v to the exhausted CMV-specific CD4 T cells through the PD1-IL-2v fusion protein resulted in the expansion of a long-lived protective virus-specific population characterized by the ability to co-secrete IL-2 and IFN-γ.

Example 5

Example 5A. Preferential Binding of PD1-IL2V to Activated Conventional T Cells Over Activated Regulatory T Cells The binding properties of PD1-IL2v to activated conventional and regulatory T cells were assessed in a competitive binding assay. CD4+CD25+CD127$^{dim}$ Regulatory T cells (T$_{reg}$) were isolated with the two-step Regulatory T cell Isolation Kit (Miltenyi, #130-094-775). In parallel the CD4+ CD25$^-$ conventional T cells (T$_{conv}$) were isolated by collecting the negative fraction of a CD25 positive selection (Miltenyi, #130-092-983) followed by a CD4$^+$ enrichment (Miltenyi, #130-045-101). The T$_{conv}$ were labelled with CFSE (eBioscience, #65-0850-84) and the Treg were labelled with Cell Trace Violet (ThermoFisher scientific, C34557) to track the proliferation of both populations. T$_{conv}$ and T$_{reg}$ were together seeded into a culture plate that were coated overnight at 4° C. with 1 µg/ml CD3 (clone OKT3, #317315, BioLegend). CD28 was added in solution at a concentration of 1 µg/ml CD28 (clone CD28.2, #302923, BioLegend). After 5 days of stimulation a binding assay was conducted with PD1 (0376) and PD1-IL2v (0590), which were both labelled in-house with AF647.

Figure 14A:
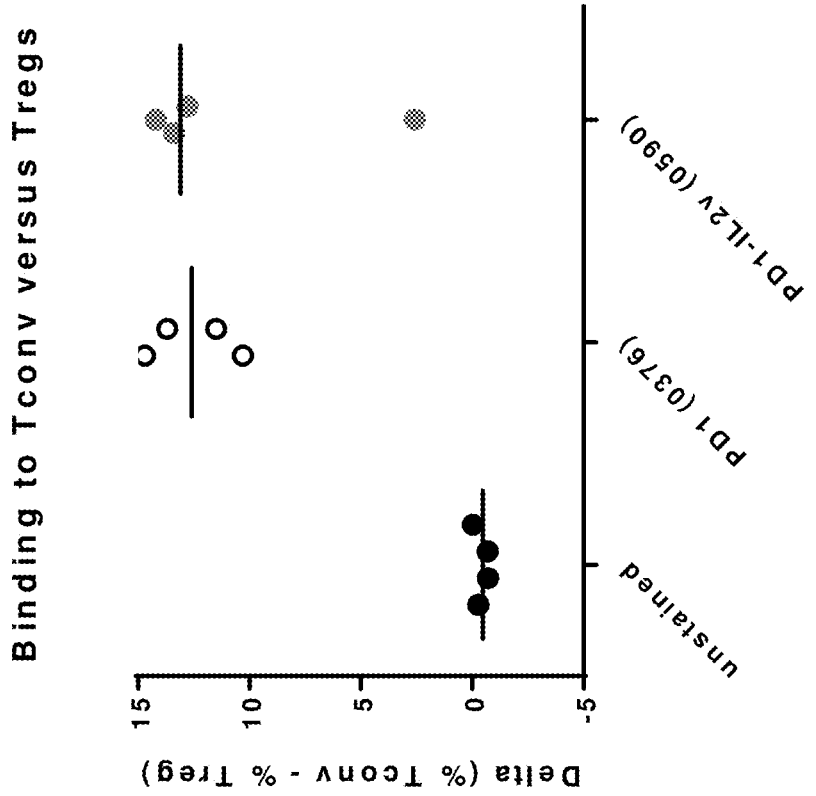
FIGS. 14A and 14B. Competitive binding assay of PD1 and PD1-IL2v to activated conventional and regulatory T cells. Delta of the frequency bound on $T_{conv}$ versus $T_{reg}$ (FIG. 14A) and binding to $T_{conv}$ and $T_{reg}$ (FIG. 14B).
Figure 14B:
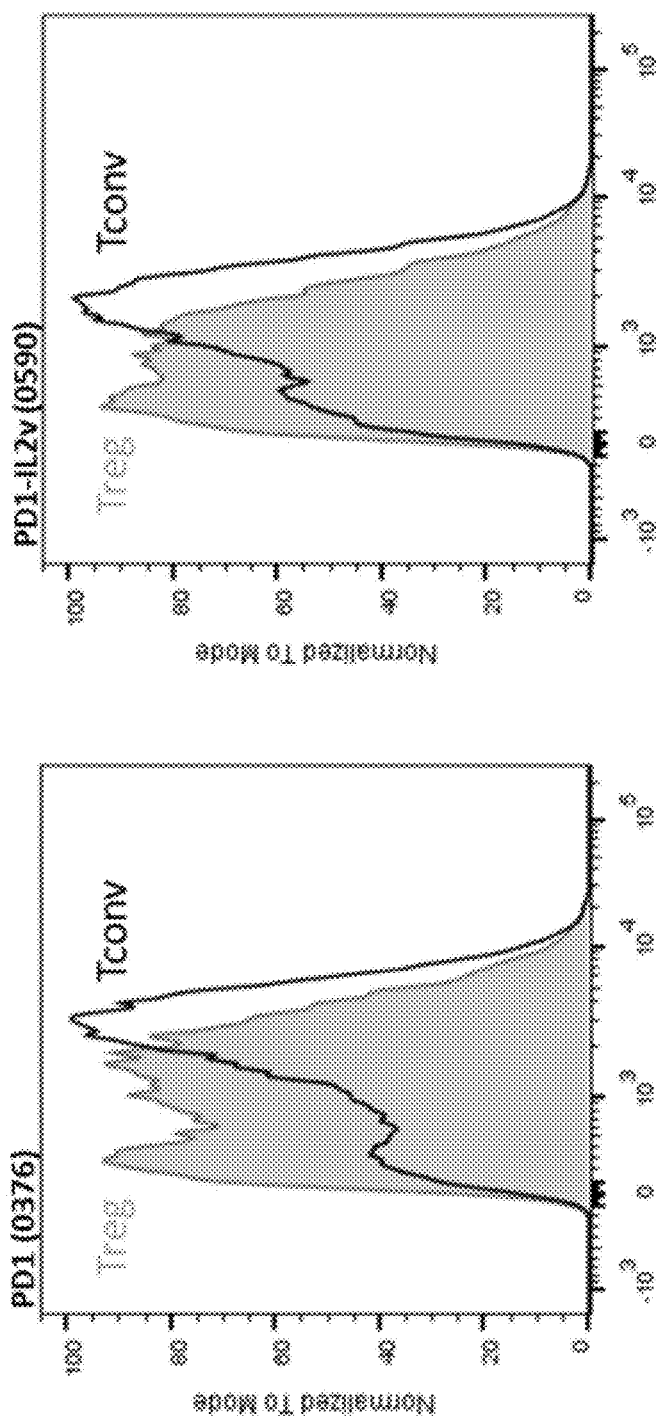

The PD1-IL2v bispecific antibody shows a comparable binding profile as PD1 (FIGS. 14A and 14B). FIG. 14A shows the Delta of the frequency of a given antibody bound on T$_{conv}$ versus T$_{reg}$ within the same sample. Each symbol represents a separate donor, horizontal lines indicate medians with N=4. Both molecules show higher binding capacity to T$_{conv}$ over T$_{reg}$ due to higher expression levels of PD-1 on T$_{conv}$ than on T$_{reg}$ (FIG. 14B; data from one representative donor showing the binding to T$_{conv}$ (black line) and T$_{reg}$ (grey)). Hence the PD1-IL2v bispecific antibody maintains the binding properties of PD1 despite the IL2v being coupled to the antibody.

Example 5B. Rescue of T$_{Conv}$ Effector Function Upon PD1-IL2V Treatment in T$_{Reg}$ Suppression Assay In a next step it was tested, if the PD1-IL2v can reverse the T$_{reg}$ suppression of T$_{conv}$. Therefore a suppressive-function assay was established, where T$_{conv}$ and T$_{reg}$ are cultured together for 5 days, with or without blocking antibodies, in presence of CD4$^-$ CD25$^-$ from an unrelated donor for allospecific stimulation. For this purpose T$_{conv}$ and T$_{reg}$ were isolated and labelled as described above. The accumulation of cytokines in the Golgi complex was enhanced by applying Protein Transport Inhibitors (GolgiPlug #555029, BD and GolgiStop #554724, BD) for 5 hours prior to the FACS staining.

Figure 15B:
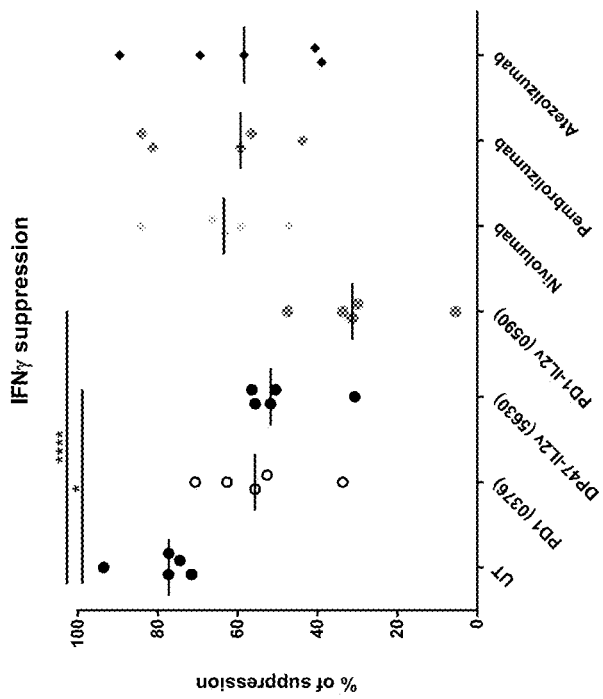
FIGS. 15A and 15B. PD1-IL2v reversion of $T_{reg}$ suppression of $T_{conv}$. Percentage of suppression by $T_{reg}$ of granzyme B (FIG. 15A) and interferon-γ (FIG. 15B) secreted by $T_{conv}$ after 5 days of coculture.
Figure 15A:
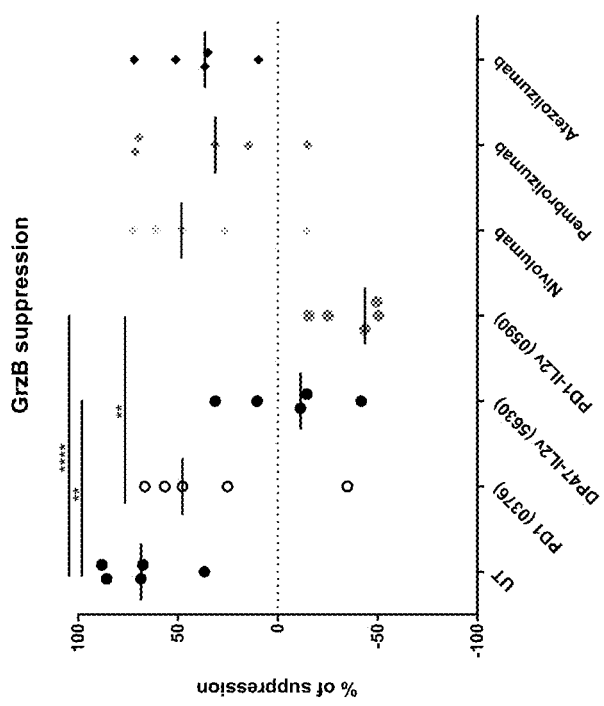

The ability of the proliferated T$_{conv}$ to secrete granzyme B (GrzB; [[F]]FIG. 15A) and interferon gamma (IFNγ; FIG. 15B) in presence and absence of T$_{reg}$ was measured. The T$_{reg}$ suppression was calculated with the following formula:

% cytokine suppression=100−
(% cytokine$_{Tconv+Treg\pm blocking\ antibody}$)/(% cytokine$_{Tconv\ untreated}$)*100), where % cytokine$_{Tconv+Treg\pm blocking\ antibody}$ is the level of cytokine secreted by T$_{conv}$ in the presence of T$_{reg}$±blocking antibody, % cytokine$_{Tconv\ untreated}$ is the level of cytokine secreted by T$_{conv}$ in the absence of Treg. In FIGS. 15A and 15B, each symbol represents a separate donor, horizontal lines indicate medians with N=5, dotted lines at 0% represents no suppression by T$_{reg}$. P was calculated using one-way ANOVA (*p<0.05, p<0.01, *p<0.001, ****p<0.0001).

FIG. 15A shows that the treatment with the PD1 antibody (0376) results in a median of 47.7% of T$_{conv}$ function suppression, compared to a median of 68.6% suppression in the untreated group (no statistical significance). Likewise the blocking of PD-1/PD-L1 interaction with Atezolizumab, Nivolumab and Pembrolizumab showed the same tendency as for the PD1 antibody. Interestingly DP47-IL2v (median=−11.3%, p=0.0011) and PD1-IL2v (median=−43.6%, p<0.0001) rescued T$_{conv}$ GrzB effector function from T$_{reg}$ suppression. Furthermore PD1-IL2v was even significantly (p=0.0026) more potent than PD1 antibody alone.

In parallel the same analysis were performed for INFγ suppression of T$_{conv}$ by T$_{reg}$ (FIG. 15B). DP47-IL2v (median=51.77%, p=0.0251) and PD1-IL2v (median=31.23%, p=<0.0001) rescued T$_{conv}$ IFNy effector function from T$_{reg}$ suppression.

Example 6

In Vivo Efficacy of PD1-IL2v Immuno-Conjugates in a Syngeneic Model of Mouse Tumor Cell Lines Compared to PD1 and FAP-IL2v Antibodies as Single Agents and in Combination The murine surrogate PD1-IL2v immuno-conjugate (muPD1-IL2v) was tested in comparison to a combination of murine surrogate PD1 and murine surrogate FAP-IL2v (muFAP-IL2v) for its anti-tumoral efficacy in a syngeneic model. The syngeneic model used was the Panc02-Fluc pancreatic Syngeneic Model.

The murine surrogate PD1-IL2v immuno-conjugate was tested in the mouse pancreatic Panc02-Fluc transfectant cell line intra-pancreatically injected into Black 6 mice. Panc02-H7 cells (mouse pancreatic carcinoma) were originally obtained from the MD Anderson cancer center (Texas, USA) and after expansion deposited in the Roche-Glycart internal cell bank. Panc02-H7-Fluc cell line was produced in house by calcium transfection and sub-cloning techniques. Panc02-H7-Fluc was cultured in RPMI medium containing 10% FCS (Sigma), 500 µg/ml hygromicin and 1% of Glutamax. The cells were cultured at 37° C. in a water-saturated atmosphere at 5% CO$_2$. Passage 23 was used for transplantation. Cell viability was 87.5%. 1×10$^5$ cells per animal were injected into the pancreas of the mice using a 0.3 ml tuberculin syringe (BD Biosciences, Germany). For this a small incision was made at the left abdominal site of anesthetized Black 6 mouse. The peritoneal wall was opened and the pancreas carefully isolated with forceps. Ten microliters (1×10$^5$ Panc02-H7-Fluc cells in RPMI medium) cell suspension was injected in the tail of the pancreas. Peritoneal wall and skin wounds were closed using 5/0 resolvable sutures.

Female Black 6 mice aged 10-12 weeks at the start of the experiment (Charles Rivers, Lyon, France) were maintained under specific-pathogen-free condition with daily cycles of 12 h light/12 h darkness according to committed guidelines (GV-Solas; Felasa; TierschG). The experimental study protocol was reviewed and approved by local government (ZH193/2014). After arrival, animals were maintained for one week to accustomize to the new environment and for observation. Health monitoring was carried out on a regular basis.

Mice were injected intra-pancreatically on study day 0 with 1×10$^5$ Panc02-Fluc cells, randomized and weighed. One week after the tumor cell injection mice were injected intravenously with two different doses of PD1-IL2v and compared to the combination of PD1 and FAP-IL2v antibodies, once per week for four weeks.

All mice were injected intravenously with 200 µl of the appropriate solution. The mice in the vehicle group were injected with Histidine Buffer and the treatment groups with the PD1-IL2v (0.5 mg/kg or 1 mg/kg), PD1 (10 mg/kg) and FAP-IL2v (2.5 mg/kg) antibodies or the combination of PD1 and FAP-IL2v (10 mg/kg PD1 and 2.5 mg/kg FAP-IL2v) antibodies. To obtain the appropriate amount of immunoconjugates per 200 μl, the stock solutions were diluted with Histidine Buffer when necessary according to Table 2.

TABLE 2

Compounds, doses, formulation buffers and stock solution concentration.

| Compound | Dose | Formulation buffer | Concentration of stock solution (mg/mL) |
|---|---|---|---|
| muPD1-IL2v | 10 μg and 30 μg | 20 mM Histidine, 140 mM NaCl, 0.01% Tween20; pH 6.0 | 3.63 |
| muFAP-IL2v | 50 μg | 20 mM Histidine, 140 mM NaCl, 0.01% Tween20; pH 6.0 | 4.91 |
| muPD1 | 200 μg | 20 mM Histidine, 140 mM NaCl, 0.01% Tween20; pH 6.0 | 5.84 |

For Bioluminescence imaging by IVIS® SPECTRUM, the mice are injected intra-peritoneal with 150 mg/kg of D-Luciferin 10 minutes before bioluminescence imaging acquisition (BLI) and later anesthetized with 4% isoflurane. Subsequently the mice are transferred into an isolation chamber, which is positioned into the IVIS® spectrum. In vivo BLI acquisitions are performed by acquiring the luminescence signal for 10-50 seconds. Data is stored as Radiance (photons)/sec/cm$^2$/sr. In vivo BLI data's analysis is performed with the Living Image® 4.4 software and represented by a tumor inhibition curve.

To evaluate the immune-pharmacodynamic by histology, 3 mice per group were sacrificed 4 days after the first therapy by neck dislocation. The pancreas tumors were harvested and fix immediately in formalin 10%. The tissue was left in formalin solution overnight and later processed for FFPET (Leica 1020, Germany). 4 μm paraffin sections were subsequently cut in a microtome (Leica RM2235, Germany). Mouse CD3, PD1 and ICOS immunohistochemistry was performed in the Leica autostainer (Leica ST5010, Germany) following the manufacture's protocols. Images were scanned with Olympus scanner.

Figure 16:
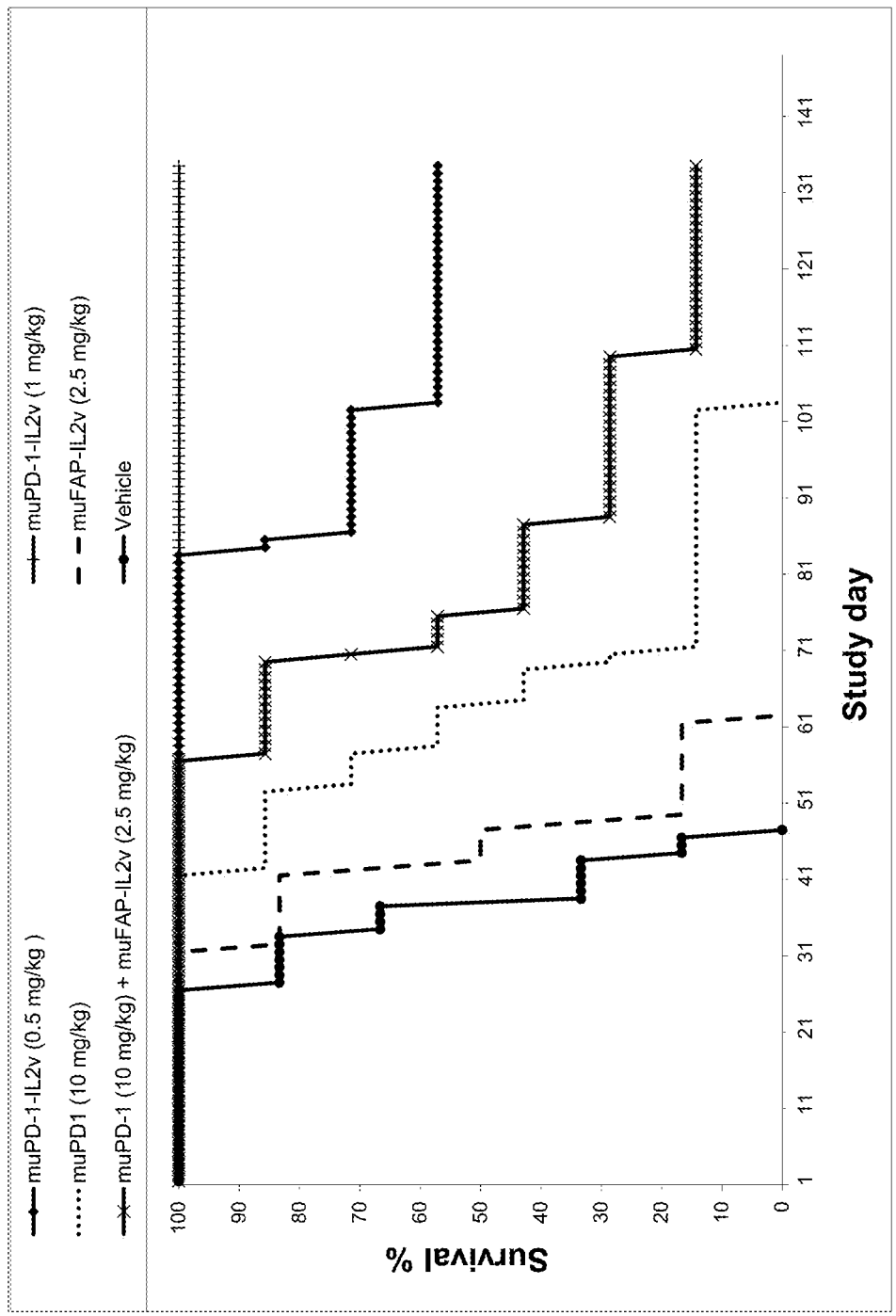
FIG. 16. Results of an efficacy experiment comparing muPD1-IL2v to muFAP-IL2v and muPD-1 antibodies as single agents and in combination.

FIG. 16 shows the results of an efficacy experiment comparing murine surrogate PD1-IL2v to murine surrogate FAP-IL2v and murine surrogate PD-1 antibodies as single agents and in combination. The Panc02-H7-Fluc transfectant pancreatic carcinoma cell line was injected into the pancreas in Black 6 mice to study survival in a pancreatic orthotopic syngeneic model. The amount of antibodies injected per mouse in mg/kg is the following: 0.5 and 1 mg/kg murine surrogate PD1-IL2v, 10 mg/kg murine surrogate PD1 and 2.5 mg/kg murine surrogate FAP-IL2v antibodies. The antibodies were injected intravenously once per week for 4 weeks. Significant superior median and overall survival was observed in the 0.5 and 1 mg/kg murine surrogate PD1-IL2v compared to all other single agents and the combination of murine surrogate PD-1 and murine surrogate FAP-IL2v. FIG. 16 and Table 3 show that both doses of PD1-IL2v mediated superior efficacy in terms of enhanced median and overall survival compared to all other single agents, as well as the combination of PD1 and FAP-IL2v.

TABLE 3

Median and overall survival of Black 6 mice treated with PD1-IL2v, PD1, FAP-IL2v and a combination of PD-1 and FAP-IL2v antibody, in the Panc02-Fluc syngeneic tumor model.

| Groups | Median Survival in days | p-value vs control | Overall survival |
|---|---|---|---|
| muPD1-IL2v (0.5 mg/kg) | Not reached | <0.0001*** | 4/7 |
| muPD1-IL2v (1 mg/kg) | Not reached | <0.0001*** | 7/7 |
| muPD1 (10 mg/kg) | 63 | 0.0014* | 0/7 |
| muFAP-IL2v | 45 | 0.0941 | 0/6 |
| muPD-1 and muFAP-IL2v | 75 | 0.0002*** | 1/7 |
| Vehicle | 37 | 1 | 0/6 |

Figure 17:
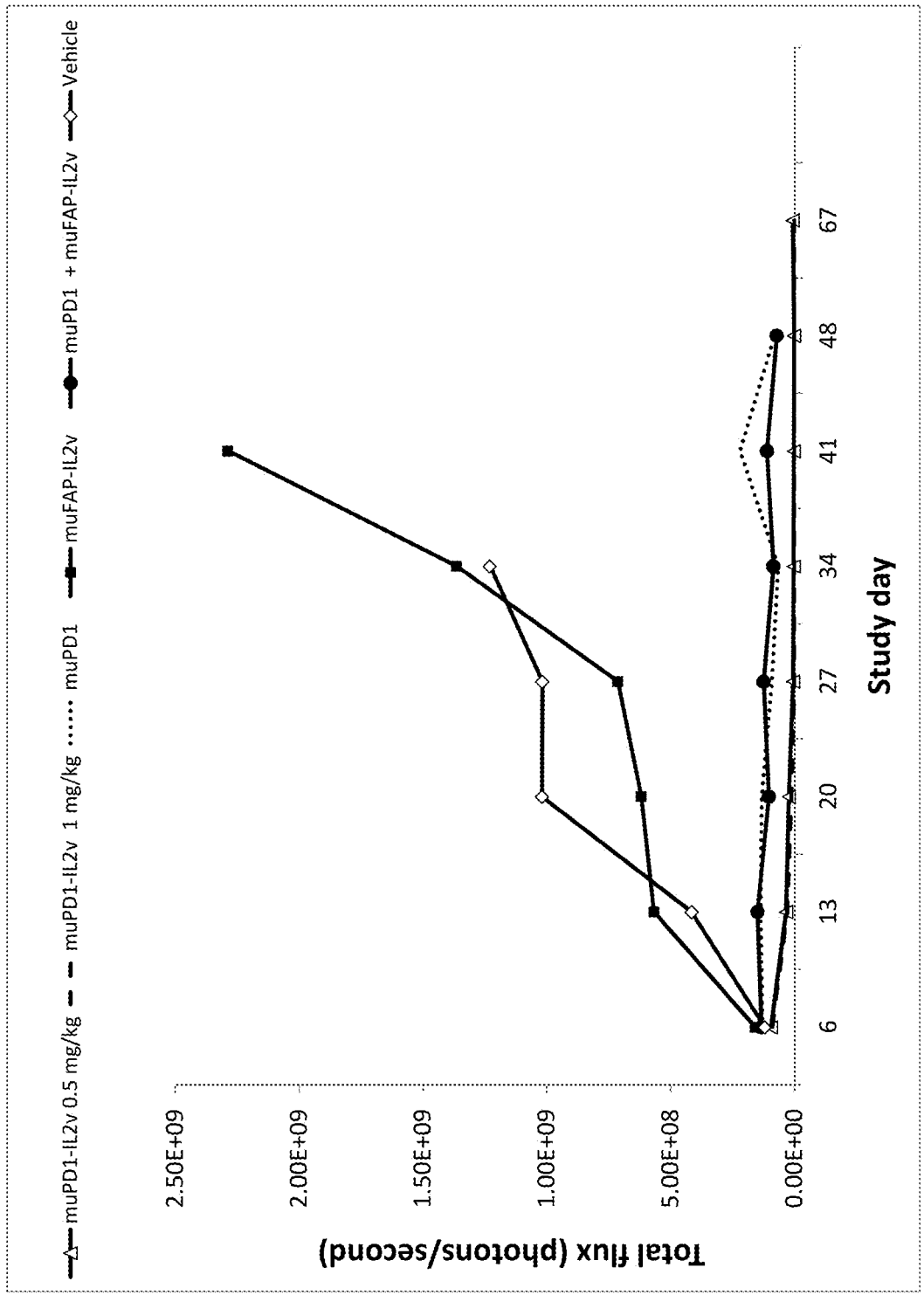
FIG. 17. Results of an efficacy experiment comparing muPD1-IL2v to FAP-IL2v, muPD1 and their combination.

FIG. 17 shows the results of an efficacy experiment comparing murine surrogate PD1-IL2v to FAP-IL2v, murine surrogate PD1 and their combination. The Panc02-H7-Fluc transfectant pancreatic carcinoma cell line was injected into the pancreas in Black 6 mice to study survival in a pancreatic orthotopic syngeneic model by means of bioluminescence. As early as after the first therapy administration at day 7 a reduction in the Panc02-Fluc bioluminescence signal was detected by IVIS® Spectrum in several treated groups, but only PD1-IL2v show a complete disappearance of the BLI signal in most mice that lasted the whole duration of the experiment, indicative of a complete response in 4 out of 7 mice for the 0.5 mg/kg dose and 7 out of 7 mice for the 1 mg/kg dose. FIG. 17 shows that both doses of PD1-IL2v mediated superior efficacy in terms of decreasing the bioluminescence signal (photons/second) compared to all other single agent and the combination group.

Figure 18B:
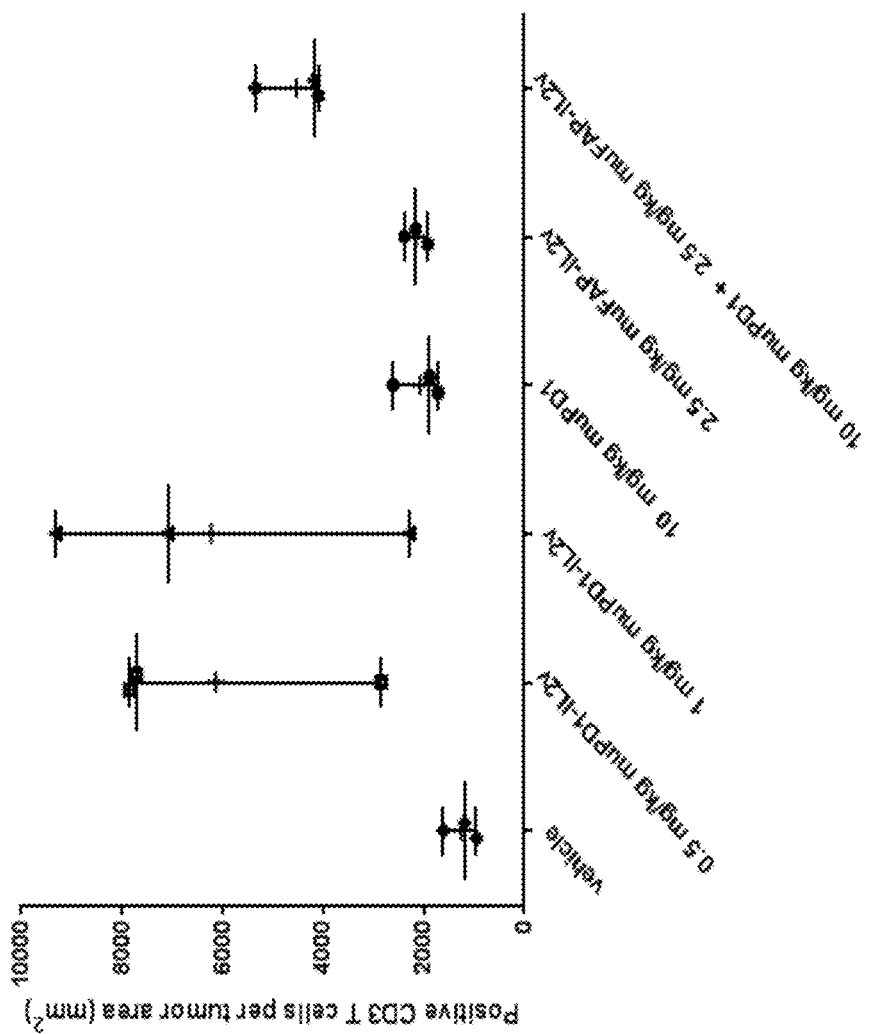

FIGS. 18A and 18B show the results of immunohistochemical images of pancreas tumors stained for anti-mouse CD3 (FIG. 18A) and the T cell quantification analysis (FIG. 18B). Immunohistochemistry staining of CD3 T cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 μm paraffin sections were subsequently cut in a microtome (Leica RM2235, Germany). Mouse CD3 immunohistochemistry was performed with anti-mouse CD3 (Diagnostic Biosystem, Germany) in the Leica autostainer (Leica ST5010, Germany) following the manufacture's protocols. Images were scanned with Olympus scanner. Quantification of muCD3 positive T cells was performed with Definiens software (Definiens, Germany). Statistics were analyzed by one way ANOVA with multiple comparison tests. As early as after the first therapy administration, at day 4, a significant increase in the number of CD3 positive T cells was detected in the PD1-IL2v treated groups compared to vehicle group. A tendency to increase in CD3 positive cells was also seen in the combination of murine surrogate PD1 and murine surrogate FAP-IL2v with respect to vehicle, but was not significant. FIGS. 18A and 18B show that PD1-IL2v elicited an increase in CD3 infiltration in the pancreatic tumor 4 days after the first therapy compared to all groups.

FIG. 19 shows the results of immunohistochemical images of pancreas tumors stained for anti-mouse PD1. Immunohistochemistry staining of PD1 positive T cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 μm paraffin sections were subsequently cut in a microtome (Leica RM2235, Germany). Mouse PD1 immunohistochemistry was performed with anti-mouse PD1 (R&D System, Germany) in the Leica autostainer (Leica ST5010, Germany) following the manufacture's protocols. Images were scanned with Olympus scanner. As early as after the first therapy administration, at day 4, a very high increase in the number of PD1 positive T cells was detected in the PD1-IL2v treated groups compared to vehicle group. Also a moderate increase in PD1 positive cells was seen in the combination of murine surrogate PD1 and murine surrogate FAP-IL2v when compared to vehicle. FIG. 19 shows that PD1-IL2v elicited an increase in PD1 positive T cell infiltration in the pancreatic tumor 4 days after the first therapy compared to all groups.

Figure 20:
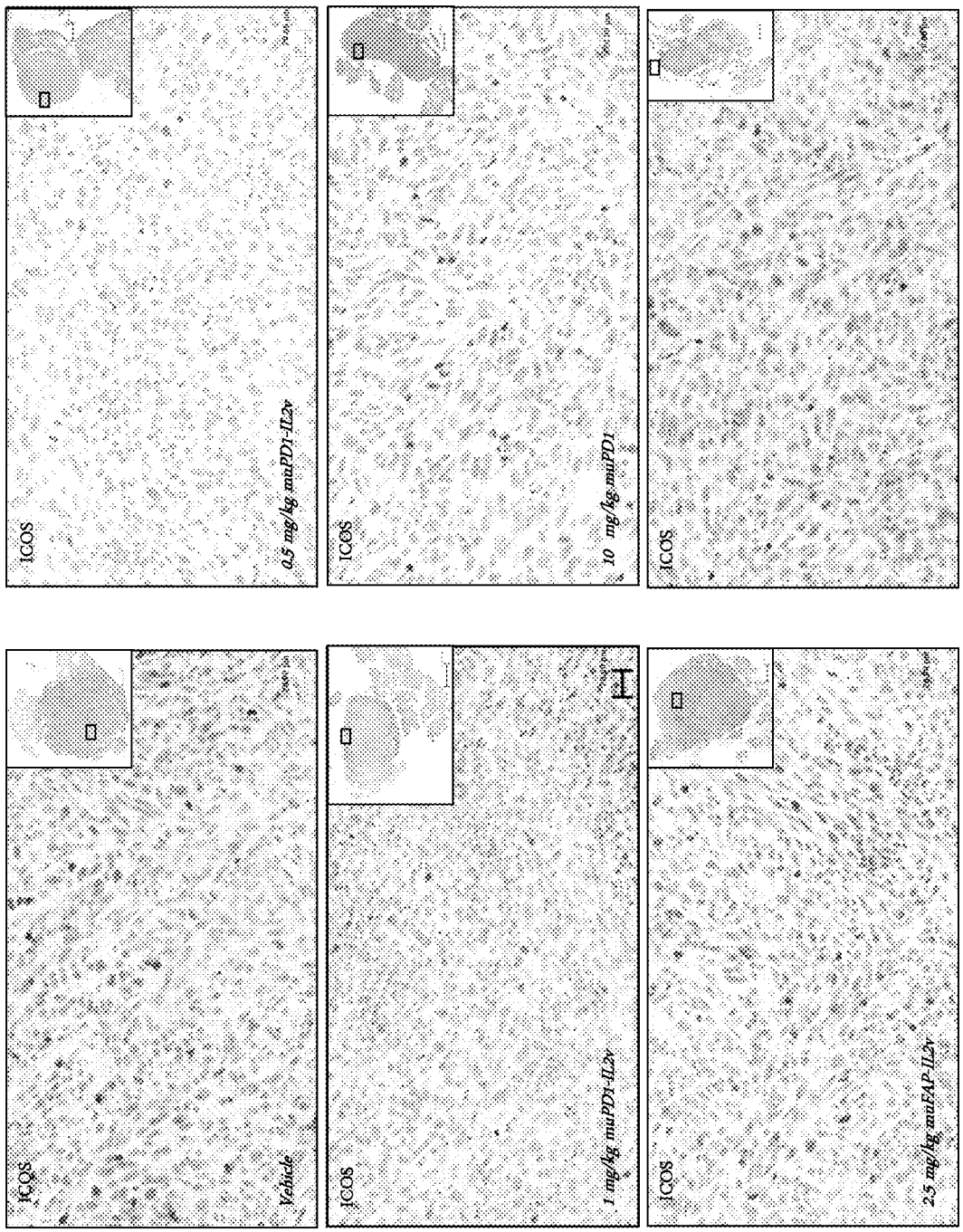
FIG. 20. Immunohistochemical images of pancreas tumors stained for anti-mouse ICOS.

FIG. 20 shows the results of immunohistochemical images of pancreas tumors stained for anti-mouse ICOS. Immunohistochemistry staining of ICOS positive T cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 μm paraffin sections were subsequently cut in a microtome (Leica RM2235, Germany). Mouse ICOS immunohistochemistry was performed with anti-mouse ICOS (My Biosource, Germany) in the Leica autostainer (Leica ST5010, Germany) following the manufacture's protocols. Images were scanned with Olympus scanner. As early as after the first therapy administration, at day 4, a decrease in the number of ICOS positive T cells was detected in the PD1-IL2v treated groups compared to vehicle group. FIG. 20 shows PD1-IL2v elicited a decreased in ICOS positive T cell infiltration in the pancreatic tumor 4 days after the first therapy compared to all groups.

Example 7

In Vivo Efficacy of PD1-IL2v Immuno-Conjugates in a Syngeneic Model of Mouse Tumor Cell Lines Compared to PD1 and FAP-IL2v Antibodies (Two Different Doses) as Single Agents and in Combination.

PD1-IL2v immune-conjugate was tested in comparison to murine surrogate PD1 plus murine surrogate FAP-IL2v combination with two different doses for its anti-tumoral efficacy in one syngeneic model. The syngeneic model used was the Panc02-Fluc pancreatic Syngeneic Model. The murine surrogate PD1-IL2v immune-conjugate was tested in the mouse pancreatic Panc02-Fluc transfectant cell line intra-pancreatically injected into Black 6 mice. Panc02-H7 cells (mouse pancreatic carcinoma) were originally obtained from the MD Anderson cancer center (Texas, USA) and after expansion deposited in the Roche-Glycart internal cell bank. Panc02-H7-Fluc cell line was produced in house by calcium transfection and sub-cloning techniques. Panc02-H7-Fluc was cultured in RPMI medium containing 10% FCS (Sigma), 500 μg/ml hygromicin and 1% of Glutamax. The cells were cultured at 37° C. in a water-saturated atmosphere at 5% $CO_2$. Passage 16 was used for transplantation. Cell viability was 83.3%. $1 \times 10^5$ cells per animal were injected into the pancreas of the mice using a 0.3 ml tuberculin syringe (BD Biosciences, Germany). For this a small incision was made at the left abdominal site of anesthetized Black 6 mouse. The peritoneal wall was opened and the pancreas carefully isolated with forceps. Ten microliters ($1 \times 10^5$ Panc02-H7-Fluc cells in RPMI medium) cell suspension was injected in the tail of the pancreas. Peritoneal wall and skin wounds were closed using 5/0 resolvable sutures.

Female Black 6 mice aged 10-12 weeks at the start of the experiment (Charles Rivers, Lyon, France) were maintained under specific-pathogen-free condition with daily cycles of 12 h light/12 h darkness according to committed guidelines (GV-Solas; Felasa; TierschG). The experimental study protocol was reviewed and approved by local government (ZH193/2014). After arrival, animals were maintained for one week to get accustomed to the new environment and for observation. Continuous health monitoring was carried out on a regular basis.

Mice were injected intra-pancreatically on study day 0 with $1 \times 10^5$ Panc02-Fluc cells, randomized and weighed. One week after the tumor cell injection mice were injected intravenously with PD1-IL2v and compare to the combination of PD1+FAP-IL2v Mabs with two different doses, once weekly for three weeks.

All mice were injected intravenously with 200 μl of the appropriate solution. The mice in the vehicle group were injected with Histidine Buffer and the treatment groups with the PD1-IL2v (1 mg/kg), PD1 (10 mg/kg) and FAP-IL2v (0.625 mg/kg or 1.25 mg/kg) antibodies or the combination of PD1+FAP-IL2v (10 mg/kg+1.25 mg/kg or 10 mg/kg+0.625 mg/kg) antibodies. To obtain the appropriate amount of immune-conjugates per 200 μl, the stock solutions were diluted with Histidine Buffer when necessary according to Table 4.

TABLE 4

Compounds, doses, formulation buffers and stock solution concentration.

| Compound | Dose | Formulation buffer | Concentration of stock solution (mg/mL) |
| --- | --- | --- | --- |
| muPDl-IL2v | 10 µg and 30 µg | 20 mM Histidine, 140 mM NaCl, 0.01% Tween20; pH 6.0 | 3.63 |
| muFAP-IL2v | 50 µg | 20 mM Histidine, 140 mM NaCl, 0.01% Tween20; pH 6.0 | 4.91 |
| muPDl | 200 µg | 20 mM Histidine, 140 mM NaCl, 0.01% Tween20; pH 6.0 | 5.84 |

For Bioluminescence imaging by IVIS® SPECTRUM, the mice are injected intra-peritoneal with 150 mg/kg of D-Luciferin 10 minutes before bioluminescence imaging acquisition (BLI) and later anesthetized with 4% isoflurane. Subsequently the mice are transferred into an isolation chamber, which is positioned into the IVIS® spectrum. In vivo BLI acquisitions are performed by acquiring the luminescence signal for 10-50 seconds. Data is stored as Radiance (photons)/sec/cm$^2$/sr. In vivo BLI data's analysis is performed with the Living Image® 4.4 software and represented by a tumor inhibition curve.

To evaluate the immune-pharmacodynamic by histology, 3 mice from selected groups were sacrificed 4 days after the first therapy by neck dislocation. The pancreas tumors were harvested and fix immediately in formalin 10%. The tissue was left in formalin solution overnight and later processed for FFPET (Leica 1020, Germany). 4 µm paraffin sections were subsequently cut in a microtome (Leica RM2235, Germany). Mouse CD3, CD8, PD1 and Granzyme B immunohistochemistry was performed in the Leica autostainer (Leica ST5010, Germany) following the manufacture's protocols. Images were scanned with Olympus scanner.

Figure 21:
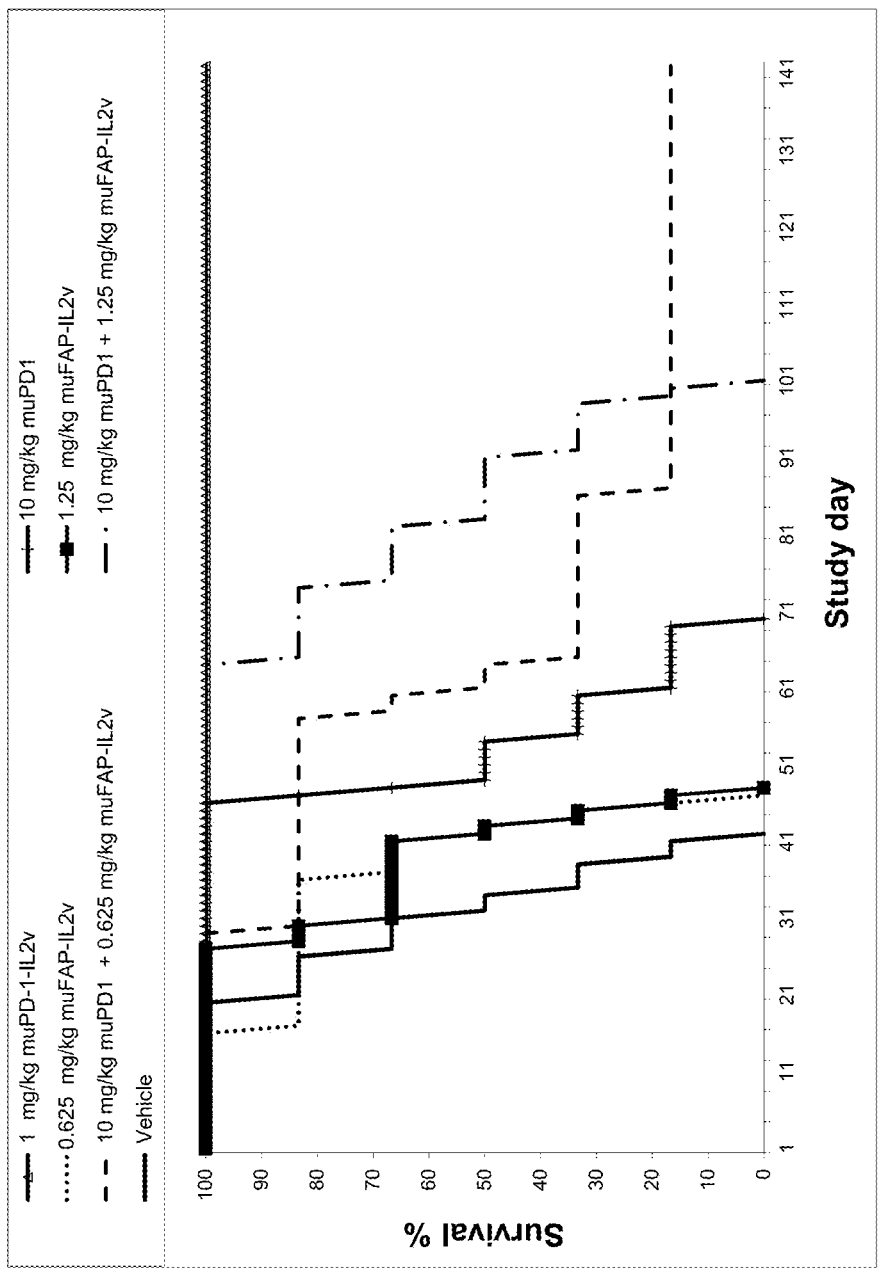
FIG. 21. Results of an efficacy experiment comparing muPD1-IL2v to FAP-IL2v and muPD1 as single agents and in combination.

FIG. 21 and Table 5 show the results of an efficacy experiment comparing muPD1-IL2v to muFAP-IL2v and muPD-1 antibodies as single agents and in combination. The Panc02-H7-Fluc transfectant pancreatic carcinoma cell line was injected into the pancreas in Black 6 mice to study survival in a pancreatic orthotopic syngeneic model. The amount of antibodies injected per mouse in mg/kg is the following: 1 mg/kg muPD1-IL2v, 10 mg/kg muPD1 and 0.625 or 1.25 mg/kg muFAP-IL2v antibodies. The antibodies were injected intravenously once per week for 4 weeks. Significant superior median and overall survival was observed in the 1 mg/kg muPD1-IL2v compared to all other single agents and the combination of muPD-1+muFAP-IL2v at both doses tested. Thus, it can be concluded that PD1-IL2v mediated superior efficacy in terms of enhanced median and overall survival compared to all other single agents, as well as the combinations of PD1+FAP-IL2v at both doses tested.

TABLE 5

Median and overall survival of Black 6 mice treated with PD1-IL2v, PD1, FAP-IL2v and a combination of PD-1 and FAP-IL2v antibody, in the Panc02-Fluc syngeneic tumor model.

| Groups | Median Survival in days | p-value vs control | Overall survival |
| --- | --- | --- | --- |
| Vehicle | 30 | 1.0000 | 0/6 |
| 1 mg/kg muPD-1-IL2v | Not reached | <0.0001*** | 6/6 |
| 10 mg/kg muPD1 + 0.625 mg/kg muFAP-IL2v | 62 | 0.0053* | 1/6 |
| 10 mg/kg muPD1 + 1.25 mg/kg muFAP-IL2v | 86 | 0.0005** | 0/6 |
| 0.625 mg/kg muFAP-IL2v | 36 | 0.2607 | 0/6 |
| 1.25 mg/kg muFAP-IL2v | 31 | 0.6834 | 0/6 |
| 10 mg/kg muPD1 | 48 | 0.0005** | 0/6 |

Figure 22:
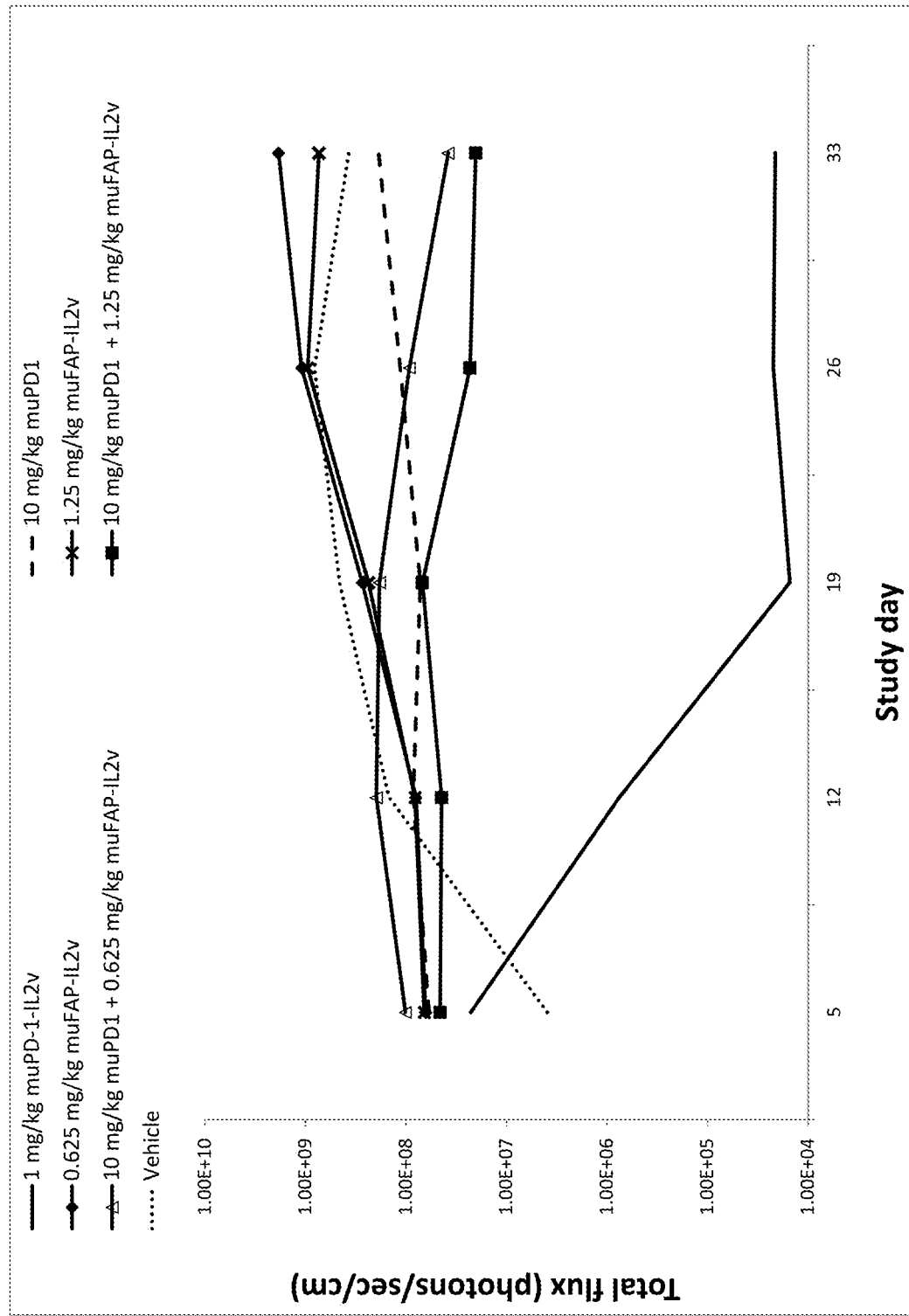
FIG. 22. Results of an efficacy experiment comparing muPD1-IL2v to FAP-IL2v, muPD1 and their combination with two different doses.

FIG. 22 shows the results of an efficacy experiment comparing muPD1-IL2v to FAP-IL2v, muPD1 and their combination with two different doses. The Panc02-H7-Fluc transfectant pancreatic carcinoma cell line was injected into the pancreas in Black 6 mice to study survival in a pancreatic orthotopic syngeneic model by means of bioluminescence. During the course of the study a reduction in the Panc02-Fluc bioluminescence signal was detected by IVIS® Spectrum in several treated groups, but only muPD1-IL2v therapy showed a complete disappearance of the BLI signal in all mice that lasted the whole duration of the experiment, indicative of a complete response in all 6 mice. FIG. 22 shows that PD1-IL2v mediated superior efficacy in terms of decreasing the bioluminescence signal (photons/second) compared to all other single agent and the combination groups.

Figure 23:
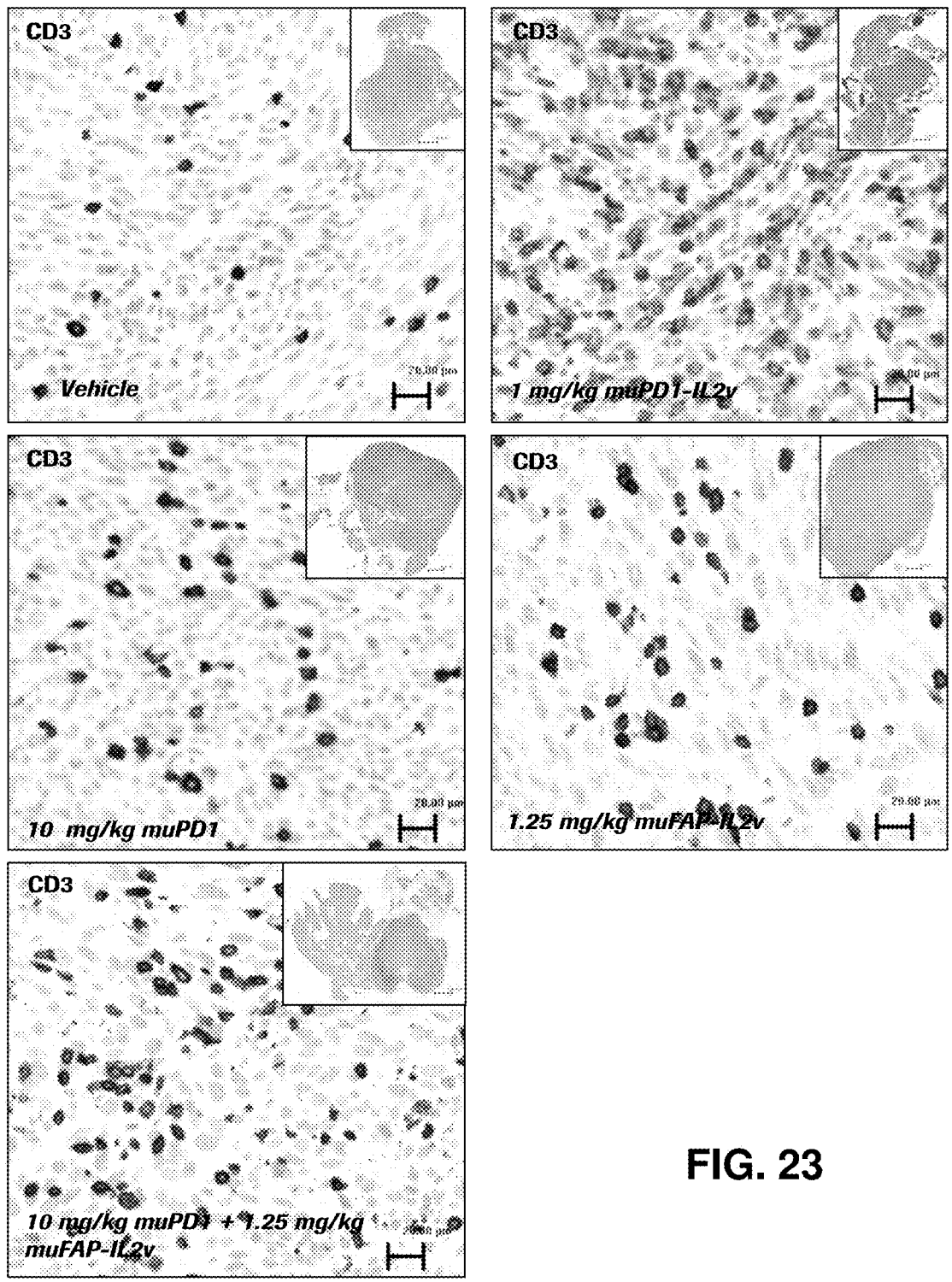
FIG. 23. Immunohistochemical images of pancreas tumors stained for anti-mouse CD3.

FIG. 23 shows the results of immunohistochemical images of pancreas tumors stained for anti-mouse CD3. Immunohistochemistry staining of CD3 T cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 µm paraffin sections were subsequently cut in a microtome (Leica RM2235, Germany). Mouse CD3 immunohistochemistry was performed with anti-mouse CD3 (Diagnostic Biosystem, Germany) in the Leica autostainer (Leica ST5010, Germany) following the manufacture's protocols. Images were scanned with Olympus scanner. As early as after the first therapy administration, at day 4, a very high increase in the number of CD3 positive T cells was detected in the muPD1-IL2v treated groups compared to vehicle group. Also a moderate increase in CD3 positive cells was seen in all the other therapeutic groups when compared to vehicle. FIG. 23 shows that PD1-IL2v elicited an increase in CD3 positive T cell infiltration in the pancreatic tumor 4 days after the first therapy compared to all groups.

Figure 24A:
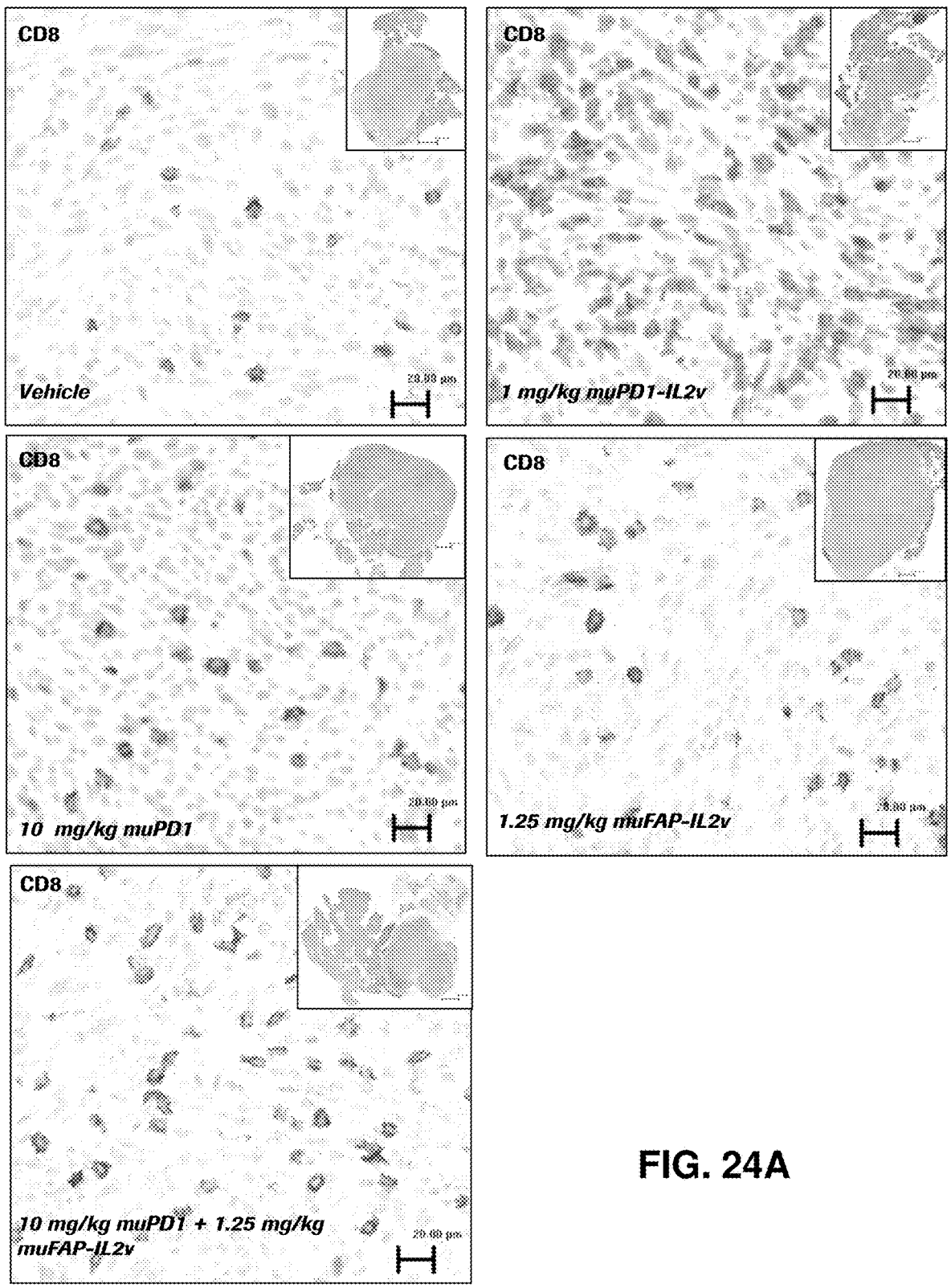
FIGS. 24A and 24B. Immunohistochemical images of pancreas tumors stained for anti-mouse CD8 (FIG. 24A) and the T cell quantification analysis (FIG. 24B).
Figure 24B:
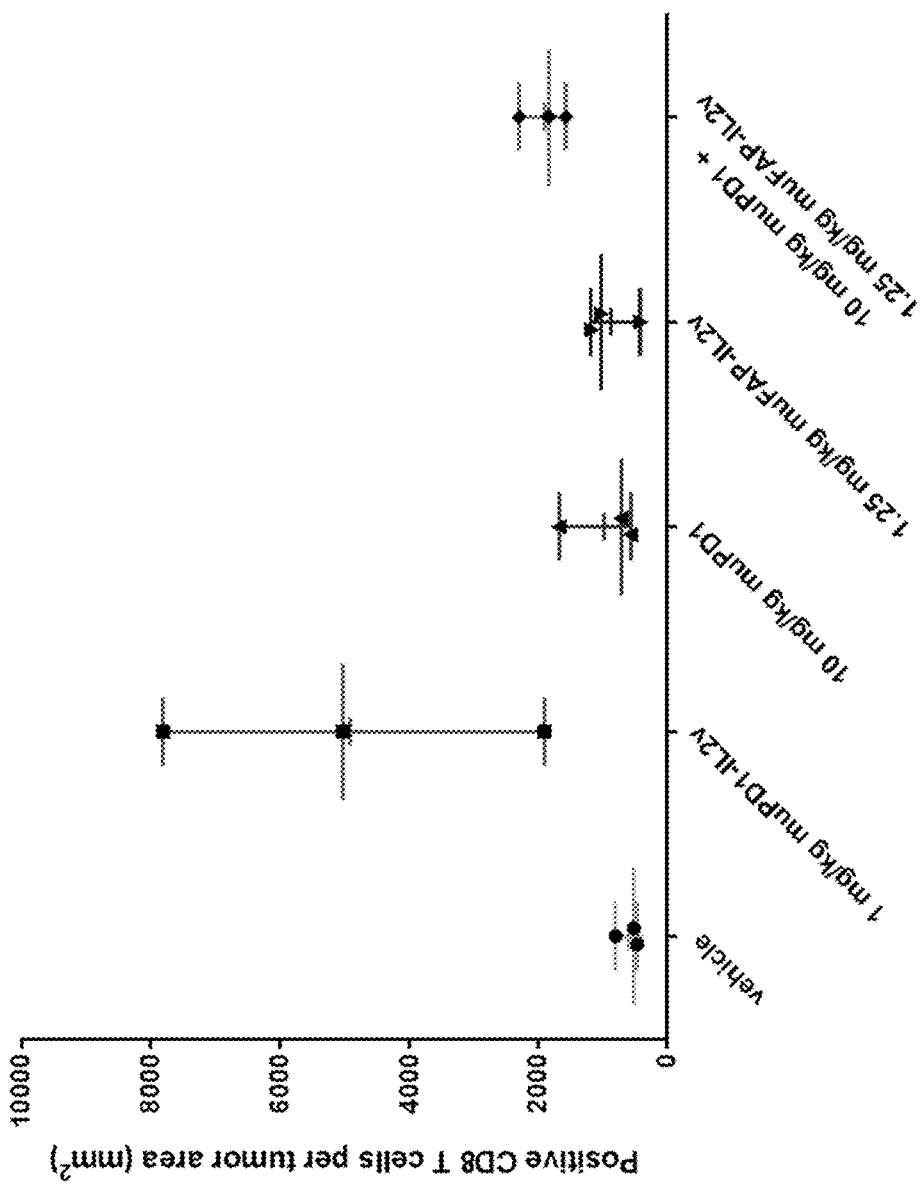

FIGS. 24A and 24B and table 6 show the results of immunohistochemical images of pancreas tumors stained for anti-mouse CD8 (FIG. 24A) and the T cell quantification analysis (FIG. 24B). Immunohistochemistry staining of CD8 T cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 µm paraffin sections were subsequently cut in a microtome (Leica RM2235, Germany). Mouse CD8 immunohistochemistry was performed with anti-mouse CD8 (Serotec, Germany) in the Leica autostainer (Leica ST5010, Germany) following the manufacture's protocols. Images were scanned with Olympus scanner. Quantification of muCD8 positive T cells was performed with Definiens software (Definiens, Germany). Statistics were analyzed by one way ANOVA with multiple comparison tests. As early as after the first therapy administration, at day 4, a significant increase in the number of CD8 positive T cells was detected in the muPD1-IL2v treated groups compared to all other groups. A tendency to increase in CD8 positive cells was also seen in all other therapeutic groups tested, but was not significant. Thus, FIGS. 24A and 24B show that PD1-IL2v elicited an increase in CD8 infiltration in the pancreatic tumor 4 days after the first therapy compared to all groups.

TABLE 6

CD8 positive T-cells.

| Groups | Number of CD8 positive T cells/mm$^2$ | p-value vs control |
|---|---|---|
| muPD1-IL2v 1 mg/kg | 4914 | 0.0032** |
| muPD1 10 mg/kg | 974 | 0.7395 |
| muFAP-IL2v 1.25 mg/kg | 872 | 0.8066 |
| muPD-1 10 mg/kg + muFAP-IL2v 1.25 mg/kg | 1899 | 0.2703 |
| Vehicle | 590 | 1 |

Figure 25A:
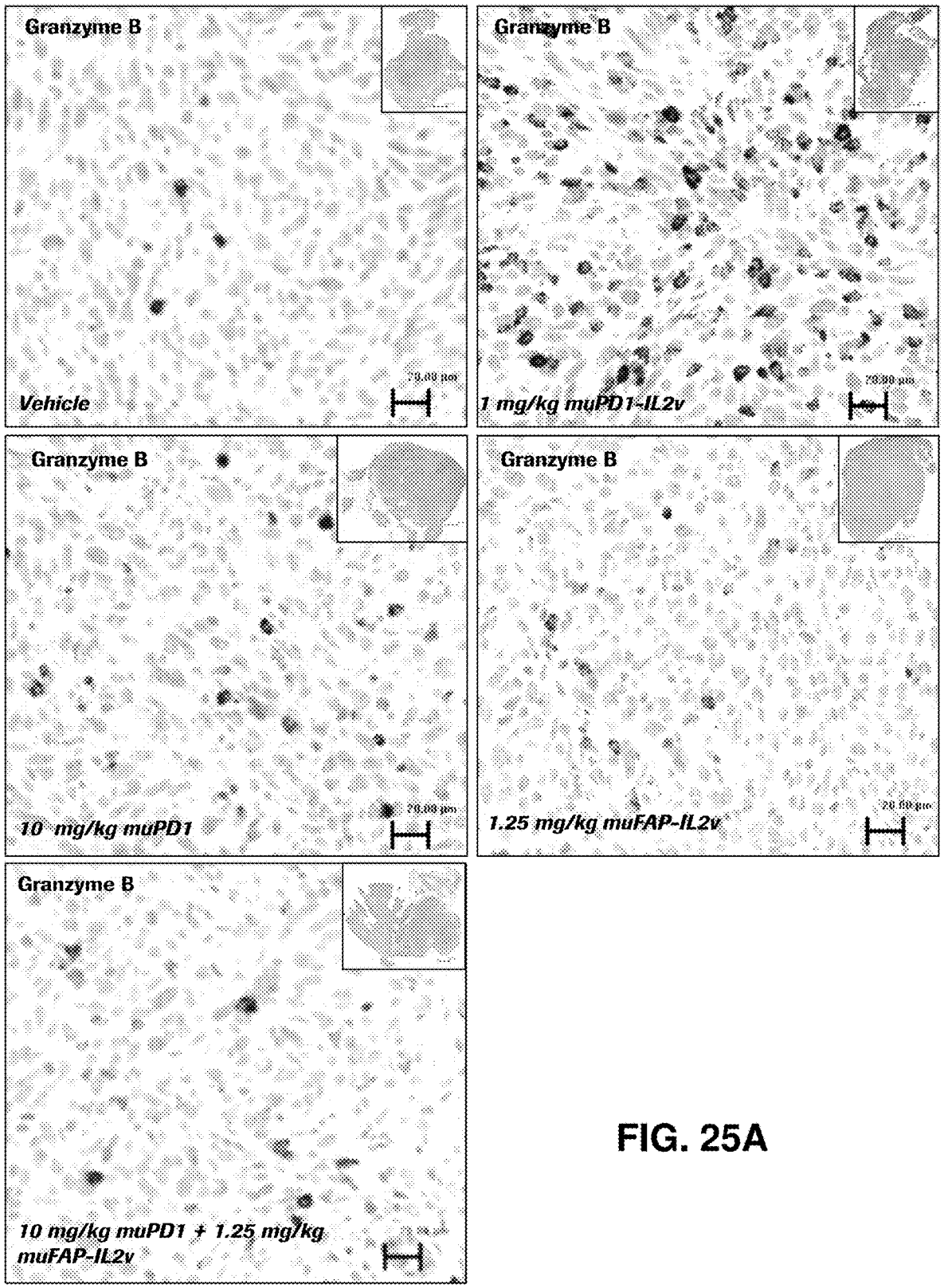
FIGS. 25A and 25B. Immunohistochemical images of pancreas tumors stained for anti-Granzyme B (FIG. 25A) and Granzyme B marker area quantification analysis (FIG. 25B).
Figure 25B:
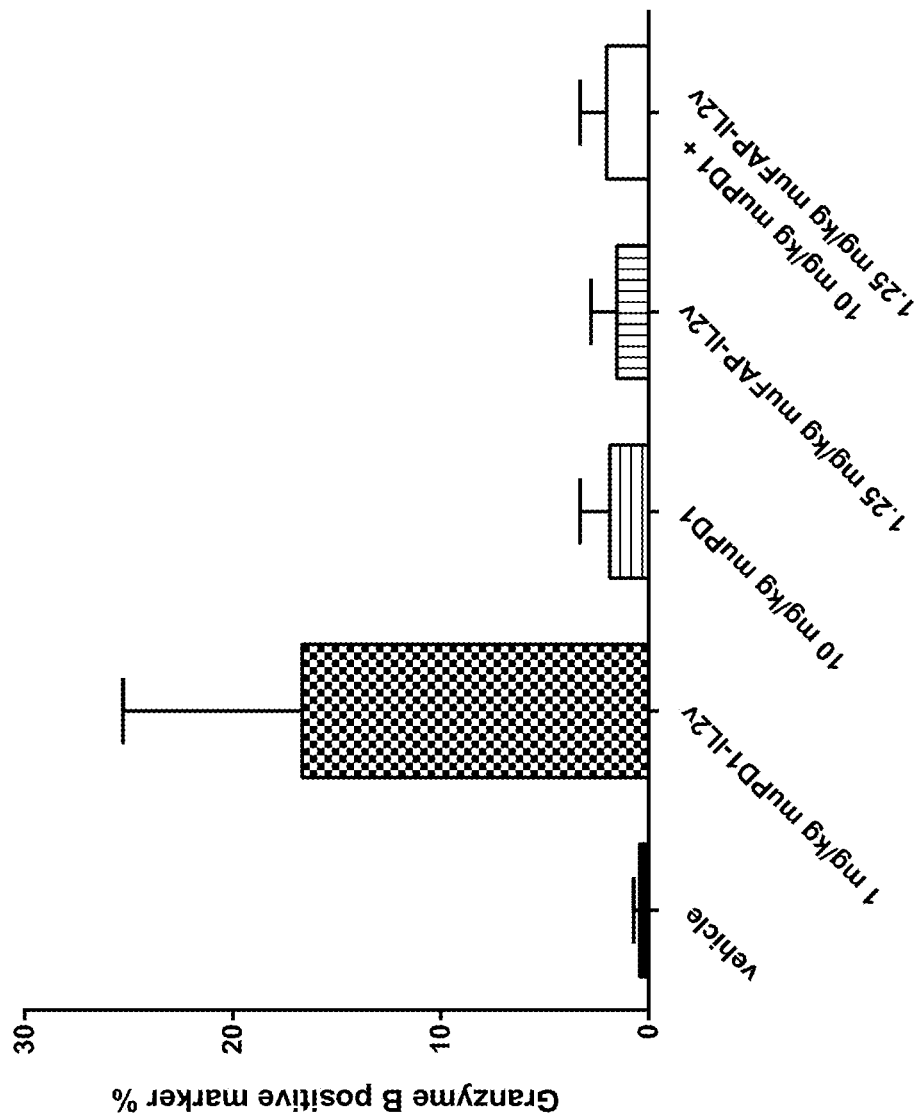

FIGS. 25A and 25B and table 7 show the results of immunohistochemical images of pancreas tumors stained for anti-Granzyme B (5A) and Granzyme B marker area quantification analysis (5B). Immunohistochemistry staining of Granzyme B was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 µm paraffin sections were subsequently cut in a microtome (Leica RM2235, Germany). Mouse Granzyme B immunohistochemistry was performed with anti-mouse Granzyme B (Abcam, Germany) in the Leica autostainer (Leica ST5010, Germany) following the manufacture's protocols. Images were scanned with Olympus scanner. Quantification of Granzyme B marker area was performed with Definiens software (Definiens, Germany). Statistics were analyzed by one way ANOVA with multiple comparison tests. As early as after the first therapy administration, at day 4, a significant increase in Granzyme B was detected in the muPD1-IL2v treated groups compared to all other groups. A tendency to increase in Granzyme B marker area was also seen in all other therapeutic groups tested, but was not significant. Thus, FIGS. 25A and 25B show that PD1-IL2v elicited an increase in Granzyme B positive area in the pancreatic tumor 4 days after the first therapy compared to all groups.

TABLE 7

Granzyme B positive area.

| Groups | % of Granzyme B positive area | p-value vs control |
|---|---|---|
| muPD1-IL2v 1 mg/kg | 16.67 | 0.0006** |
| muPD1 10 mg/kg | 1.867 | 0.6709 |
| muFAP-IL2v 1.25 mg/kg | 1.533 | 0.7442 |
| muPD-1 10 mg/kg + muFAP-IL2v 1.25 mg/kg | 2.033 | 0.6355 |
| Vehicle | 0.44 | 1 |

Figure 26A:
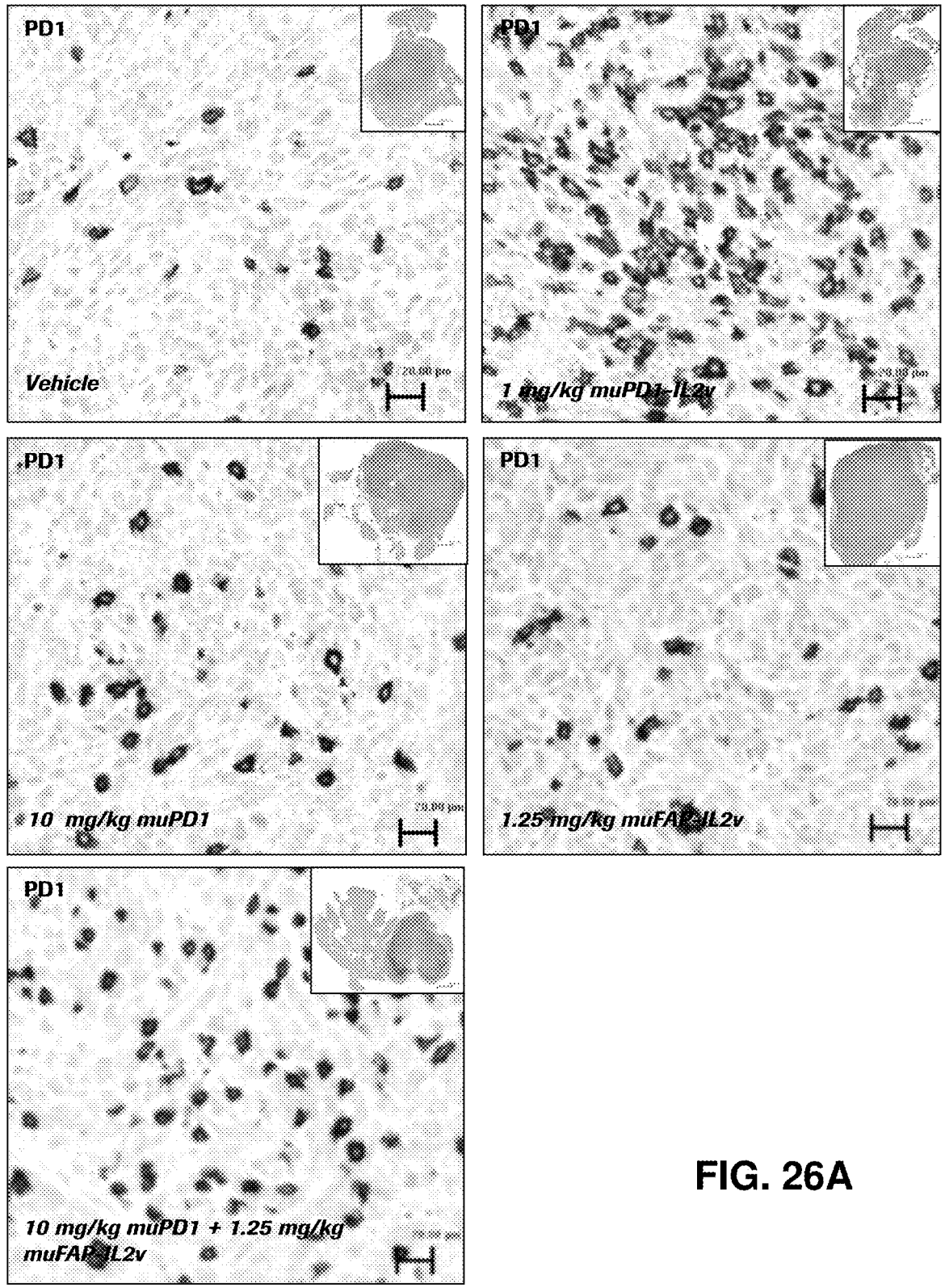
FIGS. 26A and 26B. Immunohistochemical images of pancreas tumors stained for anti-mouse PD1 (FIG. 26A) and the PD1 positive cell quantification analysis (FIG. 26B).
Figure 26B:
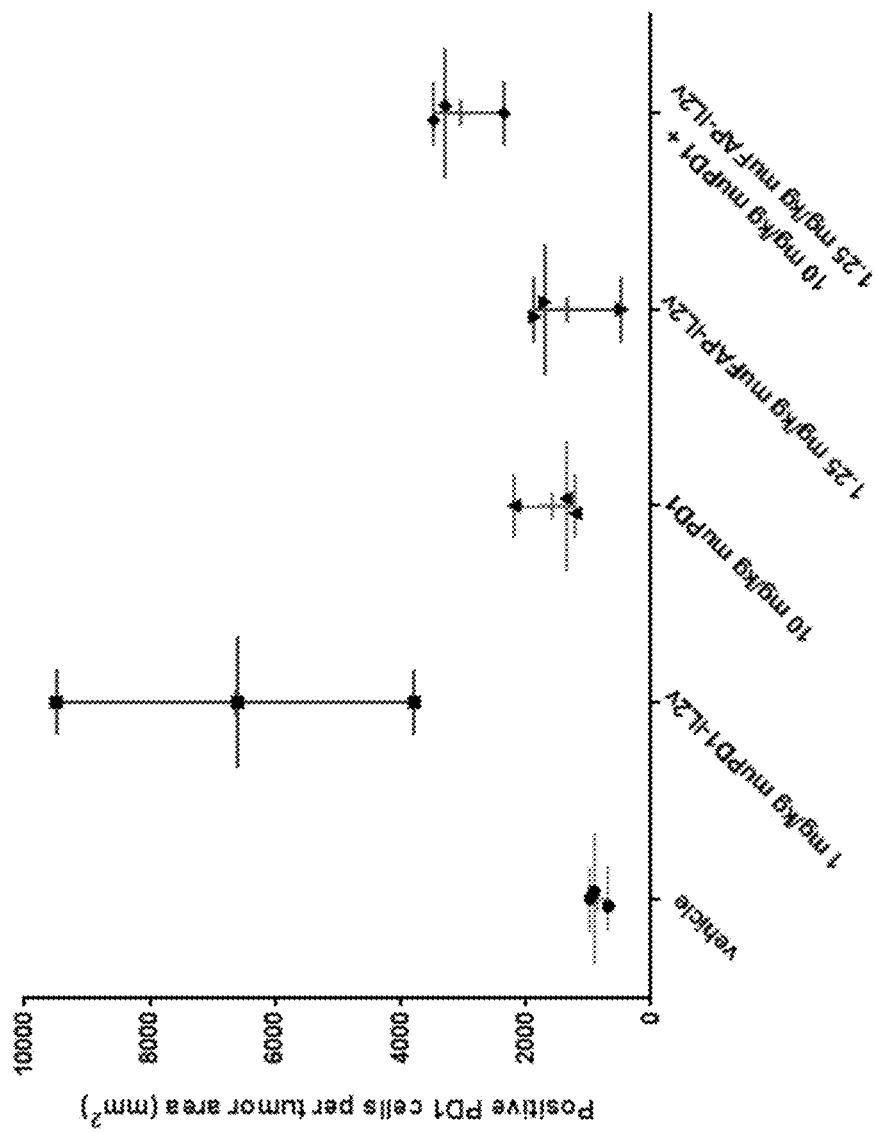
Figure 27A:
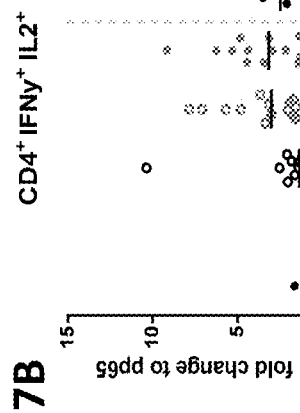
FIGS. 27A-27D. Ability of CD4 T cells to secrete IL-2 (FIG. 27A), IL-2 and IFN-γ(FIG. 27B) or IFN-γ(FIG. 27C) and to proliferate (FIG. 27D) upon 48 hours recall with CMV immunogenic protein pp65 in presence of either anti-PD-1 alone, in combination with IL-2v, or as fusion protein.
Figure 27B:
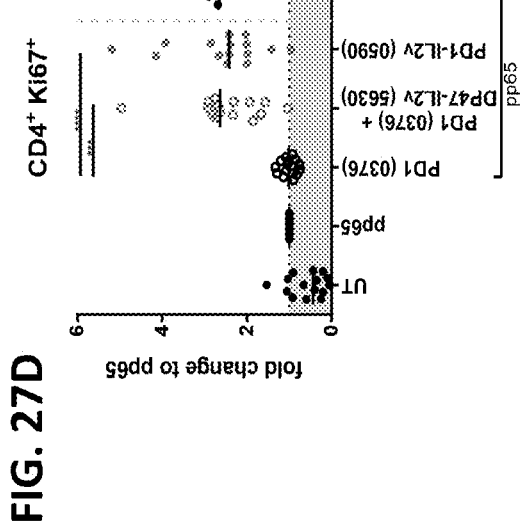
Figure 27C:
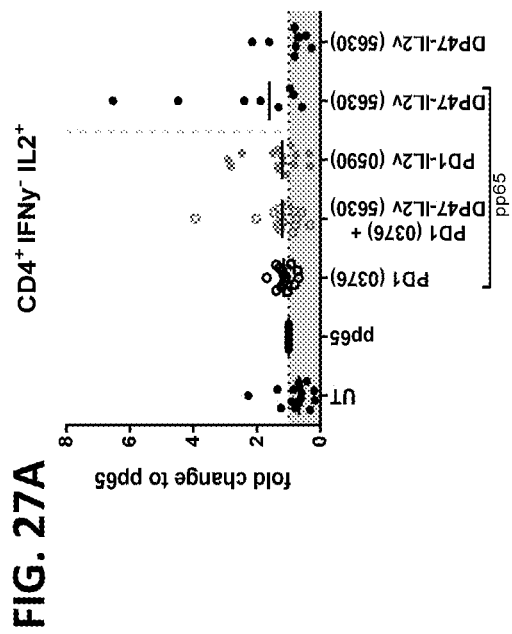
Figure 27D:
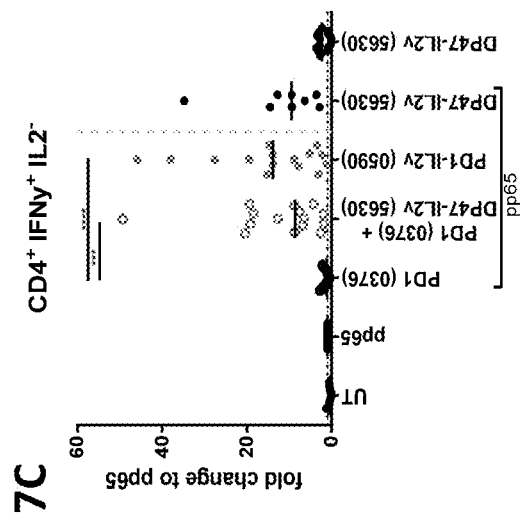

FIGS. 26A and 26B and table 8 present the results of immunohistochemical images of pancreas tumors stained for anti-mouse PD1 (FIG. 26A) and the PD1 positive cell quantification analysis (FIG. 26B). Immunohistochemistry staining of PD1 cells was performed on Black 6 mouse pancreas tumors derived from the indicated treatment groups. Tissue samples were prepared for immunohistochemical staining: tumors were harvested from animals after treatment administration, fix in formalin 10% (Sigma, Germany) and later processed for FFPET (Leica 1020, Germany). 4 µm paraffin sections were subsequently cut in a microtome (Leica RM2235, Germany). Mouse PD1 immunohistochemistry was performed with anti-mouse PD1 (Serotec, Germany) in the Leica autostainer (Leica ST5010, Germany) following the manufacture's protocols. Images were scanned with Olympus scanner. Quantification of muPD1 positive cells was performed with Definiens software (Definiens, Germany). Statistics were analyzed by one way ANOVA with multiple comparison tests. As early as after the first therapy administration, at day 4, a significant increase in the number of PD1 positive cells was detected in the muPD1-IL2v treated groups compared to all other groups. A tendency to increase in PD1 positive cells was also seen in all other therapeutic groups tested, but was not significant. Thus, FIGS. 26A and 26B show that PD1-IL2v elicited an increase in PD1 positive cells in the pancreatic tumor 4 days after the first therapy compared to all groups.

TABLE 8

PDI positive cells.

| Groups | Number of PDI positive cells/mm$^2$ | p-value vs control |
|---|---|---|
| muPD1-IL2v 1 mg/kg | 6628 | 0.0004** |
| muPD1 10 mg/kg | 1582 | 0.5331 |
| muFAP-IL2v 1.25 mg/kg | 1350 | 0.6705 |
| muPD-1 10 mg/kg + muFAP-IL2v 1.25 mg/kg | 3038 | 0.0803 |
| Vehicle | 858 | 1 |

Example 7

Effect of IL-2v Delivery to Exhausted Virus-Specific T Cells Through PD-1 Blockade PD-1 expression has been described for the first time on exhausted virus-specific T cells as result of chronic-exposure to viral antigens and it has been associated with T-cell inability to mount an effective anti-viral response. Virus-specific CD4 T cells able to simultaneously secrete IL-2 and IFN-γ confer protection from viral re-activation in chronic infections. Indeed, the polyfunctional signature of CD4 T cells has been associated with viral-control in healthy individuals infected by Cytomegalovirus (CMV), Epstein-Barr virus (EBV) and Herpes Simplex virus (HSV) as well as in those individuals infected with Human Immunodeficiency virus (HIV), who remain symptoms-free for several years.

In the context of chronic viral infections, we therefore developed an in-vitro assay to evaluate the effect of PD-1 targeting to deliver a mutated version of IL-2 (IL-2v) to dysfunctional antigen-specific T cells. To avoid restrictions on the amount of suitable donors for our assay, we opted for a CMV immunogenic viral-protein (pp65) as re-call antigen for T cells given that roughly 80% of the population is CMV-seropositive. Hence, we stimulated healthy human donor peripheral blood mononuclear cells (PBMCs) with CMV-pp65 (Miltenyi) in presence of our constructs at the concentration of 10 μg/ml. 43 hours later we blocked the protein transport from the Golgi by adding Golgi Plug (BD Bioscience, Brefeldin A) and Golgi Stop (BD Bioscience, Monensin) and incubated the cells at 37° C. for additional 5 hours. The cells were then washed, stained on the surface with anti-human CD3, CD4, CD8, CD62L and CD45RO antibodies before being fixed/permeabilized with the FoxP3 Transcription Factor Staining Buffer Set (eBioscience). At last we performed intracellular staining for IL-2, IFN-γ and Ki67 (all from eBioscience) to measure cell proliferation.

FIG. 27 shows the ability of CD4 T cells to secrete IL-2 (FIG. 27A), IL-2 and IFN-γ (FIG. 27B) or IFN-γ (FIG. 27C) and to proliferate (FIG. 27D) upon 48 hours recall with CMV immunogenic protein pp65 in presence of either anti-PD-1 alone, in combination with IL-2v, or as fusion protein. We observed a trend in PD1-IL2v ability to increase the frequencies of polyfunctional CD4 T cells, able to co-secrete IL-2 and IFN-γ (FIG. 21B), and a significant increase in the IFN-γ single secreting population (FIG. 21C), when compared with samples treated with pp65 and anti-PD1. Conversely, the combination of pp65 and untarget IL-2v (DP47-IL2v) increased the frequencies of IL-2 monofunctional CD4 T cells (FIG. 21A). As expected all cells treated with targeted or untargeted IL-2v proliferated as indicated by the positivity to Ki67 staining.

Figure 28:
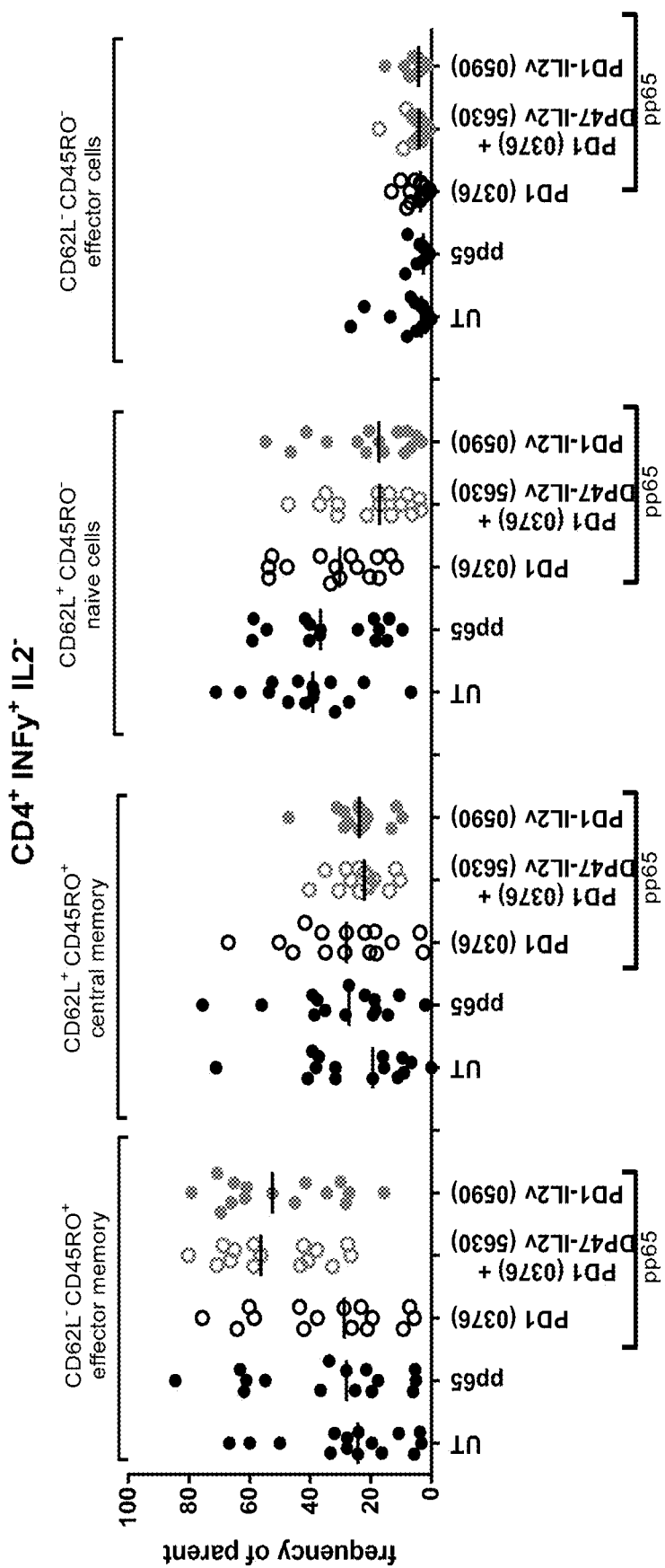
FIG. 28. Differentiation state, as per expression of CD45RO and CD62L, of virus-specific CD4 T cells secreting IFN-γupon 48 hours recall with CMV immunogenic protein pp65 in presence of either anti-PD-1 alone, in combination with IL-2v, or as fusion protein.
Figure 31A:
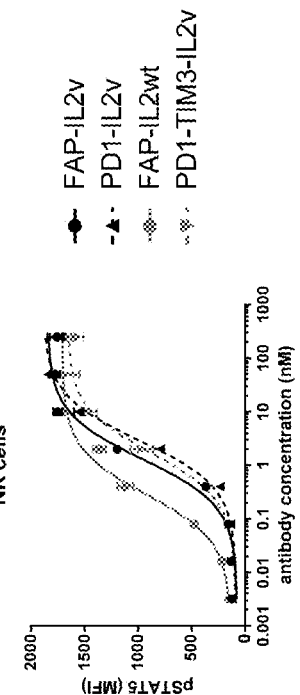
FIGS. 31A-31D. STAT5 assay on resting PBMCs of a third donor (CD8 T-cells (FIG. 31A), NK cells (FIG. 31B), CD4 T-cells (FIG. 31C) and regulatory T-cells (FIG. 31D)).
Figure 31B:
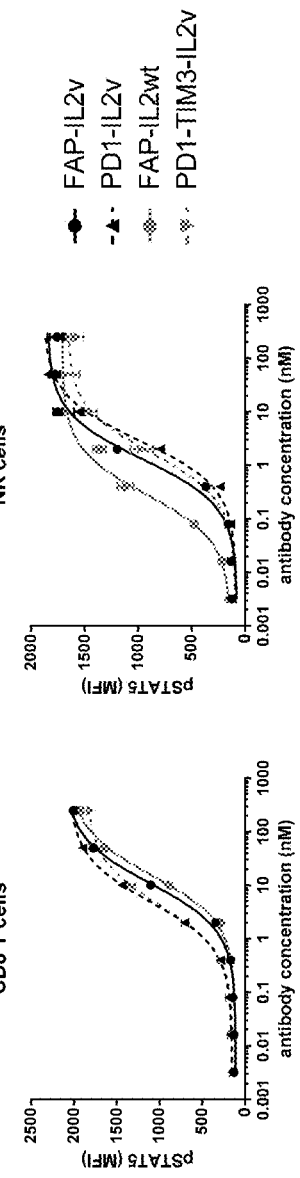
Figure 31C:
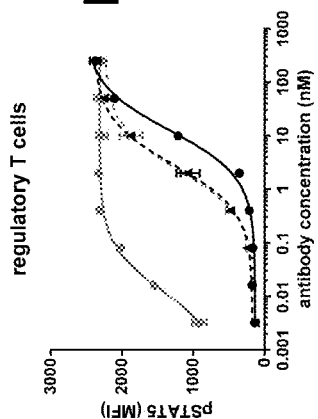
Figure 31D:
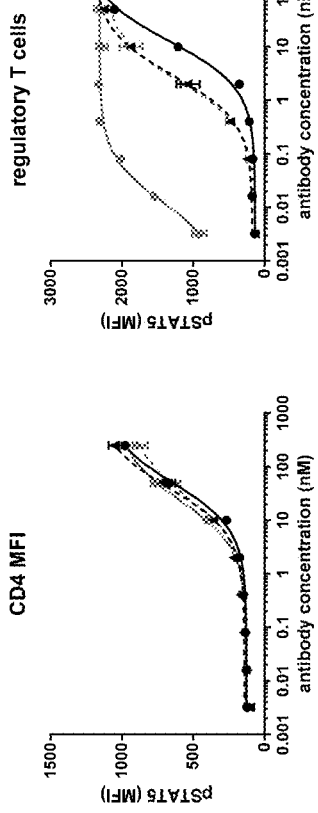

FIG. 28 shows differentiation state, as per expression of CD45RO and CD62L, of virus-specific CD4 T cells secreting IFN-γ upon 48 hours recall with CMV immunogenic protein pp65 in presence of either anti-PD-1 alone, in combination with IL-2v, or as fusion protein. A phenotype characterization of the expanded IFN-γ-secreting virus-specific CD4 T cells (FIG. 22) revealed an effector-memory (CD45RO+CD62L−) profile. We can conclude that delivering IL-2v to exhausted CMV-specific CD4 T cells through the PD1-IL2v fusion protein results in the expansion of a long-lived protective virus-specific population characterized by a differentiated memory profile and the ability to secrete both IL-2 and IFN-γ.

Example 8

Example 8A. Cell Activation of Donors 1 and 2 (pSTAT5 Assay)

Freshly isolated PBMCs from healthy donors were seeded in warm medium (RPMI1640, 10% FCS, 2 mM Glutamine) into a 96 well round bottom plate (200'000 cells/well). The plates were centrifuged at 300 g for 10 min and the supernatant was removed. The cells were re-suspended in 50 μl medium containing the IL2 molecules and stimulated for 20 min at 37° C. To preserve the phosphorylation status, the cells were immediately fixed after stimulation with equal amount of pre-warmed Cytofix buffer (554655, BD Bioscience) for 10 min at 37° C. Afterwards the plates were centrifuged for 10 min at 300 g and the supernatant was removed. To allow intracellular staining, the cells were permeabilized in 200 μl Phosflow Perm buffer III (558050, BD Bioscience) for 30 min at 4° C. Then the cells were washed twice with 150 μl cold FACS buffer and split in two 96 well round bottom plates and stained each with 20 μl of the antibody mix I or II for 60 min in the fridge. Antibody mix I was used to stain pSTAT5 in CD4 T cells and regulatory T cells and antibody mix II was used to stain pSTAT5 in CD8 T cells and NK cells. Afterwards the cells were washed twice with FACS buffer and re-suspended in 200 μl FACS buffer containing 2% PFA per well. The analysis was performed using a BD Fortessa flow cytometer.

The FACS antibody mixes according to table 9 and table 10 were used.

TABLE 9

FACS antibody mix 1 (CD4 T cells and regulatory T cells)

| Antibody | Volume/sample |
|---|---|
| CD4 PE/Cy7, clone SK3, mouse IgG1, κ (557852, BD Bioscience) | 0.5 μl/well |
| CD25 APC, clone M-A251, mouse IgG1, κ (356110, BioLegend) | 4 μl/well |
| PE Mouse anti-Human FoxP3 Clone 259D/C7 (560046, BD Bioscience) | 1 μl/well |
| A488 pSTAT5 (pY694), clone 47, mouse IgG1 (562075, BD Bioscience) | 1 μl/well |

TABLE 10

FACS antibody mix 11 (CD8 T cells and NK cells)

| Antibody | Volume/sample |
|---|---|
| CD3 PE/Cy7, clone UCHT1, mouse IgG1, κ (300420, BioLegend) | 1 μl/well |
| CD56 APC, clone HCD56, mouse IgG1, κ (318310, BioLegend) | 1 μl/well |
| CD8 PE, clone HIT8a, mouse IgG1 (555635, BD Bioscience) | 1 μl/well |
| A488 pSTAT5 (pY694), clone 47, mouse IgG1 (BD Bioscience) | 1 μl/well |

FIG. 29 shows STAT5 phosphorylation in CD8 T-cells (FIG. 29A), NK cells (FIG. 29B), CD4 T-cells (FIG. 29C) and regulatory T-cells (FIG. 29D) upon treatment of resting PBMCs of donor 1 with PD1-JL2v, FAP-JL2v and FAP-IL2 wt. All three tested molecules are equally potent on CD8 T-cells, NK cells and CD4 T-cells (excluding Tregs). FAP- IL2 wt is more potent in inducing STAT5 phosphorylation in Tregs followed by PD1-JL2v. FAP-JL2v has the lowest activity on Tregs.

FIG. 30 shows STAT5 phosphorylation in CD4 T-cells (FIG. 30A), CD8 T-cells (FIG. 30B), regulatory T-cells (FIG. 30C) and NK cells (FIG. 30D) upon treatment of resting PBMCs of donor 2 with FAP-IL2v, PD1-JL2c, FAP-IL2 wt and PD1-TJM3-JL2v. All four tested molecules are comparable active on CD8 T-cells, NK cells and CD4 T-cells (excluding Tregs). FAP-IL2 wt is more potent in inducing STAT5 phosphorylation in Tregs followed by PD1-JL2v. FAP-JL2v has the lowest activity on Tregs.

Example 8B. Cell Activation of Donors 3 and 4 (pSTAT5 Assay)

Frozen PBMCs isolated from healthy donors were thawed and cultured overnight at 37° C. On the next day the cells were seeded in warm medium (RPMI1640, 10% FCS, 2 mM Glutamine) into a 96 well round bottom plate (200'000 cells/well). The plates were centrifuged at 300 g for min and the supernatant was removed. The cells were re-suspended in 50 µl medium containing the IL2 molecules and stimulated for 20 min at 37° C. To preserve the phosphorylation status, the cells were immediately fixed after stimulation with equal amount of pre-warmed Cytofix buffer (554655, BD Bioscience) for 10 min at 37° C. Afterwards the plates were centrifuged for 10 min at 300 g and the supernatant was removed. To allow intracellular staining, the cells were permeabilized in 200 µl Phosflow Perm buffer III (558050, BD Bioscience) for 30 min at 4° C. Then the cells were washed twice with 150 µl cold FACS buffer and split in two 96 well round bottom plates and stained each with 20 µl of the antibody mix I or II for 60 min in the fridge. Antibody mix I was used to stain pSTAT5 in CD4 T cells and regulatory T cells and antibody mix II was used to stain pSTAT5 in CD8 T cells and NK cells. Afterwards the cells were washed twice with FACS buffer and re-suspended in 200 µl FACS buffer containing 2% PFA per well. The analysis was performed using a BD Fortessa flow cytometer. The FACS antibody mixes according to table 11 and table 12 were used.

TABLE 11

FACS antibody mix 1 (CD4 T cells and regulatory T cells)

| Antibody | Volume/sample |
|---|---|
| CD4 PE/Cy7, clone SK3, mouse IgG1, κ (557852, BD Bioscience) | 0.5 µl/well |
| CD25 APC, clone M-A251, mouse IgG1, κ (356110, BioLegend) | 4 µl/well |
| PE Mouse anti-Human FoxP3 Clone 259D/C7 (560046, BD Bioscience) | 1 µl/well |
| A488 pSTAT5 (pY694), clone 47, mouse IgG1 (562075, BD Bioscience) | 1 µl/well |

TABLE 12

FACS antibody mix 11 (CD8 T cells and NK cells)

| Antibody | Volume/sample |
|---|---|
| CD3 PE/Cy7, clone UCHT1, mouse IgG1, κ (300420, BioLegend) | 1 µl/well |

TABLE 12-continued

FACS antibody mix 11 (CD8 T cells and NK cells)

| Antibody | Volume/sample |
|---|---|
| CD56 APC, clone HCD56, mouse IgG1, κ (318310, BioLegend) | 1 µl/well |
| CD8 PE, clone HIT8a, mouse IgG1 (555635, BD Bioscience) | 1 µl/well |
| A488 pSTAT5 (pY694), clone 47, mouse IgG1 (BD Bioscience) | 1 µl/well |

FIG. 31 shows STAT5 phosphorylation in CD8 T-cells (FIG. 31A), NK cells (FIG. 31B), CD4 T-cells (FIG. 31C) and regulatory T-cells (FIG. 31D) upon treatment of resting PBMCs of donor 3 with FAP-IL2v, PD1-IL2v, FAP-IL2 wt, PD1-TIM3-IL2v. All four tested molecules are comparable active on CD8 T-cells, NK cells and CD4 T-cells (excluding Tregs). FAP-IL2 wt is more potent in inducing STAT5 phosphorylation in Tregs followed by PD1-IL2v. FAP-IL2v has the lowest activity on Tregs.

FIG. 32 shows STAT5 phosphorylation in CD8 T-cells (FIG. 32A), NK cells (FIG. 32B), CD4 T-cells (FIG. 32C) and regulatory T-cells (FIG. 32D) upon treatment of resting PBMCs of donor 4 with FAP-IL2v, PD1-IL2v, FAP-IL2 wt, PD1-TIM3-IL2v. All four tested molecules are comparable active on CD8 T cells, NK cells and CD4 T cells (excluding Tregs). FAP-IL2 wt is more potent in inducing STAT5 phosphorylation in Tregs followed by PD1-IL2v. FAP-IL2v has the lowest activity on Tregs.

Further Aspects of the Invention

1. An immunoconjugate comprising a mutant IL-2 polypeptide and an antibody that binds to PD-1,
wherein the mutant IL-2 polypeptide is a human IL-2 molecule comprising the amino acid substitutions F42A, Y45A and L72G (numbering relative to the human IL-2 sequence SEQ ID NO: 19).

2. An immunoconjugate comprising a mutant IL-2 polypeptide and an antibody that binds to PD-1,
wherein the mutant IL-2 polypeptide is a human IL-2 molecule comprising the amino acid substitutions F42A, Y45A and L72G (numbering relative to the human IL-2 sequence SEQ ID NO: 19); and
wherein the antibody comprises (a) a heavy chain variable region (VH) comprising a HVR-H1 comprising the amino acid sequence of SEQ ID NO:1, a HVR-H2 comprising the amino acid sequence of SEQ ID NO:2, a HVR-H3 comprising the amino acid sequence of SEQ ID NO:3, and a FR-H3 comprising the amino acid sequence of SEQ ID NO:7 at positions 71-73 according to Kabat numbering, and (b) a light chain variable region (VL) comprising a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:6.

3. An immunoconjugate comprising a mutant IL-2 polypeptide and an antibody that binds to PD-1,
wherein the mutant IL-2 polypeptide is a human IL-2 molecule comprising the amino acid substitutions F42A, Y45A and L72G (numbering relative to the human IL-2 sequence SEQ ID NO: 19); and
wherein the antibody comprises (a) a heavy chain variable region (VH) comprising a HVR-H1 comprising the amino acid sequence of SEQ ID NO:8, a HVR-H2 comprising the amino acid sequence of SEQ ID NO:9, and a HVR-H3 comprising the amino acid sequence of SEQ ID NO:10, and (b) a light chain variable region (VL) comprising a HVR-L1 comprising the amino acid sequence of SEQ ID NO:11, a HVR-L2 comprising the amino acid sequence of SEQ ID NO:12, and a HVR-L3 comprising the amino acid sequence of SEQ ID NO:13.

4. An immunoconjugate comprising a mutant IL-2 polypeptide and an antibody that binds to PD-1,
wherein the mutant IL-2 polypeptide is a human IL-2 molecule comprising the amino acid substitutions F42A, Y45A and L72G (numbering relative to the human IL-2 sequence SEQ ID NO: 19); and
wherein the antibody comprises (a) a heavy chain variable region (VH) comprising an amino acid sequence that is at least about 95%, 96%, 97%, 98%, 99% or 100% identical to the amino acid sequence of SEQ ID NO:14, and (b) a light chain variable region (VL) comprising an amino acid sequence that is at least about 95%, 96%, 97%, 98%, 99% or 100% identical to an amino acid sequence selected from the group consisting of SEQ ID NO:15, SEQ ID NO:16, SEQ ID NO: 17, and SEQ ID NO:18.

5. The immunoconjugate of any one of aspects 1 to 4, wherein the mutant IL-2 polypeptide further comprises the amino acid substitution T3A and/or the amino acid substitution C125A.

6. The immunoconjugate of any one of aspects 1 to 5, wherein the mutant IL-2 polypeptide comprises the sequence of SEQ ID NO: 20.

7. The immunoconjugate of any one of aspects 1 to 6, wherein the immunoconjugate comprises not more than one mutant IL-2 polypeptide.

8. The immunoconjugate of any one of aspects 1 to 7, wherein the antibody comprises an Fc domain composed of a first and a second subunit.

9. The immunoconjugate of aspect 8, wherein the Fc domain is an IgG class, particularly an IgG$_1$ subclass, Fc domain.

10. The immunoconjugate of aspect 8 or 9, wherein the Fc domain is a human Fc domain.

11. The immunoconjugate of any one of aspects 1 to 10, wherein the antibody is an IgG class, particularly an IgG$_1$ subclass immunoglobulin.

12. The immunoconjugate of any one of aspects 8 to 11, wherein the Fc domain comprises a modification promoting the association of the first and the second subunit of the Fc domain.

13. The immunoconjugate of any one of aspects 8 to 12, wherein in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

14. The immunoconjugate of any one of aspects 8 to 13, wherein in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

15. The immunoconjugate of aspect 14, wherein in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index).

16. The immunoconjugate of any one of aspects 8 to 15, wherein the mutant IL-2 polypeptide is fused at its amino-terminal amino acid to the carboxy-terminal amino acid of one of the subunits of the Fc domain, particularly the first subunit of the Fc domain, optionally through a linker peptide.

17. The immunoconjugate of aspect 16, wherein the linker peptide has the amino acid sequence of SEQ ID NO:21.

18. The immunoconjugate of any one of aspects 8 to 16, wherein the Fc domain comprises one or more amino acid substitution that reduces binding to an Fc receptor, particularly an Fcγ receptor, and/or effector function, particularly antibody-dependent cell-mediated cytotoxicity (ADCC).

19. The immunoconjugate of aspect 18, wherein said one or more amino acid substitution is at one or more position selected from the group of L234, L235, and P329 (Kabat EU index numbering).

20. The immunoconjugate of any one of aspects 8 to 19, wherein each subunit of the Fc domain comprises the amino acid substitutions L234A, L235A and P329G (Kabat EU index numbering).

21. The immunoconjugate of any one of claims 1 to 20, comprising a polypeptide comprising an amino acid sequence that is at least about 80%, 85%, 90%, 95%, 96%, 97%, 98%, 99% or 100% identical to the sequence of SEQ ID NO:22, a polypeptide comprising an amino acid sequence that is at least about 80%, 85%, 90%, 95%, 96%, 97%, 98%, 99% or 100% identical to the sequence of SEQ ID NO:23 or SEQ ID NO:24, and a polypeptide comprising an amino acid sequence that is at least about 80%, 85%, 90%, 95%, 96%, 97%, 98%, 99% or 100% identical to the sequence of SEQ ID NO:25.

22. The immunoconjugate of any one of aspects 1 to 21, essentially consisting of a mutant IL-2 polypeptide and an IgG$_1$ immunoglobulin molecule, joined by a linker sequence.

23. One or more isolated polynucleotide encoding the immunoconjugate of any one of aspects 1 to 22.

24. One or more vector, particularly expression vector, comprising the polynucleotide(s) of aspect 23.

25. A host cell comprising the polynucleotide(s) of aspect 23 or the vector(s) of aspect 24.

26. A method of producing an immunoconjugate comprising a mutant IL-2 polypeptide and an antibody that binds to PD-1, comprising (a) culturing the host cell of aspect 25 under conditions suitable for the expression of the immunoconjugate, and optionally (b) recovering the immunoconjugate.

27. An immunoconjugate comprising a mutant IL-2 polypeptide and an antibody that binds to PD-1, produced by the method of aspect 26.

28. A pharmaceutical composition comprising the immunoconjugate of any one of aspects 1 to 22 or 27 and a pharmaceutically acceptable carrier.

29. The immunoconjugate of any one of aspects 1 to 22 or 27 for use as a medicament.

30. The immunoconjugate of any one of aspects 1 to 22 or 27 for use in the treatment of a disease.

31. The immunoconjugate for use in the treatment of a disease of aspect 30, wherein said disease is cancer.
32. Use of the immunoconjugate of any one of aspects 1 to 22 or 27 in the manufacture of a medicament for the treatment of a disease.
33. The use of aspects 32, wherein said disease is cancer.
34. A method of treating a disease in an individual, comprising administering to said individual a therapeutically effective amount of a composition comprising the immunoconjugate of any one of aspects 1 to 22 or 27 in a pharmaceutically acceptable form.
35. The method of aspect 34, wherein said disease is cancer.
36. A method of stimulating the immune system of an individual, comprising administering to said individual an effective amount of a composition comprising the immunoconjugate of any one of aspects 1 to 22 or 27 in a pharmaceutically acceptable form.
37. The invention as described hereinbefore.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating cancer in an individual comprising administering to the individual a therapeutically effective amount of an immunoconjugate comprising an antibody and a mutant Interleukin-2 (IL-2) polypeptide, wherein
   (i) the antibody binds to Programmed Cell Death Protein 1 (PD-1) and comprises a heavy chain variable region (VH) and a light chain variable region (VL), wherein
      (a) the VH comprises a HVR-H1 comprising SEQ ID NO: 1, a HVR-H2 comprising SEQ ID NO: 2, a HVR-H3 comprising SEQ ID NO: 3, and a FR-H3 comprising SEQ ID NO: 7 at positions 71-73 according to Kabat numbering, and the VL comprises a HVR-L1 comprising SEQ ID NO: 4, a HVR-L2 comprising SEQ ID NO: 5, and a HVR-L3 comprising SEQ ID NO: 6; or
      (b) the VH comprises a HVR-H1 comprising SEQ ID NO: 8, a HVR-H2 comprising SEQ ID NO: 9, and a HVR-H3 comprising SEQ ID NO: 10, and the VL comprises a HVR-L1 comprising SEQ ID NO: 11, a HVR-L2 comprising SEQ ID NO: 12, and a HVR-L3 comprising SEQ ID NO: 13; and
   (ii) the mutant Interleukin-2 (IL-2) polypeptide comprises the amino acid sequence of SEQ ID NO: 19 with up to five amino acid substitutions, wherein three of said up to five amino acid substitutions are F42A, Y45A and L72G.

2. The method of claim 1, wherein the VH comprises the amino acid sequence of SEQ ID NO: 14, and the VL comprises an amino acid sequence selected from the group consisting of SEQ ID NO:15, SEQ ID NO:16, SEQ ID NO: 17, and SEQ ID NO:18.

3. The method of claim 1, wherein the five amino acid substitutions of the mutant IL-2 polypeptide are F42A, Y45A, L72G, T3A and C125A.

4. The method of claim 1, wherein the mutant IL-2 polypeptide comprises the sequence of SEQ ID NO: 20.

5. The method of claim 1, wherein the immunoconjugate comprises not more than one mutant IL-2 polypeptide.

6. The method of claim 1, wherein the antibody comprises an Fc domain comprising a first subunit and a second subunit.

7. The method of claim 6, wherein the Fc domain is an IgG class Fc domain.

8. The method of claim 6, wherein the Fc domain is a human Fc domain.

9. The method of claim 6, wherein the Fc domain comprises a modification promoting the association of the first subunit and the second subunit of the Fc domain.

10. The method of claim 6, wherein in the first subunit of the Fc domain the threonine residue at position 366 is replaced with a tryptophan residue (T366W), and in the second subunit of the Fc domain the tyrosine residue at position 407 is replaced with a valine residue (Y407V) (numberings according to Kabat EU index).

11. The method of claim 10, wherein in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index).

12. The method of claim 6, wherein the Fc domain comprises one or more amino acid substitutions that reduce binding to an Fc receptor or reduce effector function.

13. The method of claim 12, wherein the one or more amino acid substitutions are at one or more positions selected from the group consisting of L234, L235, and P329 (Kabat EU index numbering).

14. The method of claim 12, wherein each subunit of the Fc domain comprises the amino acid substitutions L234A, L235A and P329G (Kabat EU index numbering).

15. The method of claim 6, wherein the mutant IL-2 polypeptide is fused at its amino-terminal amino acid to the carboxy-terminal amino acid of one of the subunits of the Fc domain.

16. The method of claim 15, wherein the mutant IL-2 polypeptide is fused to the subunit of the Fc domain by a linker peptide comprising SEQ ID NO:21.

17. The method of claim 1, wherein the immunoconjugate comprising a polypeptide comprising SEQ ID NO: 22, a polypeptide comprising SEQ ID NO: 24, and a polypeptide comprising SEQ ID NO: 25.

18. The method of claim 1, wherein the immunoconjugate comprising a polypeptide comprising SEQ ID NO: 22, a polypeptide comprising SEQ ID NO: 23, and a polypeptide comprising SEQ ID NO: 25.

19. The method of claim 1, wherein the method treats the cancer in the individual.

20. The method of claim 1, wherein the method stimulates the immune system in the individual.

* * * * *